(12) United States Patent
Ek et al.

(10) Patent No.: US 7,896,883 B2
(45) Date of Patent: Mar. 1, 2011

(54) BONE RESURFACING SYSTEM AND METHOD

(75) Inventors: Steven W. Ek, Bolton, MA (US); George Sikora, Bridgewater, MA (US)

(73) Assignee: Arthrosurface, Inc., Franklin, MA (US)

( * ) Notice: Subject to any disclaimer, the term of this patent is extended or adjusted under 35 U.S.C. 154(b) by 119 days.

(21) Appl. No.: 12/397,095

(22) Filed: Mar. 3, 2009

(65) Prior Publication Data

US 2009/0216285 A1 Aug. 27, 2009

Related U.S. Application Data

(63) Continuation-in-part of application No. 12/027,121, filed on Feb. 6, 2008, which is a continuation-in-part of application No. 11/359,891, filed on Feb. 22, 2006, now Pat. No. 7,713,305, which is a continuation-in-part of application No. 10/373,463, filed on Feb. 24, 2003, now Pat. No. 7,678,151, which is a continuation-in-part of application No. 10/162,533, filed on Jun. 4, 2002, now Pat. No. 6,679,917, which is a continuation-in-part of application No. 10/024,077, filed on Dec. 17, 2001, now Pat. No. 6,610,067, which is a continuation-in-part of application No. 09/846,657, filed on May 1, 2001, now Pat. No. 6,520,964, application No. 12/397,095, which is a continuation-in-part of application No. 11/169,326, filed on Jun. 28, 2005, which is a continuation-in-part of application No. 10/994,453, filed on Nov. 22, 2004, which is a continuation-in-part of application No. 10/308,718, filed on Dec. 3, 2002, now Pat. No. 7,163,541.

(60) Provisional application No. 60/201,049, filed on May 1, 2000, provisional application No. 60/888,382, filed on Feb. 6, 2007, provisional application No. 60/583,549, filed on Jun. 28, 2004, provisional application No. 60/523,810, filed on Nov. 20, 2003, provisional application No. 61/033,136, filed on Mar. 3, 2008.

(51) Int. Cl.
A61F 5/00 (2006.01)

(52) U.S. Cl. ...................................... 606/86 R; 606/87

(58) Field of Classification Search ............... 606/86 R, 606/88, 87, 89, 79, 80, 96, 97, 98, 104, 102; 623/20.14
See application file for complete search history.

(56) References Cited

U.S. PATENT DOCUMENTS 992,819 A 5/1911 Springer
(Continued)

FOREIGN PATENT DOCUMENTS

AU 2001262308 12/2001
(Continued)

OTHER PUBLICATIONS

U.S. Office Action issued in related U.S. Appl. No. 11/326,133 dated Jun. 12, 2008.
(Continued)

*Primary Examiner*—Pedro Philogene
(74) *Attorney, Agent, or Firm*—Grossman Tucker Perreault & Pfleger PLLC

(57) ABSTRACT

The present disclosure relates to bone resurfacing. One embodiment includes a method for preparing an implant site in bone, comprising establishing a first working axis extending from said bone; establishing a second working axis extending from said bone, the second working axis is displaced from the first working axis; creating a first socket in the bone by reaming about the first working axis; and creating a second socket in the bone, adjacent the first socket, by reaming about the second working axis.

28 Claims, 39 Drawing Sheets

U.S. PATENT DOCUMENTS

| | | | |
|---|---|---|---|
| 1,451,610 A | 4/1923 | Gestas | |
| 2,267,925 A | 12/1941 | Johnston | |
| 2,570,465 A | 10/1951 | Lundholm | |
| 3,176,395 A | 4/1965 | Warner et al. | |
| 3,840,905 A | 10/1974 | Deane | |
| 4,016,651 A | 4/1977 | Kawahara et al. | |
| 4,034,418 A | 7/1977 | Jackson et al. | |
| 4,044,464 A | 8/1977 | Schiess et al. | |
| 4,158,894 A | 6/1979 | Worrell | |
| 4,344,192 A | 8/1982 | Imbert | |
| 4,433,687 A | 2/1984 | Burke et al. | |
| 4,462,120 A | 7/1984 | Rambert et al. | |
| 4,474,177 A | 10/1984 | Whiteside | |
| 4,484,570 A | 11/1984 | Sutter et al. | |
| 4,531,517 A | 7/1985 | Forte et al. | |
| 4,535,768 A | 8/1985 | Hourahane et al. | |
| 4,634,720 A | 1/1987 | Dorman et al. | |
| 4,655,752 A | 4/1987 | Honkanen et al. | |
| 4,661,536 A | 4/1987 | Dorman et al. | |
| 4,662,371 A | 5/1987 | Whipple et al. | |
| 4,664,669 A | 5/1987 | Ohyabu et al. | |
| 4,673,407 A | 6/1987 | Martin | |
| 4,693,986 A | 9/1987 | Vit et al. | |
| 4,712,545 A | 12/1987 | Honkanen | |
| 4,714,478 A | 12/1987 | Fischer | |
| 4,719,908 A | 1/1988 | Averill et al. | |
| 4,729,761 A | 3/1988 | White | |
| 4,788,970 A | 12/1988 | Karas et al. | |
| 4,823,780 A | 4/1989 | Odensten et al. | |
| 4,842,604 A | 6/1989 | Dorman et al. | |
| 4,896,663 A | 1/1990 | Vandewalls | |
| 4,911,153 A | 3/1990 | Border | |
| 4,920,958 A | 5/1990 | Walt et al. | |
| 4,927,421 A | 5/1990 | Goble et al. | |
| 4,936,853 A | 6/1990 | Fabian et al. | |
| 4,938,778 A | 7/1990 | Ohyabu et al. | |
| 4,940,467 A | 7/1990 | Tronzo | |
| 4,976,037 A | 12/1990 | Hines | |
| 4,978,258 A | 12/1990 | Lins | |
| 4,979,957 A | 12/1990 | Hodorek | |
| 4,989,110 A | 1/1991 | Zevin et al. | |
| 4,990,163 A | 2/1991 | Ducheyne et al. | |
| 4,997,434 A | 3/1991 | Seedhom et al. | |
| 4,998,938 A | 3/1991 | Ghajar et al. | |
| 5,007,930 A | 4/1991 | Dorman et al. | |
| 5,019,104 A | 5/1991 | Whiteside et al. | |
| 5,053,049 A | 10/1991 | Campbell | |
| 5,092,895 A | 3/1992 | Albrektsson et al. | |
| 5,100,405 A | 3/1992 | McLaren | |
| 5,127,920 A | 7/1992 | MacArthur | |
| 5,192,291 A | 3/1993 | Pannek, Jr. | |
| 5,201,881 A | 4/1993 | Evans | |
| 5,211,647 A | 5/1993 | Schmieding | |
| 5,224,945 A | 7/1993 | Pannek, Jr. | |
| 5,255,838 A | 10/1993 | Gladdish, Jr. et al. | |
| 5,263,498 A | 11/1993 | Caspari et al. | |
| 5,263,987 A | 11/1993 | Shah | |
| 5,282,863 A | 2/1994 | Burton | |
| 5,290,313 A | 3/1994 | Heldreth | |
| 5,312,411 A | 5/1994 | Steele | |
| 5,314,478 A | 5/1994 | Oka et al. | |
| 5,314,482 A | 5/1994 | Goodfellow et al. | |
| 5,324,295 A * | 6/1994 | Shapiro | 606/86 R |
| 5,336,224 A | 8/1994 | Selman | |
| 5,354,300 A | 10/1994 | Goble et al. | |
| 5,358,525 A | 10/1994 | Fox et al. | |
| 5,360,446 A | 11/1994 | Kennedy | |
| 5,374,270 A | 12/1994 | McGuire et al. | |
| 5,383,937 A | 1/1995 | Mikhail | |
| 5,387,218 A | 2/1995 | Meswania | |
| 5,395,401 A | 3/1995 | Bahler | |
| 5,409,490 A * | 4/1995 | Ethridge | 606/80 |
| 5,409,494 A | 4/1995 | Morgan | |
| 5,413,608 A | 5/1995 | Keller | |
| 5,423,822 A | 6/1995 | Hershberger | |
| 5,458,643 A | 10/1995 | Oka et al. | |
| 5,480,443 A | 1/1996 | Elias | |
| 5,486,178 A | 1/1996 | Hodge | |
| 5,509,918 A | 4/1996 | Romano | |
| 5,520,695 A | 5/1996 | Luckman | |
| 5,522,900 A | 6/1996 | Hollister | |
| 5,534,031 A | 7/1996 | Matsuzaki et al. | |
| 5,540,696 A | 7/1996 | Booth, Jr. et al. | |
| 5,580,353 A | 12/1996 | Mendes et al. | |
| 5,591,170 A | 1/1997 | Spievack et al. | |
| 5,593,450 A | 1/1997 | Scott et al. | |
| 5,595,193 A | 1/1997 | Walus et al. | |
| 5,601,550 A | 2/1997 | Esser | |
| 5,616,146 A | 4/1997 | Murray | |
| 5,620,055 A | 4/1997 | Javerlhac | |
| 5,624,463 A | 4/1997 | Stone et al. | |
| 5,632,745 A | 5/1997 | Schwartz | |
| 5,634,927 A * | 6/1997 | Houston et al. | 606/96 |
| 5,645,598 A | 7/1997 | Brosnahan, III | |
| 5,681,311 A | 10/1997 | Foley et al. | |
| 5,682,886 A | 11/1997 | Delp et al. | |
| 5,683,400 A | 11/1997 | McGuire | |
| 5,683,465 A | 11/1997 | Shinn et al. | |
| 5,683,466 A | 11/1997 | Viatle | |
| 5,700,264 A | 12/1997 | Zucherman et al. | |
| 5,700,265 A | 12/1997 | Romano | |
| 5,702,401 A | 12/1997 | Shaffer | |
| 5,702,465 A | 12/1997 | Burkinshaw | |
| 5,702,467 A | 12/1997 | Gabriel et al. | |
| 5,741,266 A | 4/1998 | Moran et al. | |
| 5,765,973 A | 6/1998 | Hirsch et al. | |
| 5,769,855 A | 6/1998 | Bertin et al. | |
| 5,769,899 A | 6/1998 | Schwartz et al. | |
| 5,771,310 A | 6/1998 | Vannah | |
| 5,776,137 A | 7/1998 | Katz | |
| 5,782,835 A | 7/1998 | Hart et al. | |
| 5,800,440 A | 9/1998 | Stead | |
| 5,810,851 A | 9/1998 | Yoon | |
| 5,817,095 A | 10/1998 | Smith | |
| 5,824,087 A | 10/1998 | Aspden et al. | |
| 5,824,105 A | 10/1998 | Ries et al. | |
| RE36,020 E | 12/1998 | Moore et al. | |
| 5,882,350 A | 3/1999 | Ralph et al. | |
| 5,885,297 A | 3/1999 | Matsen, III | |
| 5,885,298 A | 3/1999 | Herrington et al. | |
| 5,888,210 A | 3/1999 | Draenert | |
| 5,893,889 A | 4/1999 | Harrington | |
| 5,895,390 A | 4/1999 | Moran et al. | |
| 5,911,126 A | 6/1999 | Massen | |
| 5,918,604 A | 7/1999 | Whelan | |
| 5,919,196 A | 7/1999 | Bobic et al. | |
| 5,928,239 A | 7/1999 | Mirza | |
| 5,928,286 A | 7/1999 | Ashby et al. | |
| 5,964,752 A | 10/1999 | Stone | |
| 5,964,768 A | 10/1999 | Huebner | |
| 5,964,808 A | 10/1999 | Blaha et al. | |
| 5,968,050 A | 10/1999 | Torrie | |
| 5,989,269 A | 11/1999 | Vibe-Hansen et al. | |
| 5,990,382 A | 11/1999 | Fox | |
| 5,997,543 A | 12/1999 | Truscott | |
| 5,997,582 A | 12/1999 | Weiss | |
| 6,004,323 A | 12/1999 | Park et al. | |
| 6,010,502 A | 1/2000 | Bagby | |
| 6,015,411 A | 1/2000 | Ohkoshi et al. | |
| 6,017,348 A | 1/2000 | Hart et al. | |
| 6,019,767 A | 2/2000 | Howell | |
| 6,019,790 A | 2/2000 | Holmberg et al. | |
| 6,045,564 A | 4/2000 | Walen | |
| 6,052,909 A | 4/2000 | Gardner | |

| | | | | | | |
|---|---|---|---|---|---|---|
| 6,059,831 | A | 5/2000 | Braslow | 7,156,880 B2 | 1/2007 | Evans et al. |
| 6,071,310 | A | 6/2000 | Picha et al. | 7,160,305 B2 | 1/2007 | Schmieding |
| 6,081,741 | A | 6/2000 | Hollis | 7,163,541 B2 | 1/2007 | Ek |
| 6,086,593 | A | 7/2000 | Bonutti | 7,166,133 B2 | 1/2007 | Evans et al. |
| 6,102,948 | A | 8/2000 | Brosnahan, III | 7,192,431 B2 | 3/2007 | Hangody et al. |
| 6,120,542 | A | 9/2000 | Camino et al. | 7,204,839 B2 | 4/2007 | Dreyfuss et al. |
| 6,132,433 | A | 10/2000 | Whelan | 7,204,854 B2 | 4/2007 | Guederian et al. |
| 6,146,385 | A | 11/2000 | Torrie et al. | 7,235,107 B2 | 6/2007 | Evans et al. |
| 6,149,654 | A | 11/2000 | Johnson | 7,238,189 B2 | 7/2007 | Schmieding et al. |
| 6,152,960 | A | 11/2000 | Pappas | 7,241,316 B2 | 7/2007 | Evans et al. |
| 6,159,216 | A | 12/2000 | Burkinshaw et al. | 7,264,634 B2 | 9/2007 | Schmieding |
| 6,165,223 | A | 12/2000 | Metzger et al. | 7,290,347 B2 | 11/2007 | Augustino et al. |
| 6,168,626 | B1 | 1/2001 | Hyon et al. | 7,303,577 B1 | 12/2007 | Dean |
| 6,171,340 | B1 | 1/2001 | McDowell | 7,311,702 B2 | 12/2007 | Tallarida et al. |
| 6,193,724 | B1 | 2/2001 | Chan | 7,361,195 B2 | 4/2008 | Schwartz et al. |
| 6,206,885 | B1 | 3/2001 | Ghahremani et al. | 7,510,558 B2 | 3/2009 | Tallarida |
| 6,217,549 | B1 | 4/2001 | Selmon et al. | 7,569,059 B2 | 8/2009 | Cerundolo |
| 6,217,619 | B1 | 4/2001 | Keller | 7,641,658 B2 | 1/2010 | Shaolian et al. |
| 6,235,060 | B1 | 5/2001 | Kubein-Meesenburg et al. | 2001/0012967 A1 | 8/2001 | Mosseri |
| 6,251,143 | B1 | 6/2001 | Schwartz et al. | 2001/0039455 A1 | 11/2001 | Simon et al. |
| 6,280,474 | B1 | 8/2001 | Cassidy et al. | 2001/0056266 A1 | 12/2001 | Tallarida et al. |
| 6,299,645 | B1 | 10/2001 | Ogden | 2002/0055783 A1 | 5/2002 | Tallarida et al. |
| 6,299,648 | B1 | 10/2001 | Doubler et al. | 2002/0106393 A1 | 8/2002 | Bianchi et al. |
| 6,306,142 | B1 | 10/2001 | Johanson et al. | 2002/0138150 A1 | 9/2002 | Leclercq |
| 6,315,798 | B1 | 11/2001 | Ashby et al. | 2002/0147498 A1 | 10/2002 | Tallarida et al. |
| 6,322,500 | B1 | 11/2001 | Sikora et al. | 2003/0028196 A1 | 2/2003 | Bonutti |
| 6,328,752 | B1 | 12/2001 | Sjostrom et al. | 2003/0060887 A1 | 3/2003 | Ek |
| 6,342,075 | B1 | 1/2002 | MacArthur | 2003/0065391 A1 | 4/2003 | Re et al. |
| 6,358,251 | B1 | 3/2002 | Mirza | 2003/0100953 A1 | 5/2003 | Rosa et al. |
| 6,358,253 | B1 | 3/2002 | Torrie et al. | 2003/0105465 A1 | 6/2003 | Schmieding et al. |
| 6,375,658 | B1 | 4/2002 | Hangody et al. | 2003/0120276 A1 | 6/2003 | Tallarida et al. |
| 6,383,188 | B2 | 5/2002 | Kuslich | 2003/0120278 A1 | 6/2003 | Morgan et al. |
| 6,415,516 | B1 | 7/2002 | Tirado et al. | 2003/0130741 A1 | 7/2003 | McMinn |
| 6,443,954 | B1 | 9/2002 | Bramlet et al. | 2003/0171756 A1 | 9/2003 | Fallin et al. |
| 6,461,373 | B2 | 10/2002 | Wyman et al. | 2003/0181878 A1 | 9/2003 | Tallarida et al. |
| 6,468,309 | B1 | 10/2002 | Lieberman | 2003/0204195 A1 | 10/2003 | Keane et al. |
| 6,478,801 | B1 | 11/2002 | Ralph et al. | 2003/0216669 A1 | 11/2003 | Lang et al. |
| 6,482,210 | B1 | 11/2002 | Skiba et al. | 2003/0225456 A1 | 12/2003 | Ek |
| 6,494,914 | B2 | 12/2002 | Brown | 2003/0225457 A1 | 12/2003 | Justin et al. |
| 6,520,964 | B2 | 2/2003 | Tallarida et al. | 2004/0015170 A1 | 1/2004 | Tallarida et al. |
| 6,527,754 | B1 | 3/2003 | Tallarida et al. | 2004/0034359 A1 | 2/2004 | Schmieding et al. |
| 6,530,956 | B1 | 3/2003 | Mansmann | 2004/0034437 A1 | 2/2004 | Schmieding |
| 6,540,786 | B2 | 4/2003 | Chibrac et al. | 2004/0082906 A1 | 4/2004 | Tallarida et al. |
| 6,551,322 | B1 | 4/2003 | Lieberman | 2004/0106928 A1 | 6/2004 | Ek |
| 6,554,866 | B1 | 4/2003 | Aicher et al. | 2004/0133276 A1 | 7/2004 | Lang et al. |
| 6,575,982 | B1 | 6/2003 | Bonutti | 2004/0138754 A1 | 7/2004 | Lang et al. |
| 6,585,666 | B2 | 7/2003 | Suh et al. | 2004/0138758 A1 | 7/2004 | Evans et al. |
| 6,591,581 | B2 | 7/2003 | Schmieding | 2004/0148030 A1 | 7/2004 | Ek |
| 6,599,321 | B2 | 7/2003 | Hyde et al. | 2004/0153087 A1 | 8/2004 | Sanford et al. |
| 6,607,561 | B2 | 8/2003 | Brannon | 2004/0167632 A1 | 8/2004 | Wen et al. |
| 6,610,067 | B2 | 8/2003 | Tallarida | 2004/0193281 A1 | 9/2004 | Grimes |
| 6,626,950 | B2 | 9/2003 | Brown et al. | 2004/0199166 A1 | 10/2004 | Schmieding et al. |
| 6,679,917 | B2 | 1/2004 | Ek | 2004/0210309 A1 | 10/2004 | Denzer et al. |
| 6,746,451 | B2 | 6/2004 | Middleton et al. | 2004/0220574 A1 | 11/2004 | Pelo et al. |
| 6,755,837 | B2 | 6/2004 | Ebner | 2004/0230315 A1 | 11/2004 | Ek |
| 6,770,078 | B2 | 8/2004 | Bonutti | 2004/0260303 A1 | 12/2004 | Carrison |
| 6,783,550 | B2 | 8/2004 | MacArthur | 2005/0015153 A1 | 1/2005 | Gobel et al. |
| 6,783,551 | B1 | 8/2004 | Metzger | 2005/0038520 A1 | 2/2005 | Binette et al. |
| 6,802,864 | B2 | 10/2004 | Tornier | 2005/0043805 A1 | 2/2005 | Chudik |
| 6,814,735 | B1 | 11/2004 | Zirngibl | 2005/0043808 A1 | 2/2005 | Felt et al. |
| 6,827,722 | B1 | 12/2004 | Schoenefeld | 2005/0065612 A1 | 3/2005 | Winslow |
| 6,860,902 | B2 | 3/2005 | Reiley | 2005/0075642 A1 | 4/2005 | Felt |
| 6,884,246 | B1 | 4/2005 | Sonnabend et al. | 2005/0143731 A1 | 6/2005 | Justin et al. |
| 6,893,467 | B1 | 5/2005 | Bercovy | 2005/0143745 A1 | 6/2005 | Hodorek et al. |
| 6,923,813 | B2 | 8/2005 | Phillips et al. | 2005/0143831 A1 | 6/2005 | Justin et al. |
| 6,926,739 | B1 | 8/2005 | OConnor | 2005/0154398 A1 | 7/2005 | Miniaci et al. |
| 6,962,577 | B2 | 11/2005 | Tallarida et al. | 2005/0209705 A1 | 9/2005 | Niederauer et al. |
| 6,969,393 | B2 | 11/2005 | Pinczewski et al. | 2005/0229323 A1 | 10/2005 | Mills et al. |
| 6,984,248 | B2 * | 1/2006 | Hyde, Jr. ................ 623/18.12 | 2005/0287187 A1 | 12/2005 | Mansmann |
| 6,989,016 | B2 | 1/2006 | Tallarida et al. | 2006/0004461 A1 | 1/2006 | Justin et al. |
| 7,029,479 | B2 | 4/2006 | Tallarida | 2006/0020343 A1 | 1/2006 | Ek |
| 7,063,717 | B2 | 6/2006 | St. Pierre et al. | 2006/0052878 A1 | 3/2006 | Schmieding |
| 7,115,131 | B2 | 10/2006 | Engh et al. | 2006/0058744 A1 | 3/2006 | Tallarida et al. |

| | | | |
|---|---|---|---|
| 2006/0058883 A1 | 3/2006 | Aram et al. | |
| 2006/0085006 A1 | 4/2006 | Ek | |
| 2006/0149370 A1 | 7/2006 | Schmieding et al. | |
| 2006/0190002 A1 | 8/2006 | Tallarida | |
| 2006/0195112 A1 | 8/2006 | Ek | |
| 2006/0229726 A1 | 10/2006 | Ek | |
| 2007/0005143 A1 | 1/2007 | Ek | |
| 2007/0038307 A1 | 2/2007 | Webster et al. | |
| 2007/0073394 A1 | 3/2007 | Seedhom et al. | |
| 2007/0093842 A1 | 4/2007 | Schmieding | |
| 2007/0093890 A1 | 4/2007 | Eliasen et al. | |
| 2007/0118136 A1 | 5/2007 | Ek | |
| 2007/0123921 A1 | 5/2007 | Ek | |
| 2007/0179608 A1 | 8/2007 | Ek | |
| 2007/0233128 A1 | 10/2007 | Schmieding et al. | |
| 2007/0250067 A1 | 10/2007 | Schmieding et al. | |
| 2007/0255399 A1 | 11/2007 | Eliasen et al. | |
| 2007/0265700 A1 | 11/2007 | Eliasen et al. | |
| 2007/0288031 A1 | 12/2007 | Dreyfuss et al. | |
| 2007/0299519 A1 | 12/2007 | Schmieding | |
| 2008/0004659 A1 | 1/2008 | Burkhart et al. | |
| 2008/0015709 A1 | 1/2008 | Evans et al. | |
| 2008/0027430 A1 | 1/2008 | Montgomery et al. | |
| 2008/0033443 A1 | 2/2008 | Sikora et al. | |
| 2008/0086139 A1 | 4/2008 | Bourke et al. | |
| 2008/0172125 A1 | 7/2008 | Ek | |
| 2008/0183290 A1 | 7/2008 | Baird et al. | |
| 2008/0188935 A1 | 8/2008 | Saylor et al. | |
| 2008/0275512 A1 | 11/2008 | Albertirio et al. | |
| 2008/0306483 A1 | 12/2008 | Iannarone | |
| 2009/0198288 A1 | 8/2009 | Hoof et al. | |
| 2009/0234452 A1 | 9/2009 | Steiner et al. | |

FOREIGN PATENT DOCUMENTS

| | | |
|---|---|---|
| AU | 2003262428 | 8/2009 |
| DE | 2933174 | 4/1980 |
| DE | 3516743 | 11/1986 |
| DE | 3840466 | 6/1990 |
| EP | 0241240 | 10/1987 |
| EP | 0350780 | 7/1989 |
| EP | 0350780 | 1/1990 |
| EP | 0485678 | 5/1992 |
| EP | 0327387 | 9/1992 |
| EP | 0505634 | 9/1992 |
| EP | 0903125 | 3/1999 |
| EP | 0903127 | 3/1999 |
| EP | 0661023 | 8/2001 |
| EP | 1426013 | 9/2004 |
| EP | 1278460 | 4/2009 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003534096 | 11/2003 |
| WO | 8803781 | 6/1988 |
| WO | 8909578 | 10/1989 |
| WO | 9427507 | 12/1994 |
| WO | 9624304 | 8/1996 |
| WO | 9722306 | 6/1997 |
| WO | 9920192 | 4/1999 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2005051231 | 6/2005 |
| WO | 2005512331 | 6/2005 |
| WO | 2006004885 | 1/2006 |
| WO | 2006091686 | 8/2006 |

OTHER PUBLICATIONS

International Search Report and Written Opinion dated Jun. 24, 2008 issued in related International Patent Application No. PCT/US07/73685.

International Search Report and Written Opinion dated Jun. 11, 2008 issued in related International Patent Application No. PCT/US07/25284.

International Search Report and Written Opinion dated Aug. 8, 2008 issued in related International Patent Application No. PCT/US08/53988.

U.S. Office Action issued in related U.S. Appl. No. 10/994,453 dated Jun. 5, 2007.

Japanese Office Action dated Jul. 22, 2008 issued in related Japanese Patent Application No. 2006-501193.

U.S. Office Action issued in related U.S. Appl. No. 10/373,463 dated Apr. 21, 2008.

Notice of Allowance received in U.S. Appl. No. 10/618,887 dated Aug. 15, 2008.

Australia Office Action issued in related Australian Patent Application No. 2007216648 dated May 30, 2008.

European Office Action issued in related European Patent Application No. 01932833.5-2310 dated Apr. 25, 2008.

U.S. Office Action received in related U.S. Appl. No. 11/169,326 dated Jun. 30, 2008.

U.S. Office Action received in related U.S. Appl. No. 11/169,326 dated Jul. 27, 2007.

U.S. Office Action received in related U.S. Appl. No. 11/169,326 dated Apr. 17, 2007.

U.S. Office Action received in related U.S. Appl. No. 11/169,326 dated Mar. 9, 2007.

Canadian Office Action issued in related Canadian Patent Application No. 2546582 dated Aug. 21, 2008.

U.S. Office Action issued in related U.S. Appl. No. 10/994,453 dated Sep. 3, 2008.

International Search Report and Written Opinion dated Apr. 21, 2010 issued in related International Patent Application No. PCT/US2010/025095.

International Search Report and Written Opinion dated May 3, 2010 issued in related International Patent Application No. PCT/US2010/025464.

European Office Action dated Apr. 13, 2010 issued in related European Patent Application No. 02805182.9-2310.

European Office Action dated Mar. 25, 2010 issued in related European Patent Application No. 01997077.1-2310.

U.S. Office Action dated May 18, 2010 issued in related U.S. Appl. No. 12/415,503.

U.S. Office Action dated Oct. 21, 2008 issued in related U.S. Appl. No. 11/461,240.

U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung," (dated unknown).
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 18, 2009 issued in related U.S. Appl. No. 11/209,170.
U.S. Office Action dated May 28, 2009 issued in related U.S. Appl. No. 11/359,891.
U.S. Office Action dated May 13, 2009 issued in related U.S. Appl. No. 11/359,892.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
Notice of Reasons for Rejection dated Nov. 17, 2009 issued in Japanese Patent Application No. 2007-519417.
European Search Report dated Dec. 3, 2009 issued in related European Patent Application No. 06735827.5.
European Office Action dated Jan. 11, 2010 issued in related European Patent Application No. 2005218302.
U.S. Office Action dated Jan. 25, 2010 issued in related U.S. Appl. No. 11/326,133.
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office action dated Feb. 26, 2009 in related European Patent Application No. 05791453.3.
International Preliminary Report on Patentability dated Aug. 20, 2009 issued in related International Patent Application No. 2008053194.
Notice of Allowance dated Aug. 25, 2009 issued in related U.S. Appl. No. 11/379,151.
Notice of Allowance dated Aug. 27, 2009 issued in related U.S. Appl. No. 10/760,965.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.

Office Action issued in corresponding U.S. Appl. No. 11/326,133 dated Oct. 17, 2007.

Office Action issued in corresponding U.S. Appl. No. 10/741,044 dated Oct. 26, 2005.

McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).

Bushnell, et al., "Bony Instability of the Shoulder," Arthroscopy, The Journal of Arthroscopic and related Surgery, vol. 24, No. 9; Sep. 2005 (pp. 1061-1073).

Scalise, et al., "Resurfacing Arthroplasty of the Humerus: Indications, Surgical Technique, and Clinical Results," Techniques in Shoulder and Elbow Surgery 8(3):152-160; 2007.

Davidson, et al., "Focal Anatomic Patellofemoral Inlay Resurfacing: Theoretic Basis, Surgical Technique, and Case Reports," Orthop. Clin. N. Am., 39 (2008) pp. 337-346.

Provencher, et al., "Patellofemoral Kinematics After Limited Resurfacing of the Trochlea," The Journal of Knee Surgery, vol. 22 No. 2 (2008) pp. 1-7.

Dawson, et al., "The Management of Localized Articular Cartilage Lesions of the Humeral Head in the Athlete," Operative Techniques in Sports Medicine, vol. 16, Issue 1, pp. 14-20 (2008).

Uribe, et al., "Partial Humeral Head Resurfacing for Osteonecrosis," Journal of Shoulder and Elbow Surgery, (2009) 6 pages.

Burks, "Implant Arthroplasty of the First Metatarsalphalangeal Joint," Clin. Podiatr. Med. Surg., 23 (2006) pp. 725-731.

Hasselman, et al., "Resurfacing of the First Metatarsal Head in the Treatment of Hallux Rigidus," Techniques in Foot & Ankle Surgery 7(1):31-40, 2008.

Gelenkoberflachen, et al., "Partial hemi-resurfacing of the hip joint—a new approach to treat local osteochondral defects?" Biomed Tech 2006; 51:371-376 (2006).

Sullivan, "Hallux Rigidus: MTP Implant Arthroplasty," Foot Ankle Clin. N. Am. 14 (2009) pp. 33-42.

Cook, et al., "Meta-analysis of First Metatarsophalangeal Joint Implant Arthroplasty," Journal of Foot and Ankle Surgery, vol. 48, Issue 2, pp. 180-190 (2009).

Derner, "Complications and Salvage of Elective Central Metatarsal Osteotomies," Clin. Podiatr. Med. Surg. 26 (2009) 23-35.

Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.

Beecher, et al. "Effects of a contoured articular prosthetic device on tibiofemoral peak contact pressure: a biomechanical study," Knee Surg Sports Traumatol Arthrosc. Jan. 2008; 16(1): 56-63.

United States Office Action dated May 13, 2009 issued in related U.S. Appl. No. 11/359,892.

United States Office Action dated May 18, 2009 issued in related U.S. Appl. No. 11/209,170.

United States Office Action dated May 1, 2009 issued in related U.S. Appl. No. 11/461,240.

Australian Office Action dated Jan. 29, 2009 issued in related Australian Patent Application No. 2004216106.

European Search Report dated Apr. 22, 2009 issued in related European Patent Application No. 09002088.4.

Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).

Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.

Chainsaw, Wikipedia, the free encyclopedia, http://en.wikipedia.org/w/index.php?title=Chainsaw&printable=yes, Jun. 26, 2007 (3 pages).

APTA | Knee,/http://www.apta.org/AM/PrinerTemplate.cfm?Section=Home&Template=/CM/HTMLDisplay.dfg&... Jun. 25, 2007 (1page).

American Machinist, Full-radius milling cutters, http://www.americanmachinist.com/Classes/Article/ArticleDraw_P.aspx, Jun. 26, 2007 (1 page).

Chuck (engineering),Wikipedia, the free encyclopedia, http://en.wikipedia.org/w/index.php?title=Chuck_%28engineering%29&printable=yes, Jun. 25, 2007, (4 pages).

Dovetail Rails, http://www.siskiyou.com/MDRSeries.htm, Jun. 25, 2007 (2 pages).

Knee Resurfacing, Permedica, GKS, Global Knee System. Cod. 104570 vers 1.0 del Mar. 15, 2006 (8pages).

Makita Industrial Power Tools, Product Details Print Out, Chain Mortiser, http://www.makita.com/menu.php?pg=product_det_prn& tag=7104L, Jun. 26, 2007 (3pgs).

Milling machine, Wikipedia, the free encyclopedia, http://en.wikipedia.org/w/index.php?title=Milling_machine&printable=yes, Jun. 26, 2007 (4 pages).

Mortise and tenon, Wikipedia, the free encyclopedia, http://en.wikipedia.org/w/index.php?title=Mortise_and_tenon&printable=yes, Jun. 25, 2007 (3 pages).

Oka et al, "Development of artificial articular cartilage", Proc Instn Mech Engrs vol. 214 Part H, 2000 pp. 59-68 (10 pages).

M. Siguier, MD et al, "Preliminary Results of Partial Surface Replacement of the Femoral Head in Osteonecrosis", The Jorunal of Arthroplasty, vol. 14, No. 1, 1999, pp. 45-51.

T. Siguier, MD et al, Partial Resurfacing Arthroplasty of the Femoral Head in Avascular Necrosis, Clinical Orthopaedics and Related Research, No. 386, 2001, pp. 85-92.

Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).

The Mini Uni: A New Solution for Arthritic Knew Pain and Disability, AORI, 4 pages, www.aori.org/uniknee.htm Apr. 20, 2004.

The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.

Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).

Russell E. Windsor, MD, In-Depth Topic Reviews, Unicompartmental Knee Replacement, Nov. 7, 2002, 9 pages.

Yaw angle, Wikipedia, the free encyclopedia, http://en.wikipedia.org/w/index.php?title=Yaw_angle&printable=yes, Jun. 25, 2007 (1 page).

Bale, MD, Reto J., et al, "Osteochondral Lesions of the Talus: Computer=assisted Retrograde Drilling Feasibility and Accuracy in Initial Experriences[1]", (Radiology. 2001;218:278-282) © RSNA, 2001.

Biomet/Copeland, "Aequalis® Resurfacing Head" Tornier, Scientific Vision, Surgical Leadership, SS-401 Jan. 2007.

Kumai, M.D., Tsukasa, et al Arthroscopic Drilling for the Treatment of Osteochondral Lesions of the Talus*, The Journal of Bone & Joint Surgery, American vol. 81:1229-35(1999).

Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 Jul.-Aug. 2001:pp. 653-659.

Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.

Schneider, T., et al, "Arthroscopy of the ankle joint. A list of indications and realistic expectations", Foot and Ankle Surgery 1996 2:189-193, © 1996 Arnette Blackwell SA.

Taranow WS, et al, "Retrograde drilling of osteochondral lesions of the medial talar dome", PubMed, www.pubmed.gov, A service of the National Library of Medicine and the Natinal Institutes of Health, Foot Ankle Int.Aug. 1999; 20 (8):474-80.

Ueblacker, M.D., Peter, et al, "Retrograde Cartilage Transplantation of the Proximal and Distal Tibia", Arthroscopy: The Journal of Arthroscipic and Related Surgery, vol. 20, No. 1 Jan. 2004: pp. 73-78.

USPTO Office Action dated Dec. 21, 2007 issued in corresponding U.S. Appl. No. 11/169,326.

USPTO Office Action dated Dec. 26, 2007 issued in U.S. Appl. No. 11/379,151.

USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Aug. 19, 2004 issued in corresponding PCT patent application No. PCT/US02/40310.
International Preliminary Examination Report dated Nov. 5, 2002 issued in corresponding PCT patent application No. PCT/US01/14061.
US Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
International Preliminary Report on Patentability dated Aug. 20, 2009 issued in related International Patent Application No. PCT/US2008/053194.
Australian Notice of Allowance dated Oct. 29, 2009 issued in related Australian Patent Application No. 2007216648.
Notice of Allowance dated Aug. 27, 2009 issued in related U.S. Appl. No. 10/760,965.
Notice of Allowance dated Oct. 9, 2009 issued in related U.S. Appl. No. 10/373,463.
Australian Office Action dated Oct. 29, 2009 issued in related Australian Patent Application No. 2007203623.
Notice of Allowance dated Aug. 25, 2009 issued in related U.S. Appl. No. 11/379,151.
Japanese Notice of Reasons for Rejection dated Sep. 8, 2009 issued in related Japanese Patent Application No. 2003552147.

Supplemental Notice of Allowance dated Nov. 25, 2009 issued in related U.S. Appl. No. 10/373,463.
Office Action dated Dec. 24, 2009 issued in related U.S. Appl. No. 10/994,453.
Office Action dated Sep. 2, 2010 issued in related U.S. Appl. No. 12/415,503.
Notice of Allowance dated Aug. 6, 2010 issued in related U.S. Appl. No. 11/359,892.
Office Action dated Jul. 21, 2010 issued in related U.S. Appl. No. 11/551,912.
Office Action dated Aug. 5, 2010 issued in related U.S. Appl. No. 11/325,133.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
International Preliminary Report on Patentability dated Sep. 16, 2010 issued in related International Patent Application No. PCT/US2009/035889.
Office Action dated Oct. 11, 2010 issued in related Australian Patent Application No. 2006216725.
European Search Report dated Nov. 4, 2010 issued in related European Patent Application No. 07862736.1-1269.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.

* cited by examiner

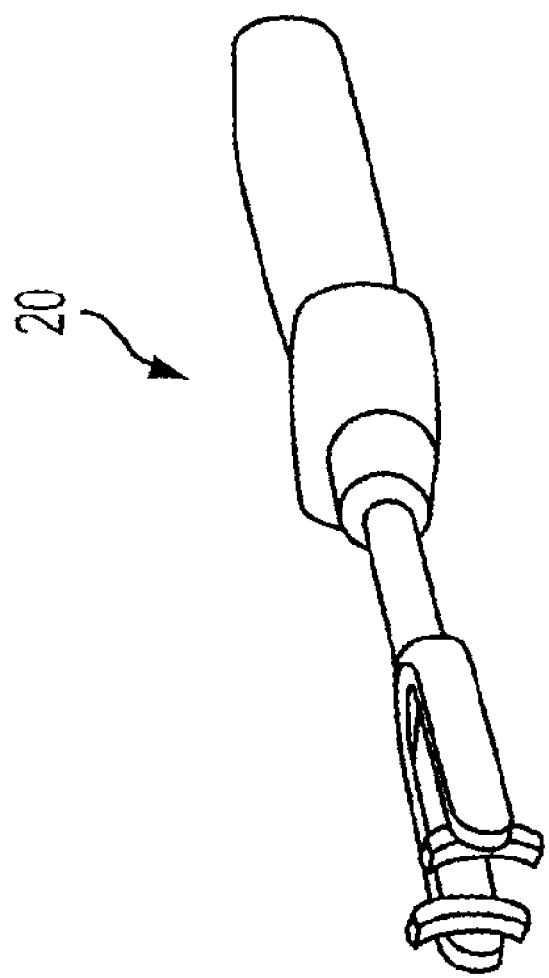
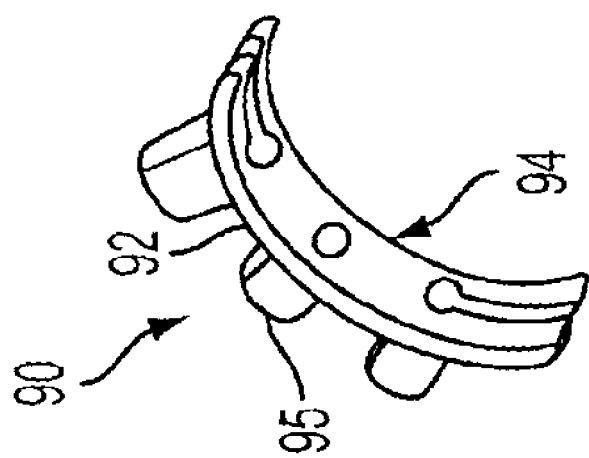
FIG. 12

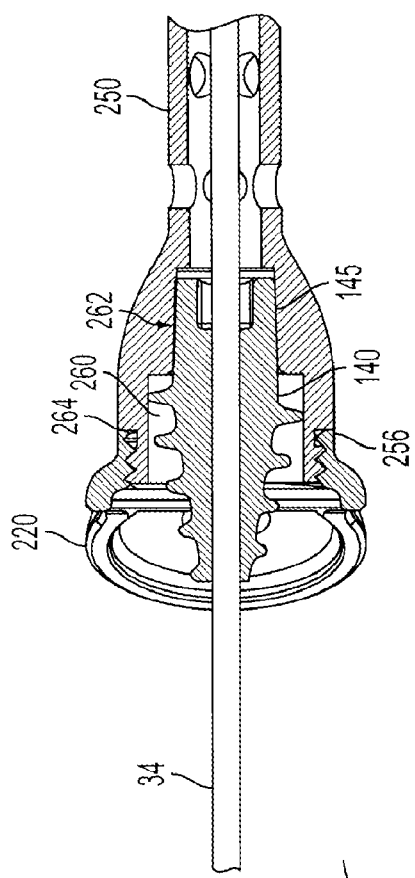
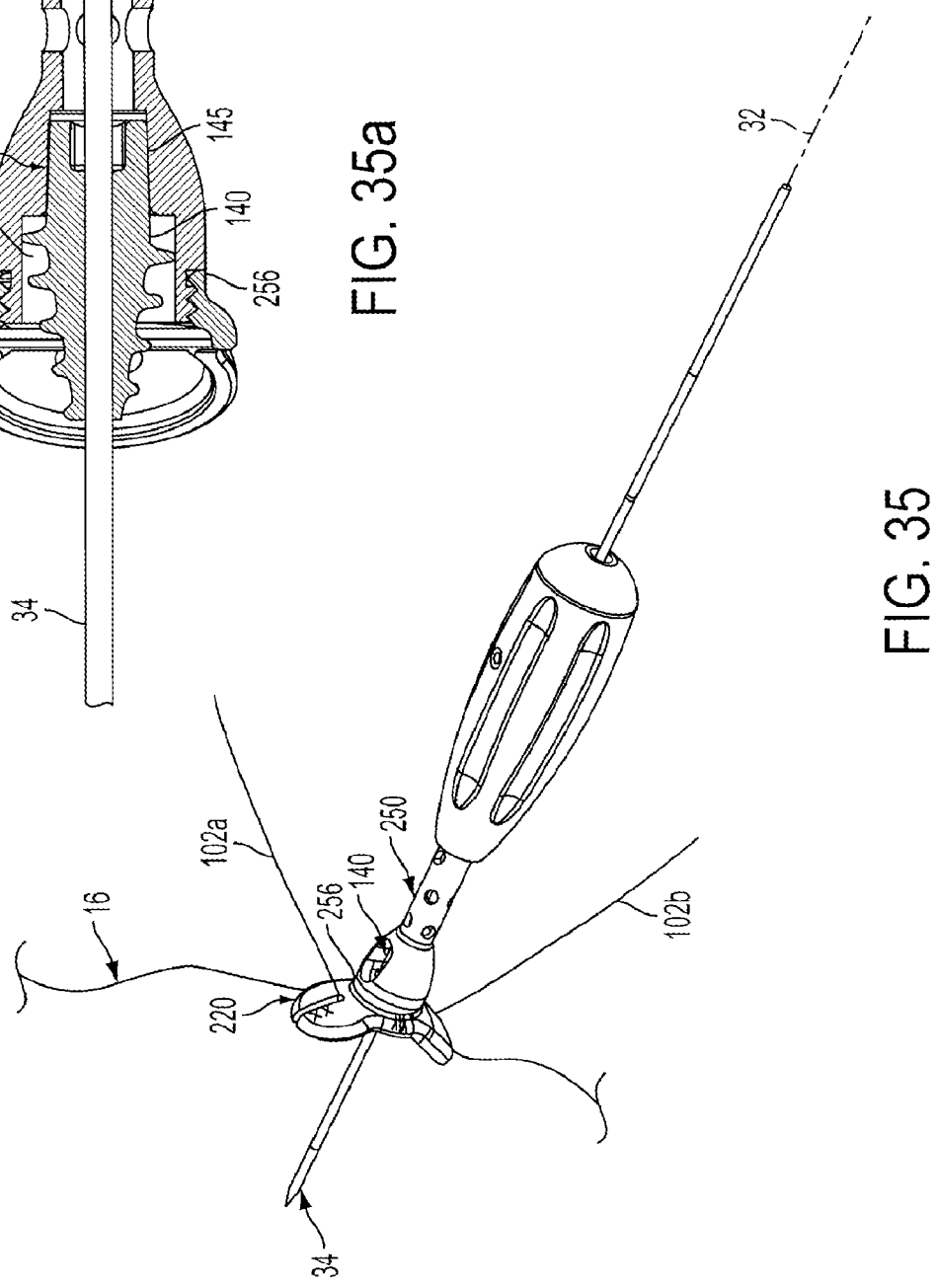
FIG. 35a
FIG. 35

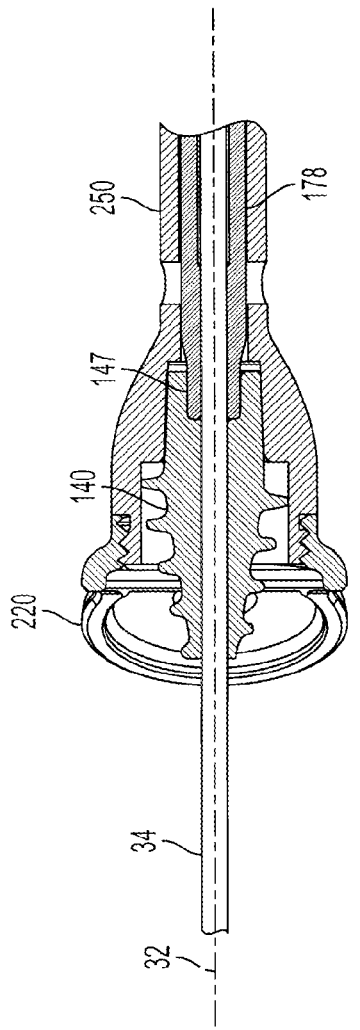
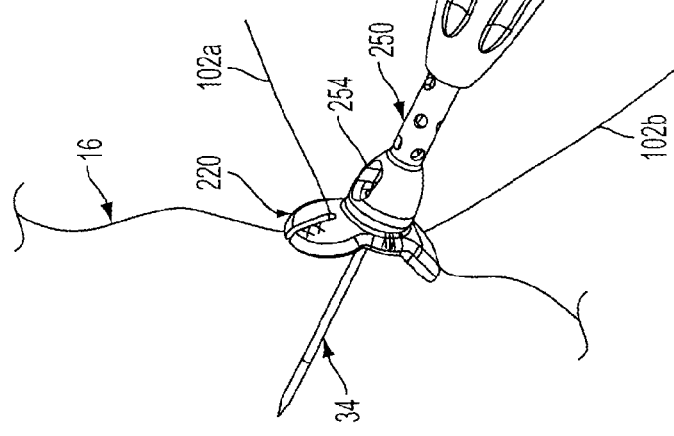
FIG. 36a
FIG. 36

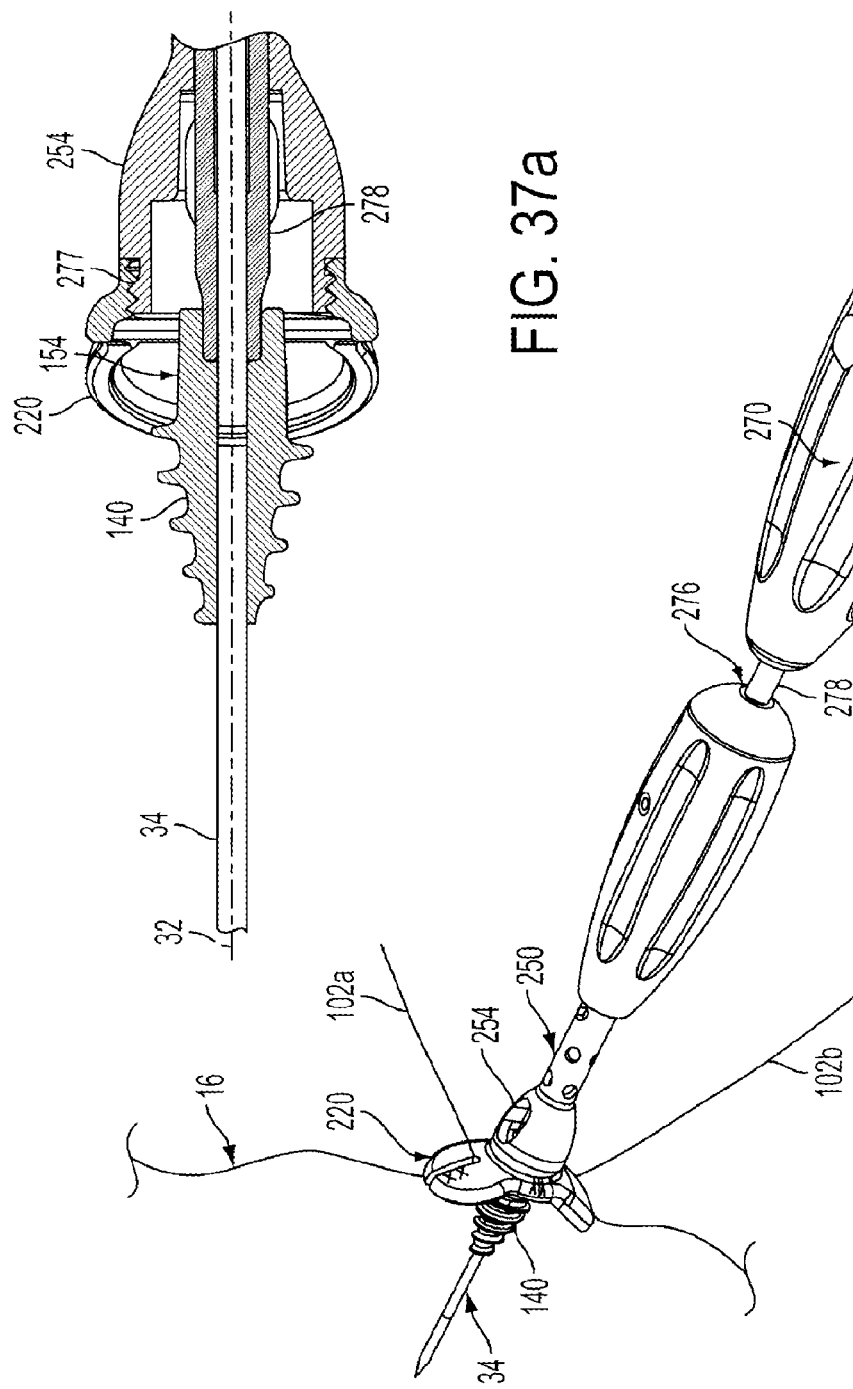
FIG. 37
FIG. 37a

BONE RESURFACING SYSTEM AND METHOD

CROSS REFERENCE TO RELATED APPLICATIONS

This application is a continuation-in-part of U.S. patent application Ser. No. 12/027,121 filed Feb. 6, 2008, which claims the benefit of U.S. provisional patent application Ser. No. 60/888,382, filed Feb. 6, 2007 and which is itself a continuation-in-part of U.S. patent application Ser. No. 11/359,891, filed Feb. 22, 2006, which itself is a continuation-in-part of U.S. patent application Ser. No. 10/373,463, filed Feb. 24, 2003, which is a continuation-in-part application of application Ser. No. 10/162,533 (now U.S. Pat. No. 6,679,917), filed Jun. 4, 2002, which is itself a continuation-in-part application of application Ser. No. 10/024,077 (now U.S. Pat. No. 6,610,067), filed Dec. 17, 2001, which is itself a continuation-in-part application of application Ser. No. 09/846,657 (now U.S. Pat. No. 6,520,964), filed May 1, 2001, which claims the benefit of U.S. provisional application Ser. No. 60/201,049, filed May 1, 2000. This application is also a continuation-in-part of U.S. patent application Ser. No. 11/169,326, filed Jun. 28, 2005 (which claims the benefit of U.S. provisional patent application Ser. No. 60/583,549, filed Jun. 28, 2004) which is also a continuation-in-part of U.S. patent application Ser. No. 10/994,453, filed Nov. 22, 2004 (which claims the benefit of U.S. provisional patent application Ser. No. 60/523,810, filed Nov. 20, 2003), which is also a continuation-in-part of U.S. patent application Ser. No. 10/308,718, filed Dec. 3, 2002. This application also claims the benefit of U.S. Provisional Application Ser. No. 61/033,136, filed Mar. 3, 2008. The entire disclosures of all of which applications and/or patents are incorporated herein by reference.

FIELD

This disclosure relates to devices and methods for the repair of bone surfaces, and particularly to bony articulating joint surfaces.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF THE DRAWINGS

Features and advantages of the present invention are set forth by description of embodiments consistent with the present invention, which description should be considered in conjunction with the accompanying drawings wherein:

FIG. 7a is an enlarged view of measuring indicia of the contract probe of FIG. 7;
FIG. 12 is a perspective view of a guide block and a drill guide;
FIG. 17a is an enlarged view of the shoulder/stop of the reamer of FIG. 17;
FIG. 35 is a plan view of a guide handle assembly of FIG. 34;
FIG. 35a is an enlarged cross-sectional view of the guide handle assembly of FIG. 35;
FIG. 36 is a perspective view of the guide handle assembly of FIG. 34 and a driver;

FIG. 36a is an enlarged cross-sectional view of the guide handle assembly and the driver of FIG. 36;

FIG. 37 depicts the tapered post being advanced along the guide pin;

FIG. 37a is an enlarged cross-sectional view of FIG. 37;

DETAILED DESCRIPTION

As an overview, the present disclosure is directed to systems and methods for bone resurfacing and for preparing an implant site to resurface bone. While the following detailed description will proceed with reference to resurfacing the femoral condyle of the knee joint, the concepts, methodologies and systems described herein may be applied to any bony surface, for example, articulating joints of the ankle, hip and/or shoulder. In at least one embodiment, the present disclosure may feature a system and method for resurfacing at least a portion of an articular surface having a defect by replacing a portion of the articular surface with an implant. The implant may comprise a load bearing surface having a contour and/or shape substantially corresponding to the patient's original articular surface about the defect site which may be configured to engage an adjacent articular surface. The present disclosure will describe a system and method for replacing a portion of the articular surface of the femoral condyle; however, it should be understood that the system and method according to the present disclosure may also be used to resurface articular surfaces other than the femoral condyle.

As an initial matter, many of the devices described herein comprise cannulated components configured to be arranged over other components. The degree to which the cannulated passageway (i.e., internal diameter of the passageway/cavity) of a first component corresponds to the external diameter of the component over which it is being placed may be close enough to generally eliminate excessive movement. Excessive movement may be defined as an amount of movement that may result in misalignment of the implant relative to the articular surface.

Figure 1:
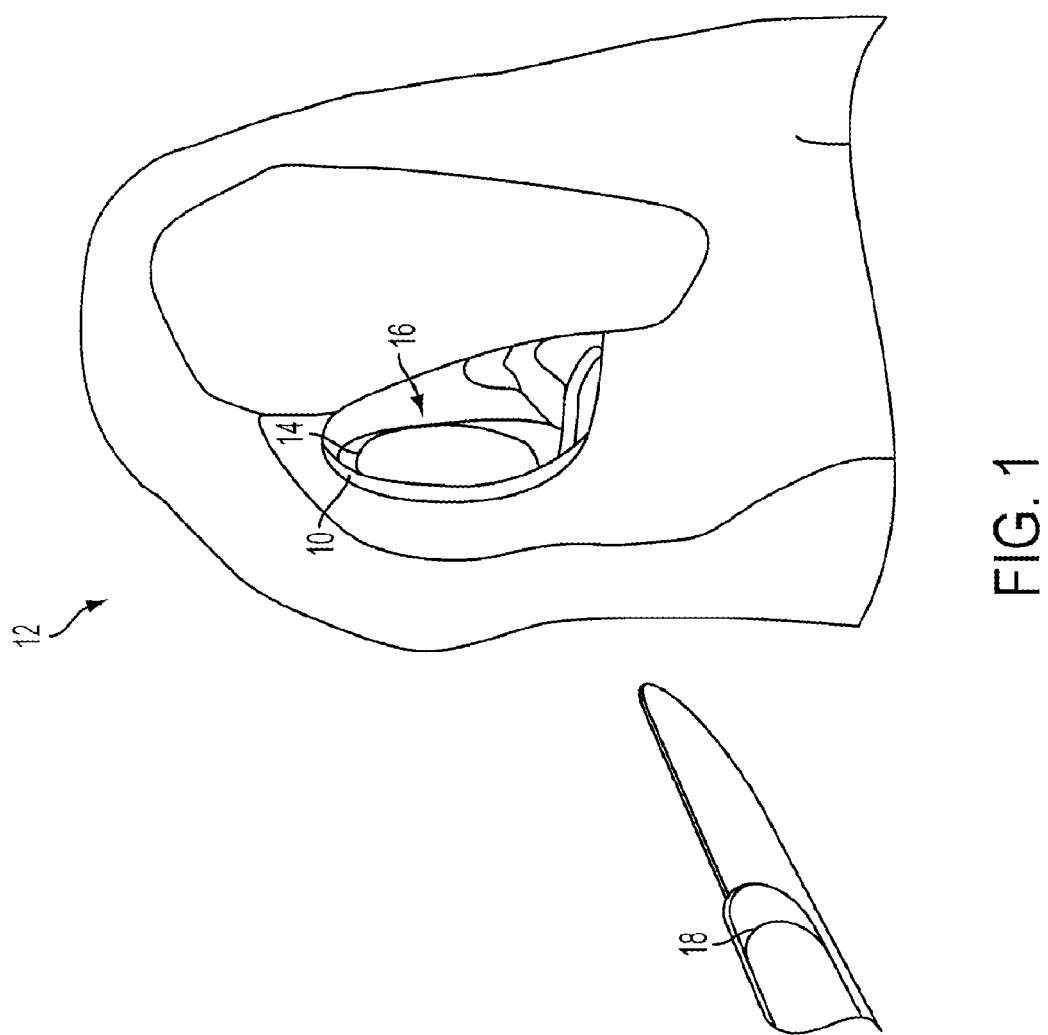
FIG. 1 is a plain view illustrating an excision.
Figure 2:
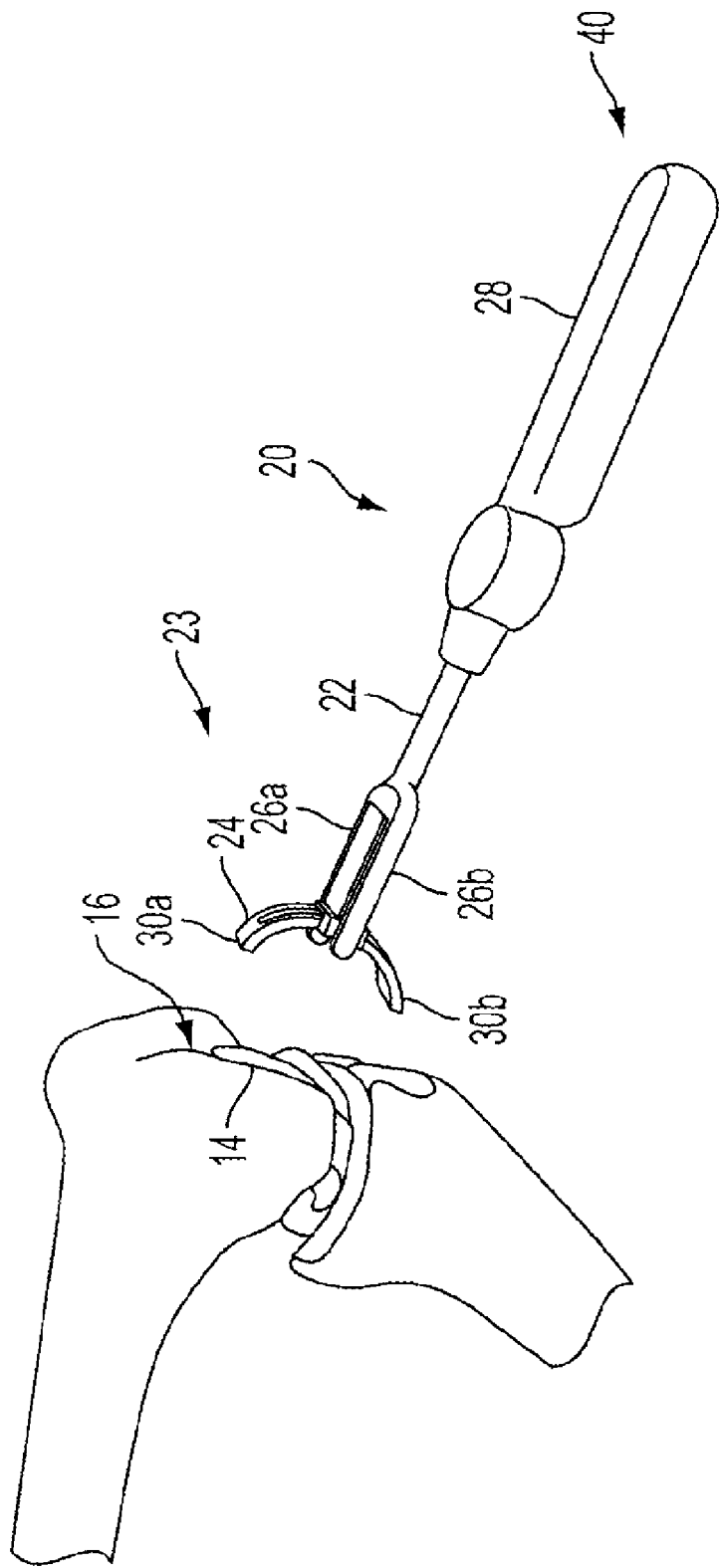
FIG. 2 is a plain view of a drill guide and a tip.

Referring now to FIG. 1, an incision 10 may be created proximate the patient's knee 12 to provide access to the defect 14 on the patient's articular surface 16, for example, using a scalpel 18 or the like. Once the incision 10 is created, a drill guide 20, FIG. 2, may be advanced against the articular surface 16. The drill guide 20 may include a cannulated shaft 22, a proximal end 23 comprising an AP arcuate shaped tip 24 and a first and a second ML prong 26a, 26b, and optionally a handle 28. The AP arcuate shaped tip 24 may include two ends 30a, 30b which may be generally aligned in a first plane and the ML two prongs 26a, 26b may be arranged in a second plane. These two planes may be configured to be substantially perpendicular to each other as shown. In addition, the AP arcuate shaped tip 24 and the two ML prongs 26a, 26b may be both coupled to the shaft 22 of the drill guide 20 and moveable with respect to each other by way of a biasing device (not shown) such as a spring or the like.

Figure 3:
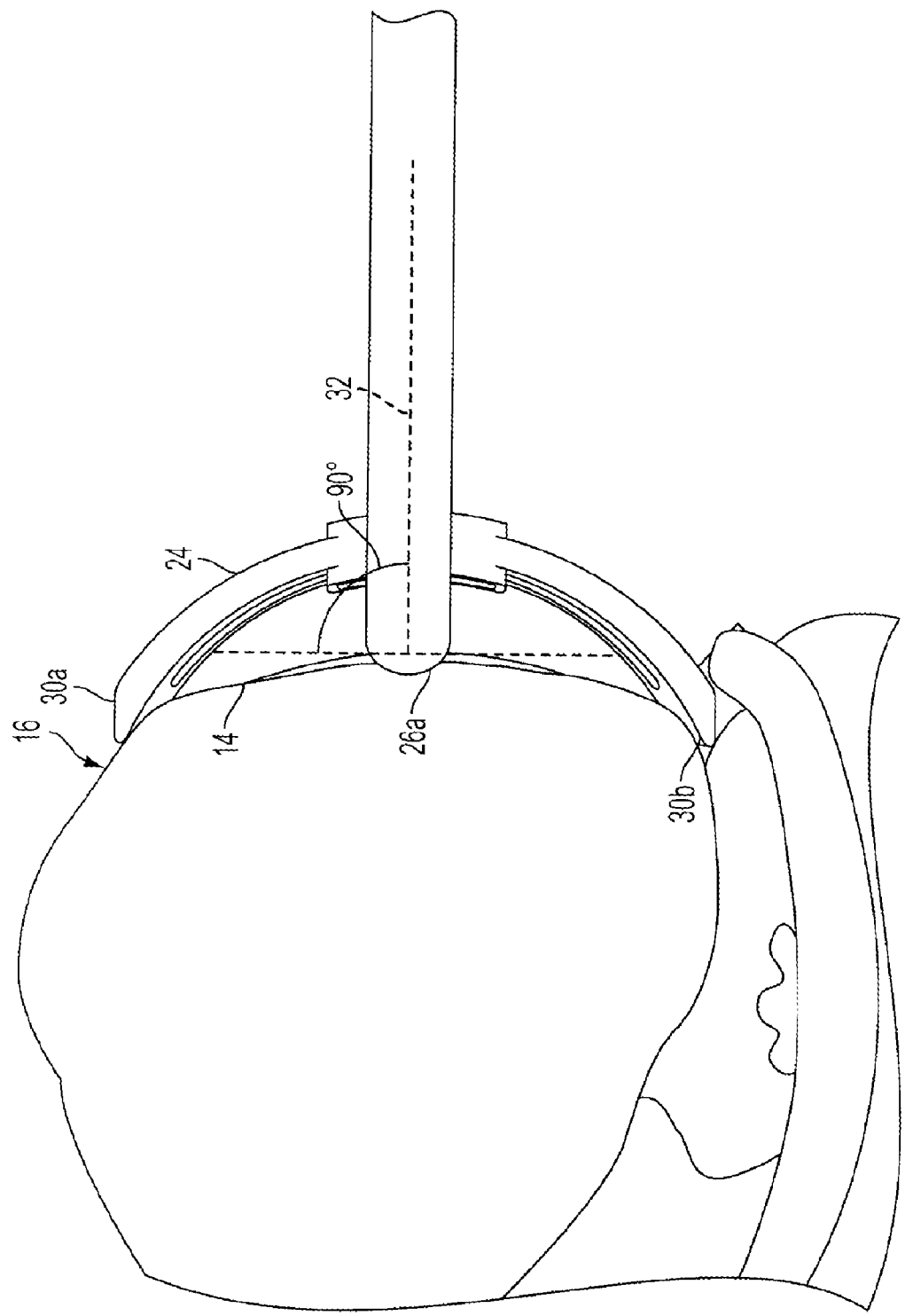
FIG. 3 is a side view of the drill guide of FIG. 2 disposed about the articular surface.

Turning now to FIG. 3, because the AP arcuate shaped tip 24 and the two ML prongs 26a, 26b are moveable with respect to each other, the drill guide 20 may be advanced against the articular surface 16 until the ends 30a, 30b of the AP arcuate shaped tip 24 contact the articular surface 16 generally along the anterior-posterior (AP) plane of the articular surface 16 and the two ML prongs 26a, 26b contact the articular surface 16 generally along the medial-lateral (ML) plane of the articular surface 16. The four points of contact (i.e., ends 30a, 30b and prongs 26a, 26b) of the drill guide 20 may be proximate, but generally not within, the defect site 14 and may be used to establish a reference axis 32 (or first working axis 32) extending from the bone. In one embodiment, the reference axis may extend generally approximately normal to the articular surface 16 about the defect site 14, however, in other embodiments reference axis may extend from the bone but not necessarily normal to the bone.

Figure 4:
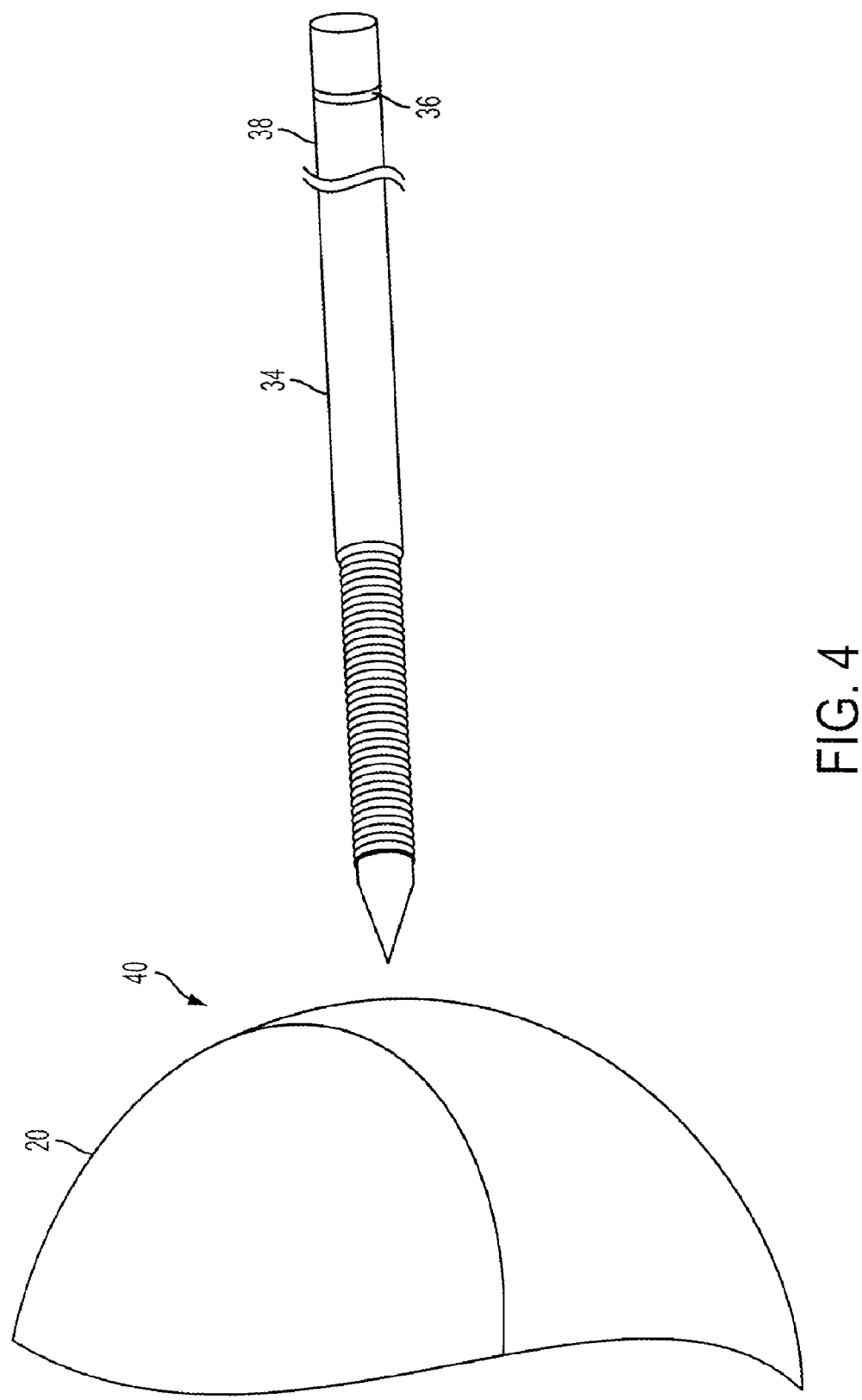
FIG. 4 is a side view of a pin and the drill guide of FIG. 2.

Turning now to FIG. 4, with the four points of the drill guide 20 against the articular surface, a threaded guide pin 34 may be advanced through the cannulated drill guide 20 along the reference axis 32 and into the bone beneath the defect site 14, for example using a drill or the like. To that end, arcuate shaped tip 24 of the drill guide 20 may also include a bore or passageway aligned with the lumen in the cannulated handle. The guide pin 34 may include one or more indicia 36 (for example, but not limited to, laser markings or the like) on the shaft 38 of the guide pin 34 that may be used to control the depth of the guide pin 34 into the bone. By way of example, the indicia 36 on the guide pin 34 may be set relative to the length of the drill guide 20 such that the depth of the guide pin 34 is set when the indicia 36 is aligned with the distal end 40 of the drill guide 20 (i.e., the end opposite the AP arcuate shaped tip 24 and the ML prongs 26a, 26b). Once the guide pin 34 is coupled to the bone, the drill and the drill guide 20 may be removed leaving just the guide pin 34 coupled to the bone and extending along the reference axis 32 (i.e., substantially normal to the original articular surface about the defect site 14). It should be noted that the cannulated passageway of the drill guide 20 may have an internal diameter substantially corresponding to the outer diameter of the guide pin 34.

Figure 5:
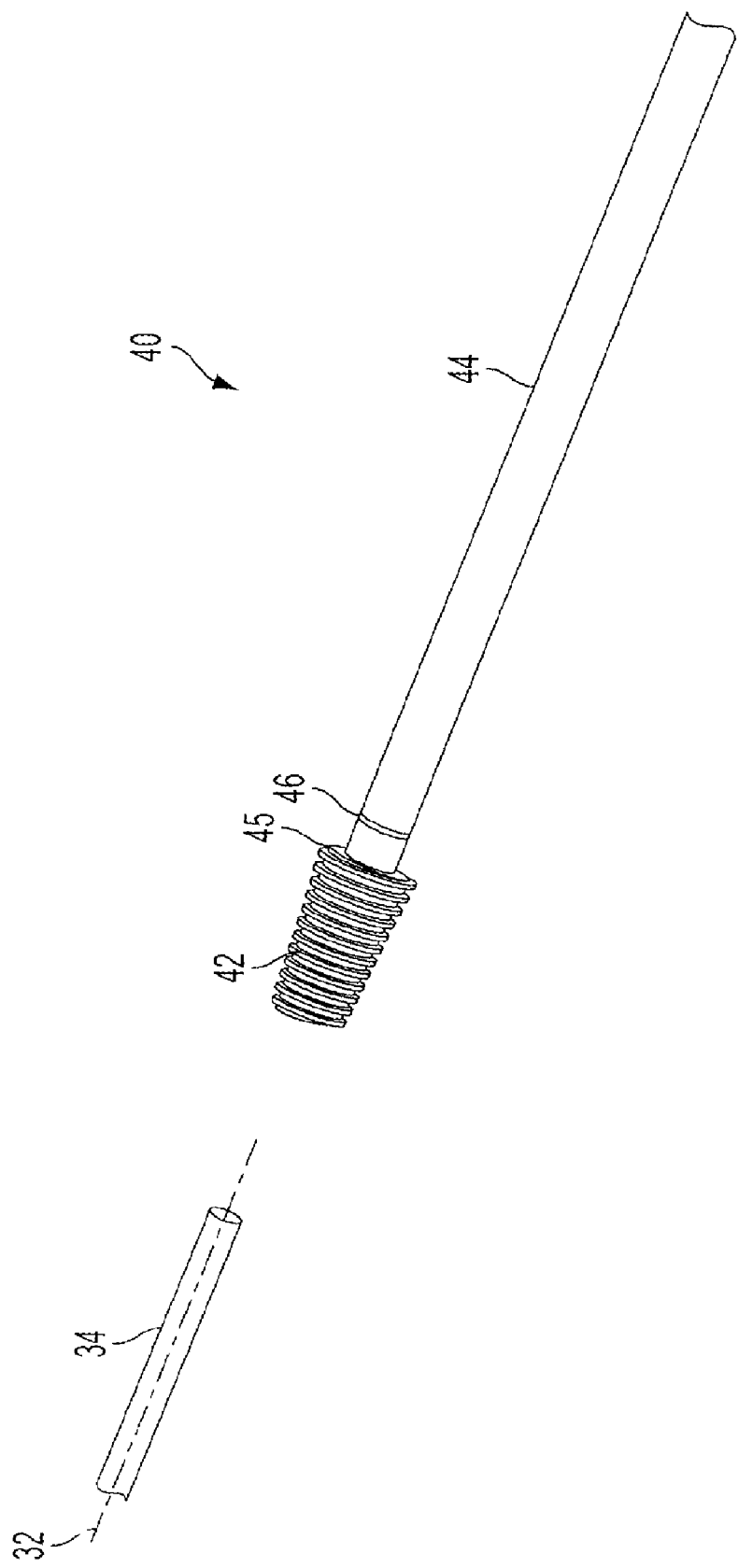
FIG. 5 is a plan view of centering shaft and the pin of FIG. 4.
Figure 6:
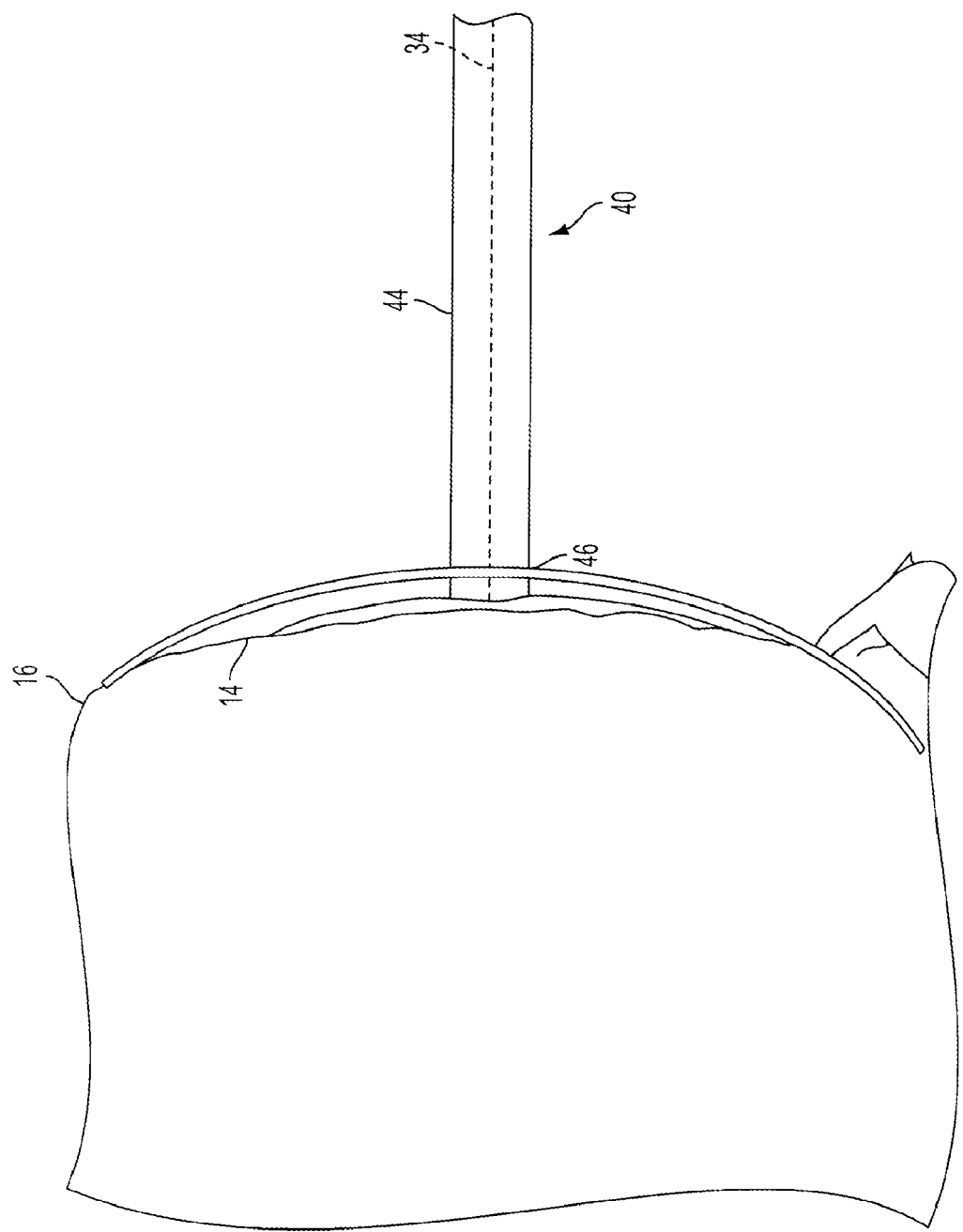
FIG. 6 is a side view of the centering shaft of FIG. 5 and the pin of FIG. 4 disposed about the articular surface.

Turning now to FIG. 5, a centering shaft 40 may be advanced over the guide pin 34. The centering shaft 40 may be cannulated and may comprise a tap 42 at a first end of the cannulated shaft 44. At least a portion of the tap 42 (for example, a portion proximate the first end of the cannulated shaft 44) may extend radially outwardly beyond the outer surface of the cannulated shaft 44 to form a shoulder or abutting surface 45. The centering shaft 40 may be advanced into the bone until a marking 46 (such as, but not limited to, a laser marking or the like) is substantially flush with the original articular surface 16 over the defect site 14 as generally shown in FIG. 6. As may be appreciated, the alignment of the marking 46 with the original articular surface 16 of the defect site 14 may have to be estimated. In addition, it should be noted that the marking 46 may not be aligned to be flush with the actual defect site 14.

Figure 7:
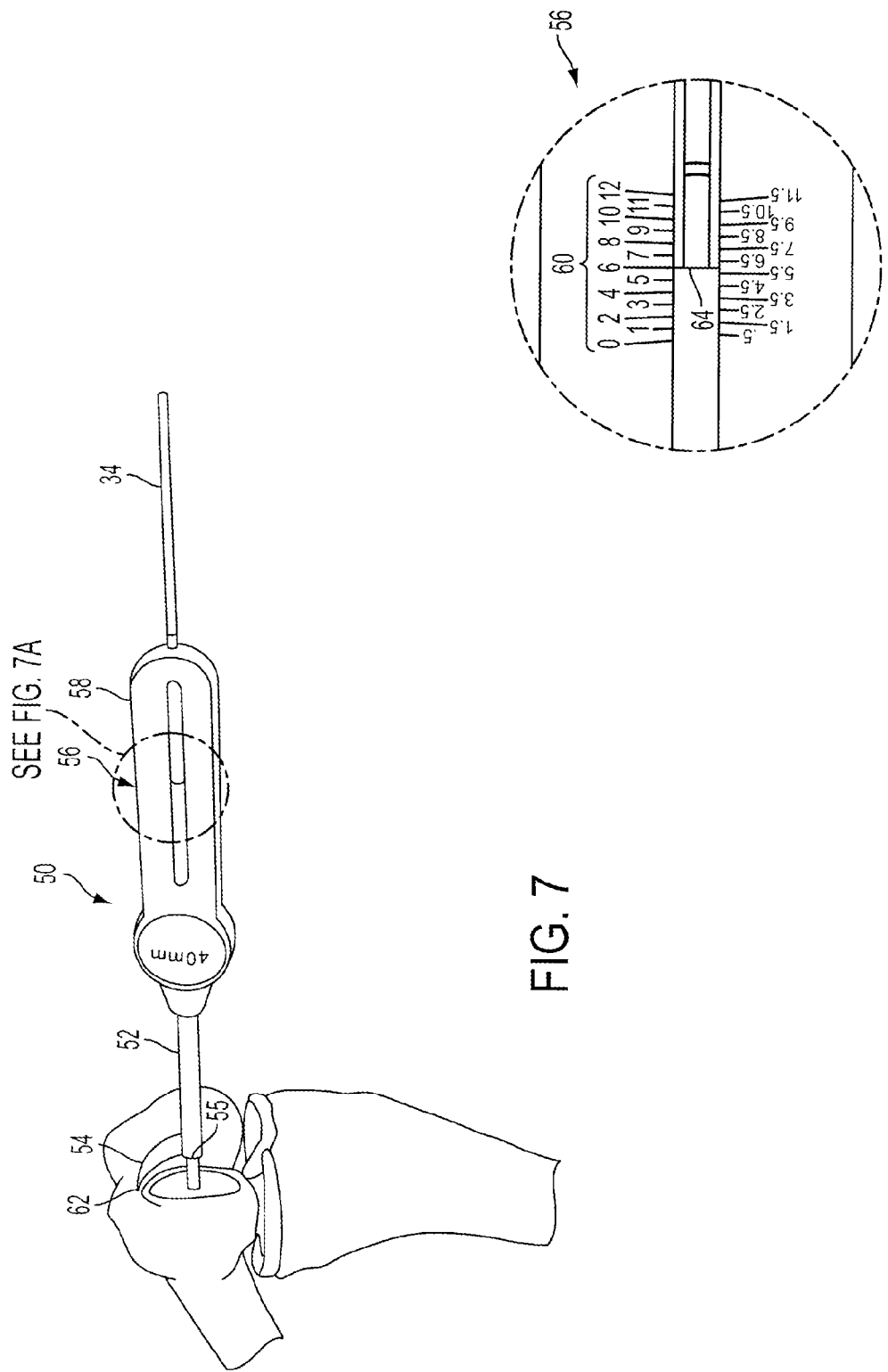
FIG. 7 is a plan view of a contract probe, the centering shaft of FIG. 5, and the pin of FIG. 4.

Next, measurements of the patient's articular surface may be taken in order to determine the appropriate contour of the implant. Referring to FIG. 7, one or more contact probes 50 may be advanced over the centering shaft 40 and/or the guide pin 34. The contact probe 50 may comprise a cannulated shaft 52 and an outrigger 54 extending radially outwardly and axially outwardly from a distal end 55 of the cannulated shaft 52. A first and a second contact probe 50a, 50b may be provide having outriggers 54 extending radially outwardly at a distance of 40 mm and 20 mm, respectively. Of course, other distances are also possible depending on the size of the implant to be delivered as well as the geometry of the defect site 14 and/or the articular surface 16.

The contact probe 50 may also include measuring indicia 56, which may optionally be disposed in a portion of a handle 58. A close up of one embodiment of the measuring indicia 56 is shown in FIG. 7a. The measuring indicia 56 may include a plurality of measurement markings 60 indicating relative distances. In use, the contact probe 50 may be placed over the centering shaft 40 such that the distal end 62 of the outrigger 54 contacts the articular surface 16. A measurement may be taken by based on the alignment of at least one marking on the centering shaft 40 (for example, the second end 64 of the centering shaft) with the plurality of measurement markings 60.

Figure 8:
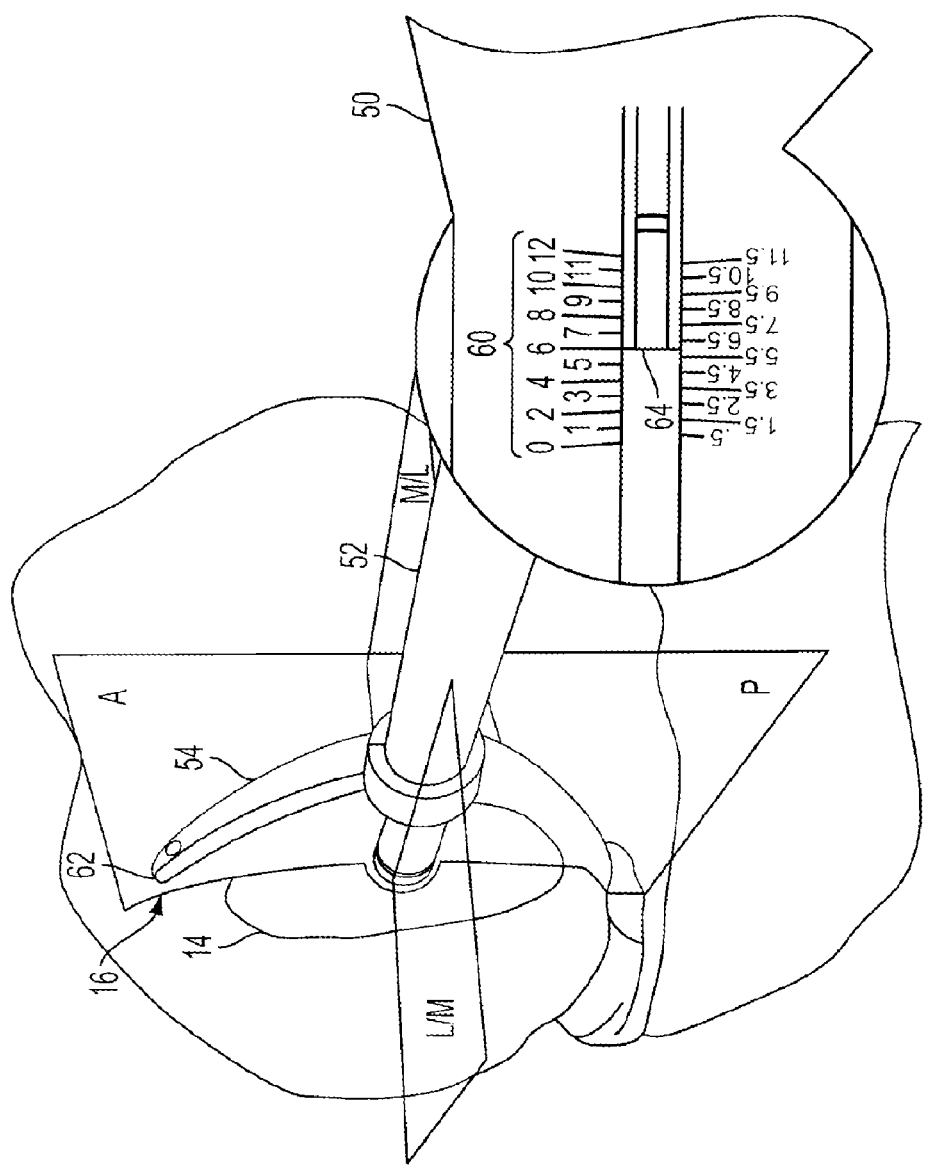
FIG. 8 depicts measurements taken along the anterior-posterior (AP) plane and the medial-lateral (ML) plane using the contact probe of FIG. 7.

Turning now to FIG. 8, a first (and optionally a second) measurement of the patient's articular surface 16 proximate the defect site 14 may be taken along the AP plane using the first contact probe 50a by placing the distal end 62 of the 40 mm outrigger 54 against the patient's articular surface 16. In addition, a first (and optionally a second) measurement of the patient's articular surface 16 proximate the defect site 14 may be taken along the ML plane using the second contact probe 50b by placing the distal end 62 of the 20 mm outrigger 54 against the patient's articular surface 16. The size of the outriggers 54 may be selected based on the size of the defect site 14 such that the distal end 62 of the outrigger 54 contacts the articular surface 16 and not the defect site 14.

Figure 9:
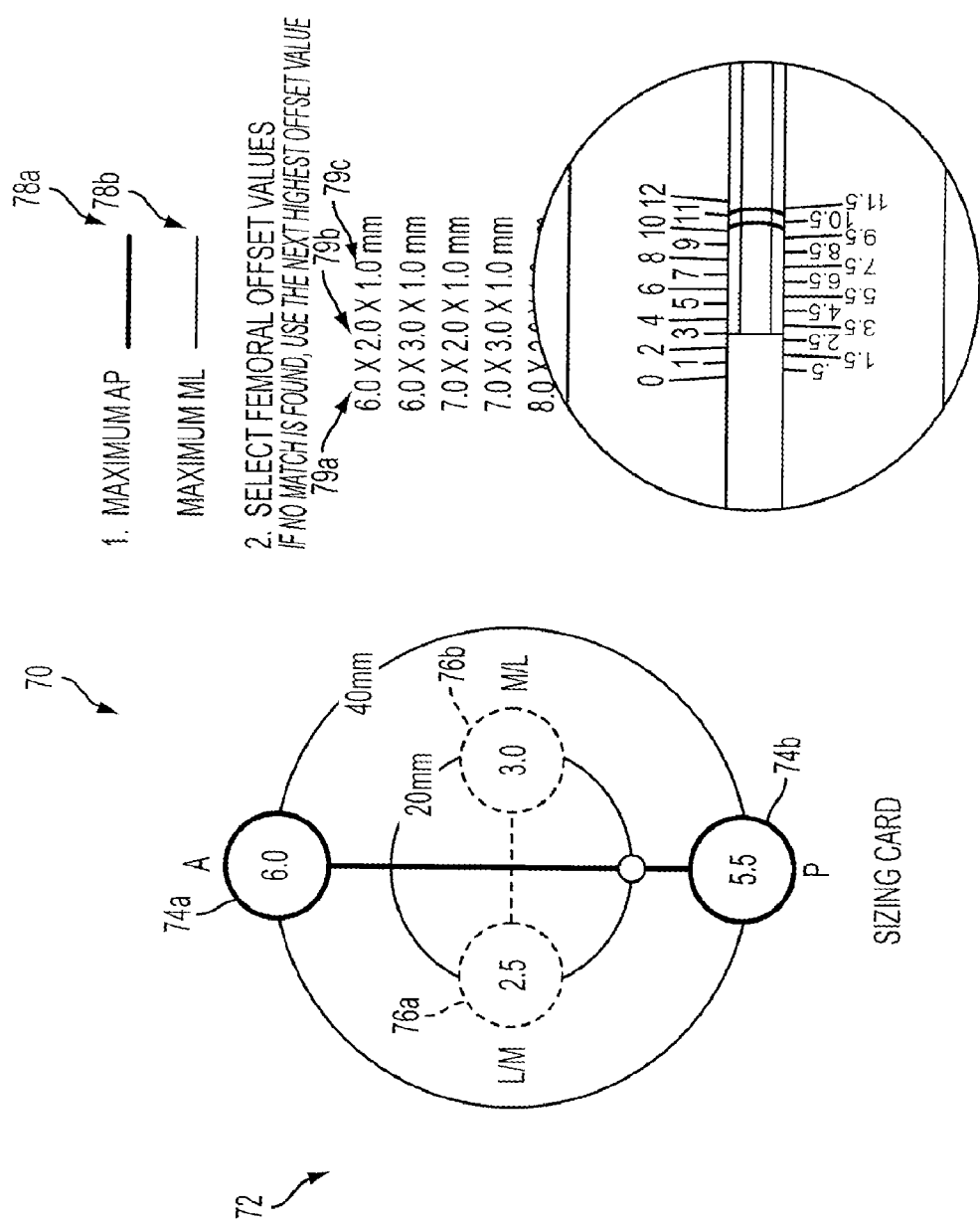
FIG. 9 depicts a sizing card.

The measurements obtained from the contact probes 50a, 50b may be recorded onto a sizing card 70, FIG. 9. The sizing card 70 may include a first area 72 graphically representing the AP and the ML planes. In particular, a first and a second query box 74a, 74b may be provided to fill in the first and second AP measurements and a first and a second query box 76a, 76b may be provided to fill in the first and second ML measurements. The query boxes 74a, 74b may optionally be connected by a circle representing the size of the outrigger 46 of the first contact probe 50a while query boxes 76a, 76b may optionally be connected by a circle representing the size of the outrigger 46 of the second contact probe 50b. The sizing card 70 may also include query boxes 78a, 78b provided to fill in the maximum values of the AP plane and the ML plane, respectively.

Based on the maximum values of the AP and ML plane in query boxes 78a, 78b, the offset values of the implant and test implant may be determined. As shown, the surgeon may select from a set of implants having predetermined offset values 79a-c. The values 79a-c correspond to the AP measurement 79a, ML measurement 79b, and depth 79c of the implant/test implant. It should be noted that the offset values of the implant/test implant may be used in combination with known geometrical ratios of the articular surface for a particular region of the articular surface. These geometric ratios may be found in published literature and may be utilized, for example, when the implant is placed proximate the interface between the posterior and distal regions of the articular surface. If further accuracy is desired (for example, but not limited to, defects extending further towards the posterior region and/or the anterior regions of the articular surfaces), the contour of the implant and articular surface may be determined as described in U.S. patent application Ser. No. 12/027, 121 entitled System and Method for Joint Resurface Repair filed Feb. 6, 2008, which is fully incorporated herein by reference.

Figure 10:
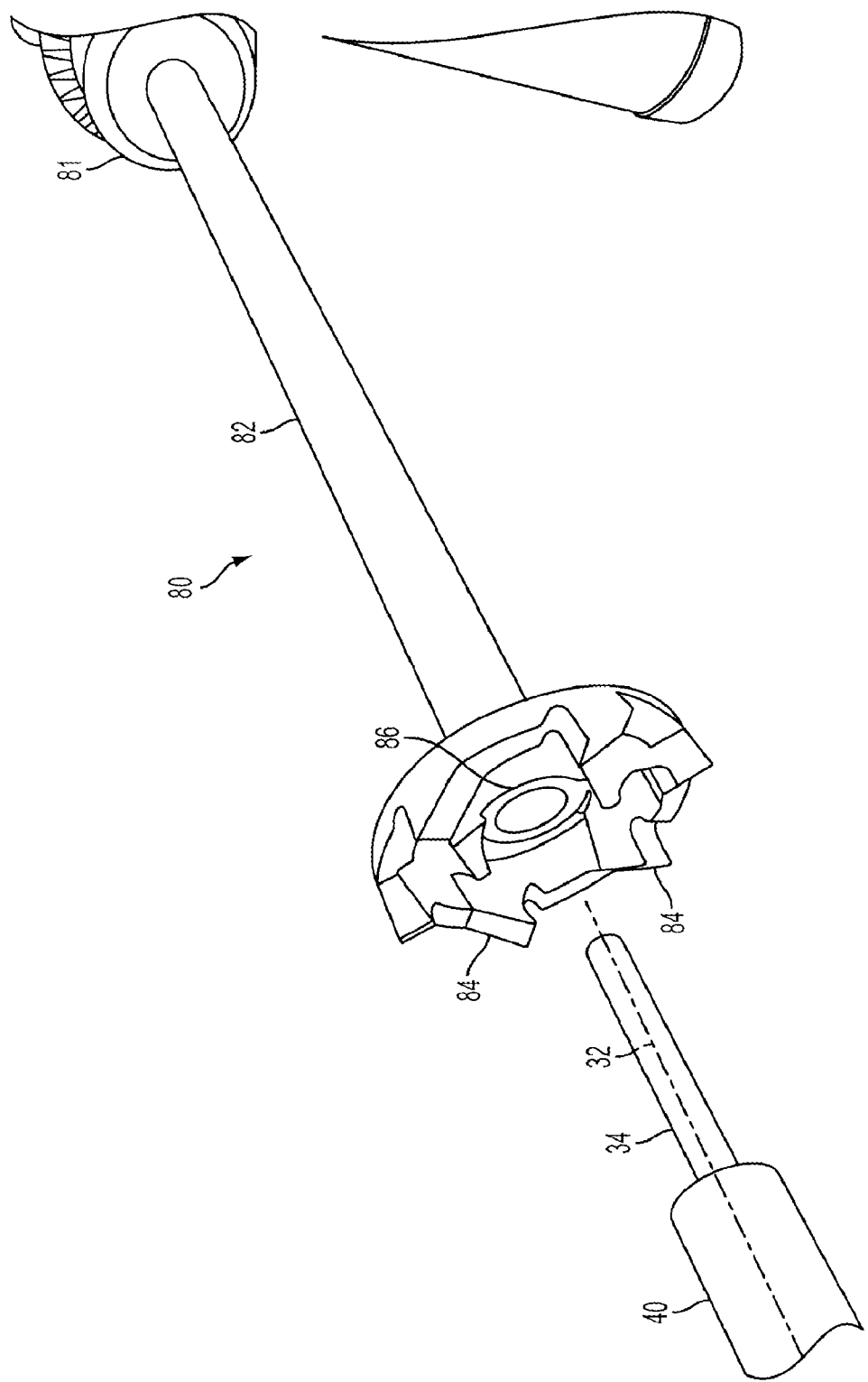
FIG. 10 is a side view of a surface reamer, the centering shaft of FIG. 5, and the pin of FIG. 4.

Turning now to FIG. 10, the diameter of a surface reamer 80 may be selected based on, for example, the maximum ML value (e.g., the value filled in query box 78b of sizing card 70). The surface reamer 80 may include a cannulated shaft 82 configured to be disposed over the centering shaft 40 and/or the guide pin 34 along the reference axis 32 and coupled to a drill 81. The surface reamer 80 may also include one or more cutting surfaces 84 and a shoulder 86 disposed about the opening 88 of the cannulated shaft 82.

Figure 11:
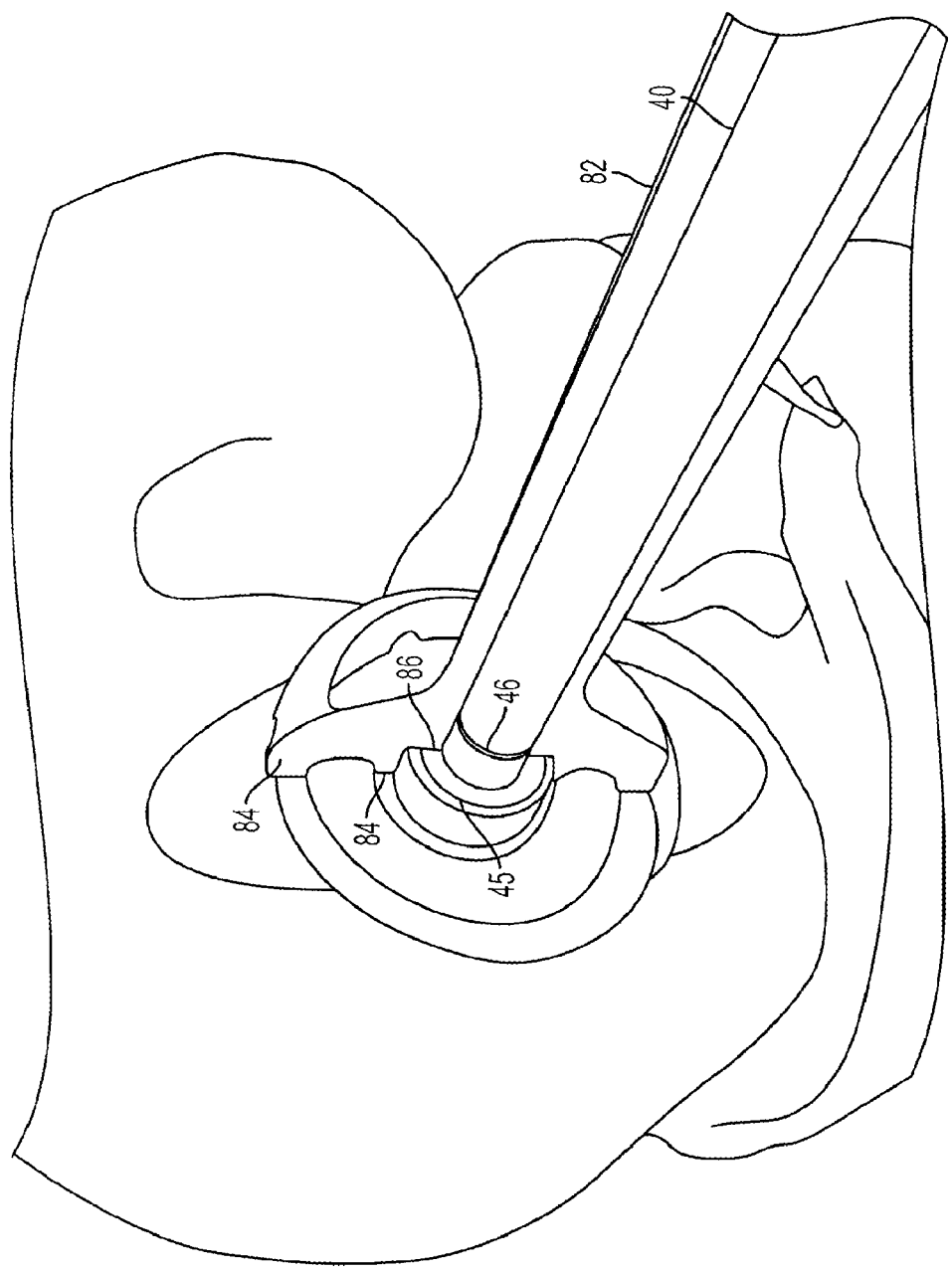
FIG. 11 is a cross-sectional view of a surface reamer of FIG. 10, the centering shaft of FIG. 5, and the pin of FIG. 4.

The surface reamer 80 may be advanced over the centering shaft 40 and/or the guide pin 34 along the reference axis 32 until the shoulder 86 of the surface reamer 80 abuts against the shoulder 45 of the centering shaft 40 as shown in FIG. 11. The contact between the two shoulders 86, 45 may be configured to control the depth of the excision in the articular surface. The cutters 84 may optionally be positioned about the surface reamer 80 to leave more material proximate the centering shaft 40 and/or the guide pin 34 along the reference axis 32 to facilitate removal and insertion of devices further along the method. Once the articular surface 16 has been excised about the reference axis 32, the surface reamer 80 and the centering shaft 40 may be removed.

Figure 13:
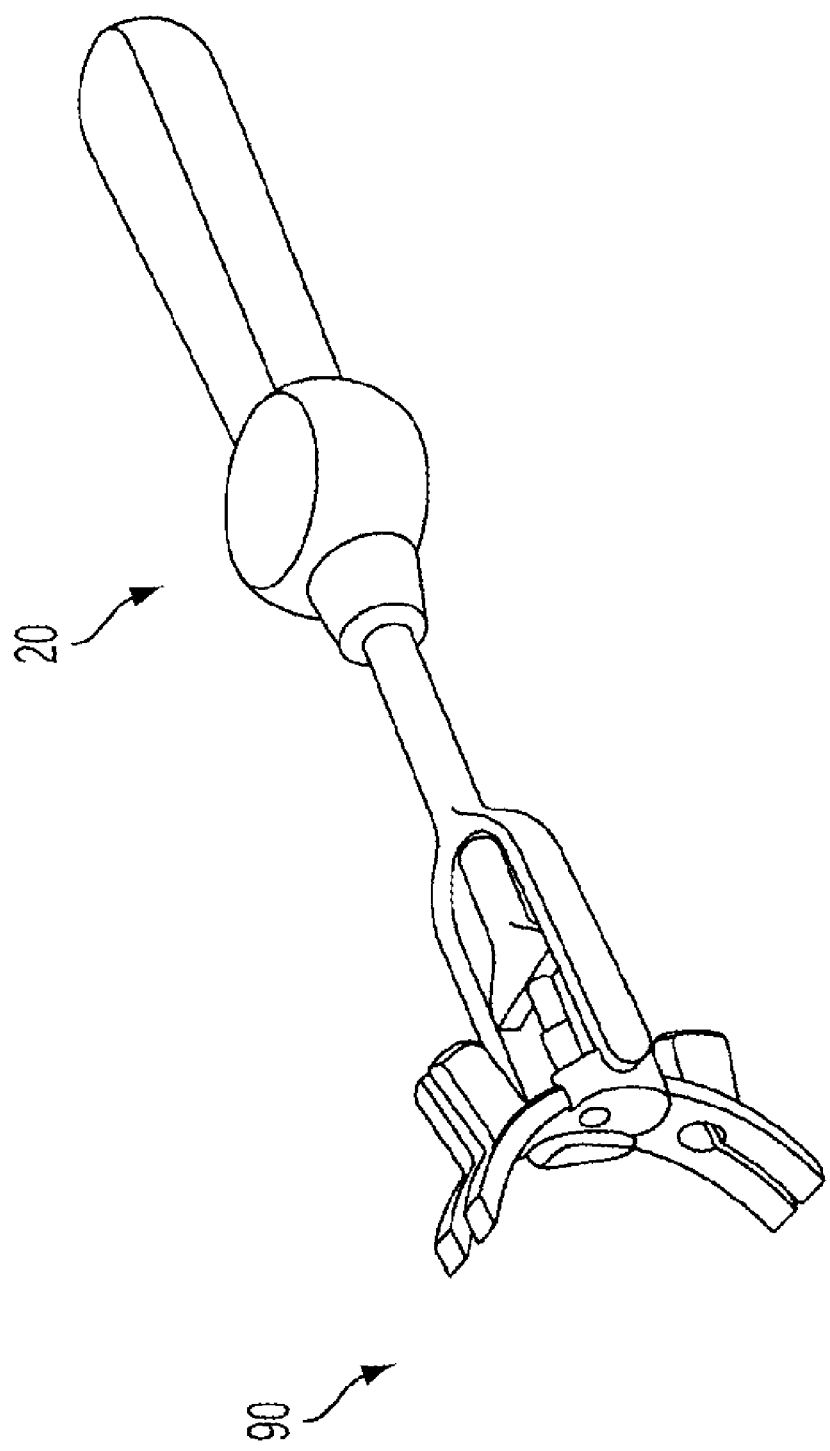
FIG. 13 is a side plan view of the guide block and drill guide shown in FIG. 12.

A guide block 90, FIG. 12, may be selected based on the maximum AP measurement value taken previously (e.g., the value filled in query box 78a of sizing card 70). The guide block 90 may be used to establish one or more working axis (for example, a superior and inferior working axis) for excising the articular surface 16 on either side of the reference axis along the AP plane. The guide block 90 may include a body 92 having an arcuate shaped interior surface 94 configured to contact the articular surface 16 along at least two points (e.g., the two end regions of the guide block 90). The guide block 90 may comprise a first bushing 95 defining a passageway or bore sized to receive the guide pin 34. The guide block 90 may be configured to be coupled to the drill guide 20. For example, according to one embodiment the AP arcuate shaped tip 24 may be removed from the drill guide 20 as shown in FIG. 12 and the guide block 90 may be coupled to the drill guide 20 with the first bushing 95 aligned with the cannulated passageway of the drill guide 20 as generally shown in FIG. 13.

Figure 14:
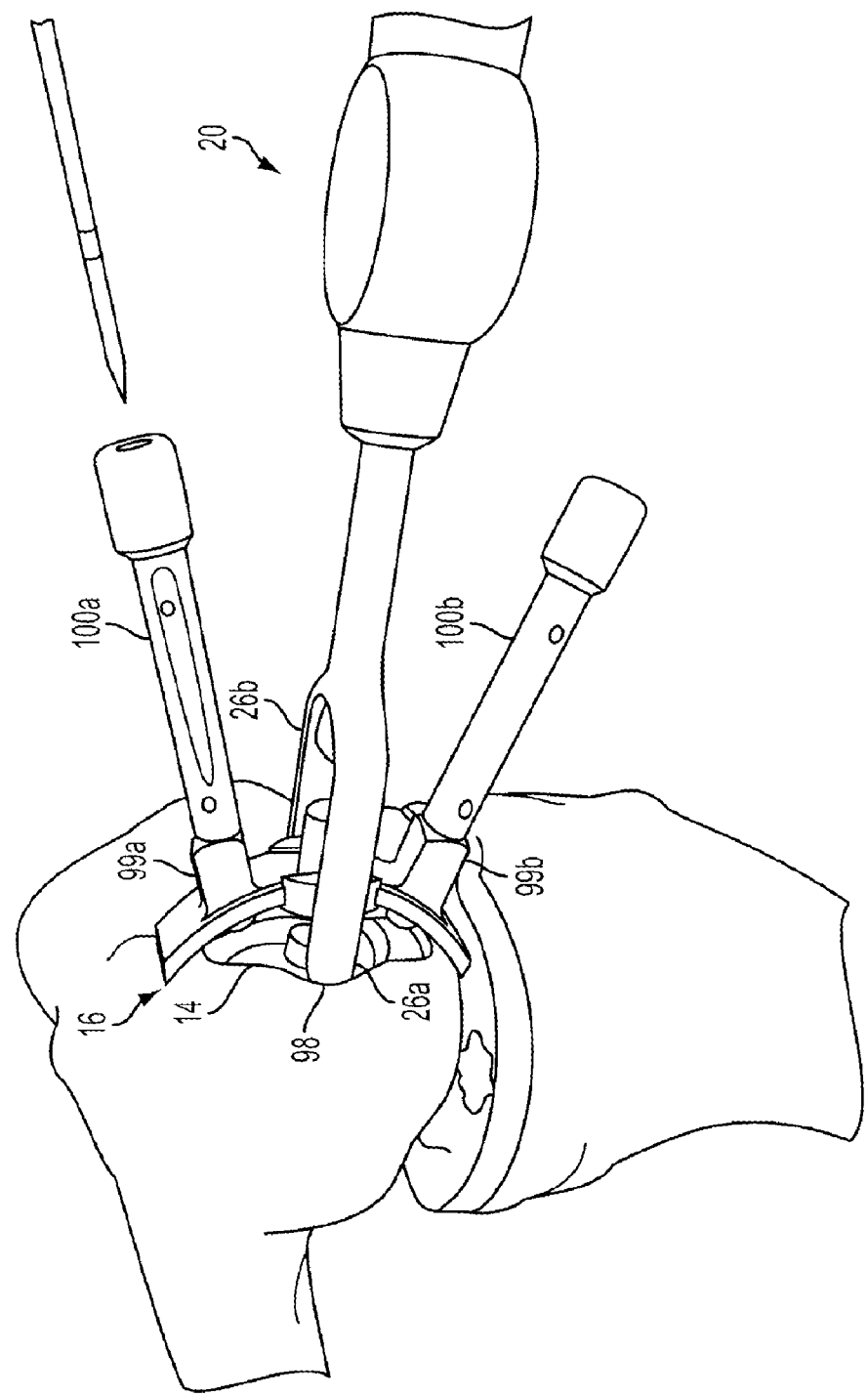
FIG. 14 is a side plan view of the guide block and drill guide shown in FIG. 12 disposed about the articular surface.

Turning now to FIG. 14, the first bushing 95 of the guide block 90 may be advanced along the guide pin 34 towards the articular surface 16, for example using the drill guide 20, such that the guide block 90 is generally aligned along the AP plane of the articular surface 16 and the ML prongs 26a, 26b of the drill guide 20 contact the bone within the excision site 98 formed by the surface reamer 80. The guide block 90 may include a superior and inferior pin sleeve receiver 99a, 99b configured to removably receive a superior and inferior pin sleeve 100a, 100b, respectively. The superior and inferior pin sleeve 100a, 100b may be provided to facilitate proper alignment of the inferior and superior working axis.

Figure 15:
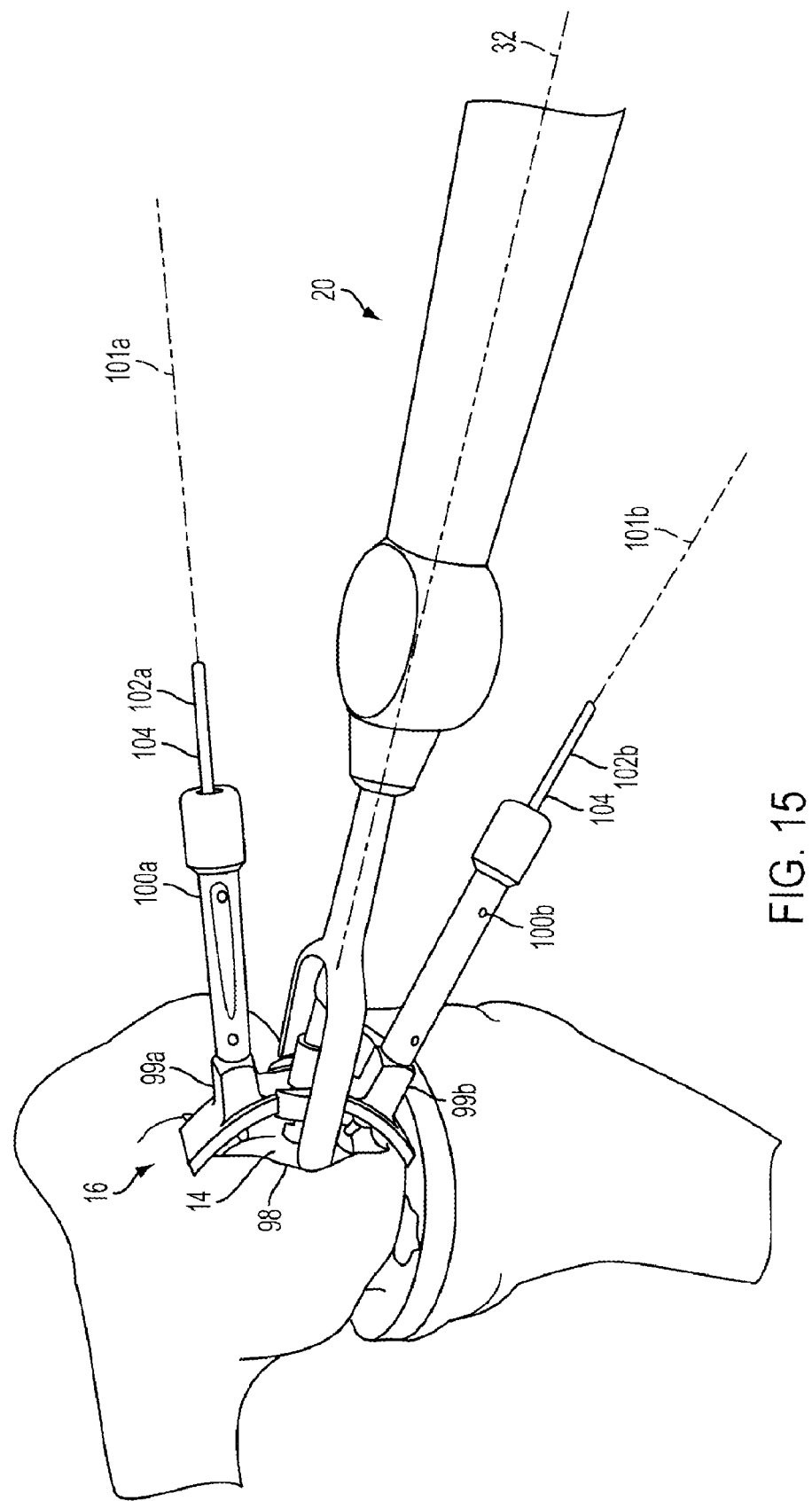
FIG. 15 is a side plan view of the guide block and drill guide shown in FIG. 13 including additional pins.

For example, a first and a second threaded pin 102a, 102b, FIG. 15, may be advanced through the superior and inferior pin sleeve 100a, 100b (for example, using a drill or the like) along the superior and inferior axis 101a, 101b. The depth of the pins 102a, 102b may be controlled using markings (for example, but not limited to, laser markings) disposed on the shaft 104 of the pins 102a, 102b.

Figure 16:
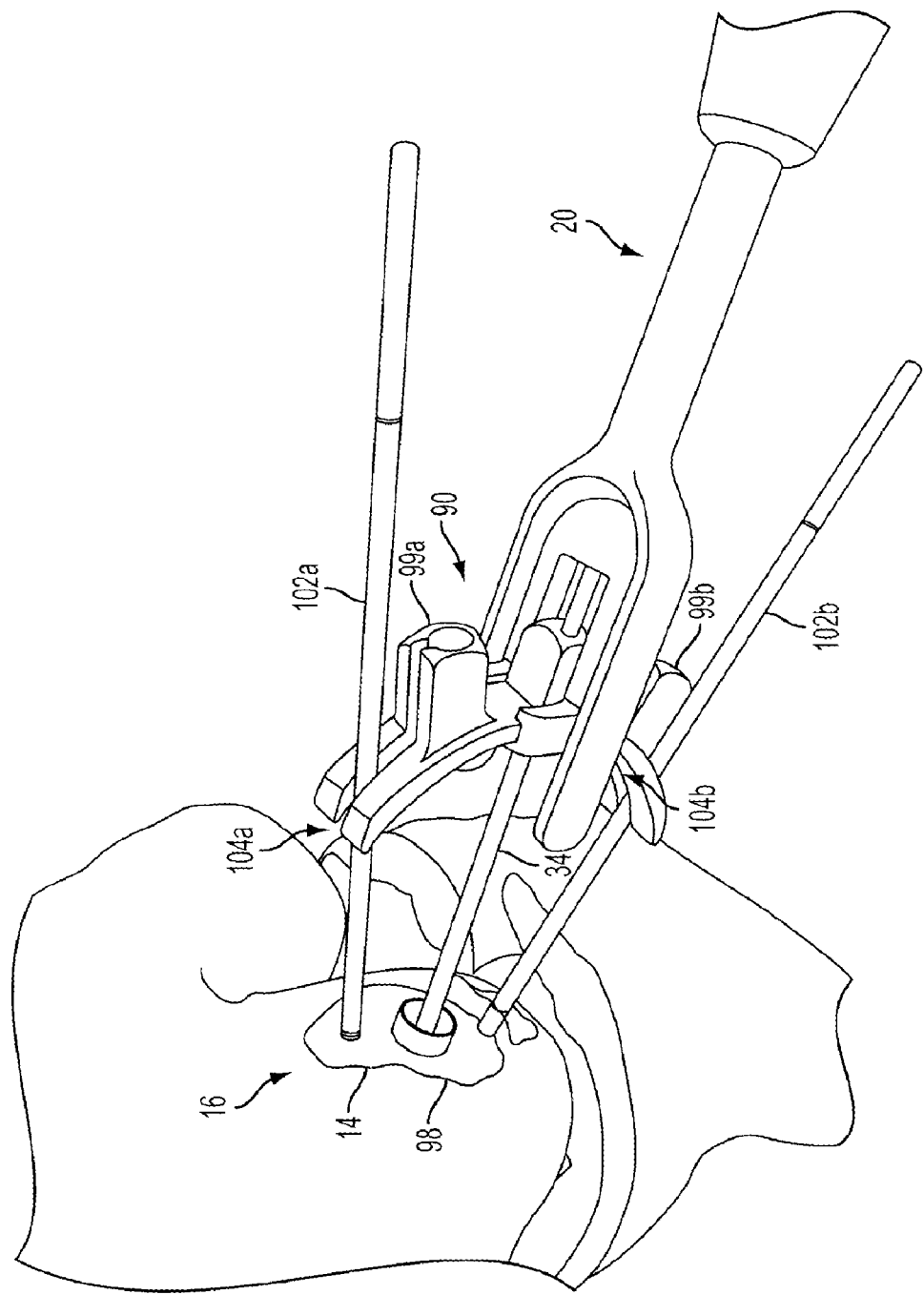
FIG. 16 is a side plan view of the guide block and drill guide shown in FIG. 15 being removed.

Once the superior and inferior pins 102a, 102b are coupled to the bone, the superior and inferior pin sleeves 100a, 100b may be removed from the superior and inferior pin sleeve receivers 99a, 99b. Turning now to FIG. 16, the guide block 90 may now be removed from the articular surface along the guide pin 34. The superior and inferior pin sleeve receivers 99a, 99b may be provided with slots 104a, 104b configured to allow the superior and inferior pins 102a, 102b to pass through the guide block 90 as the guide block 90 is slid along the guide pin 34.

Figure 17:
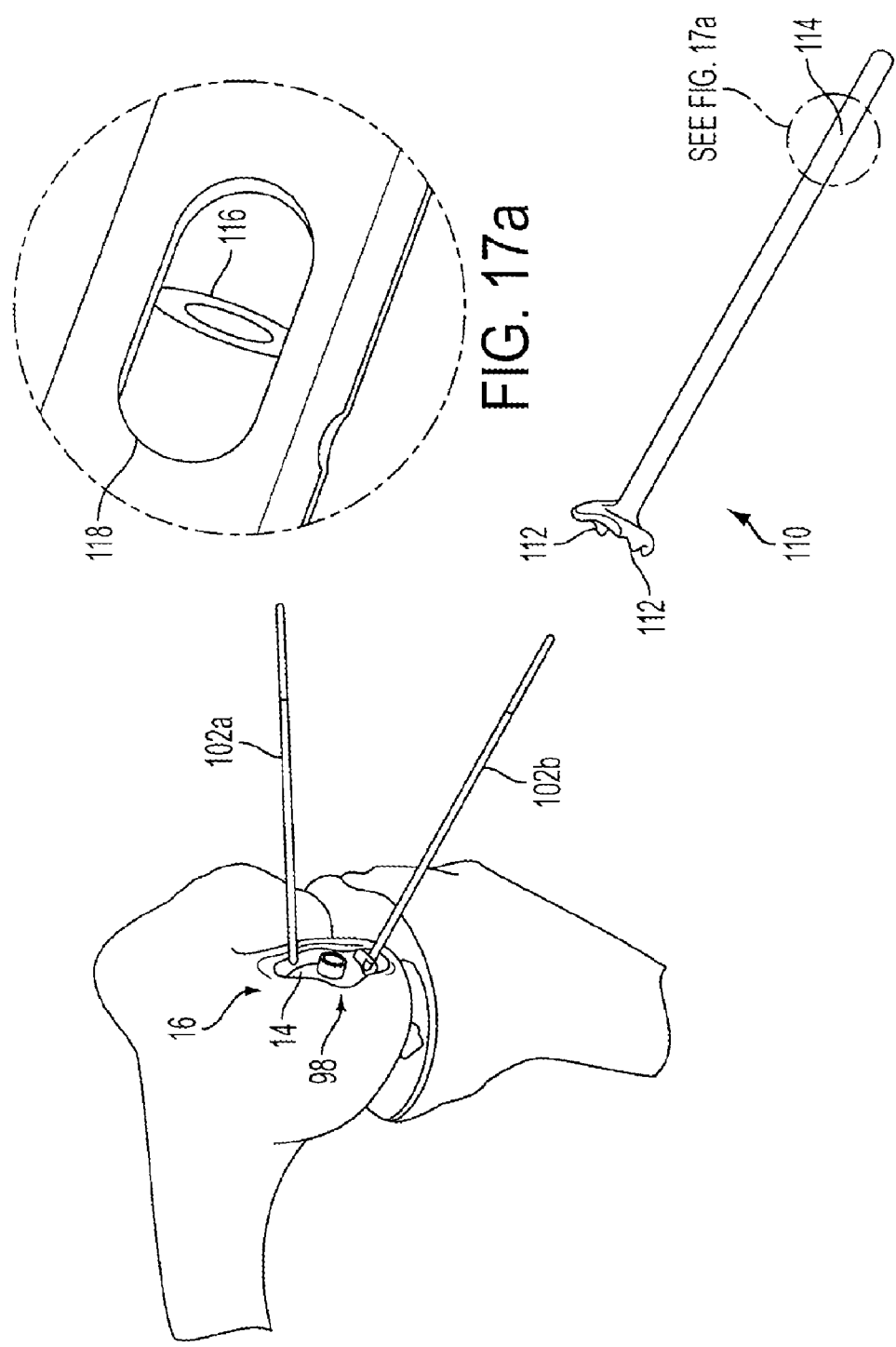
FIG. 17 is a side plan view of the pins disposed about the articular surface and a reamer.

Once the guide block is removed and the superior and inferior pins 102a, 102b have been established, the guide pin 34 may be removed. Next, a first and a second cannulated reamer 110, FIG. 17, may be advanced over the superior and inferior pins 102a, 102b to excise a first and a second portion of the articular surface 16 about the superior and inferior pins 102a, 102b. The reamer 110 may have one or more cutting surfaces 112 and may be provided with a depth stop 114 configured to control the depth of the excision sites about the superior and inferior pins 102a, 102b. According to one embodiment, the depth stop 114, FIG. 17a, may comprise a shoulder or stop 116 disposed within the cannulated passageway 118 of the reamer 110. The shoulder or stop 116 may be configured to engage with a distal end of the superior and inferior pins 102a, 102b, thereby preventing the reamer 110 from being advanced any further along the superior and inferior pins 102a, 102b and controlling the depth of the excision sites.

Figure 18:
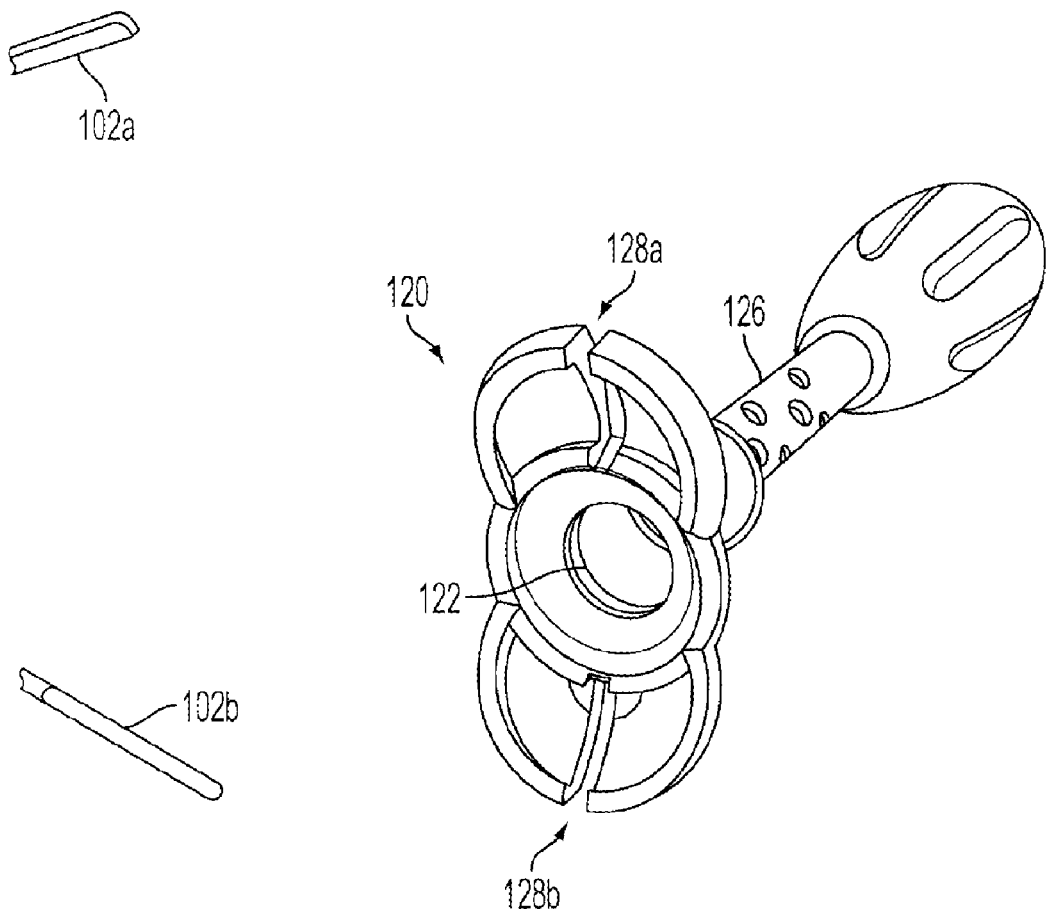
FIG. 18 is a side plan view of an implant sizing trial.
Figure 19:
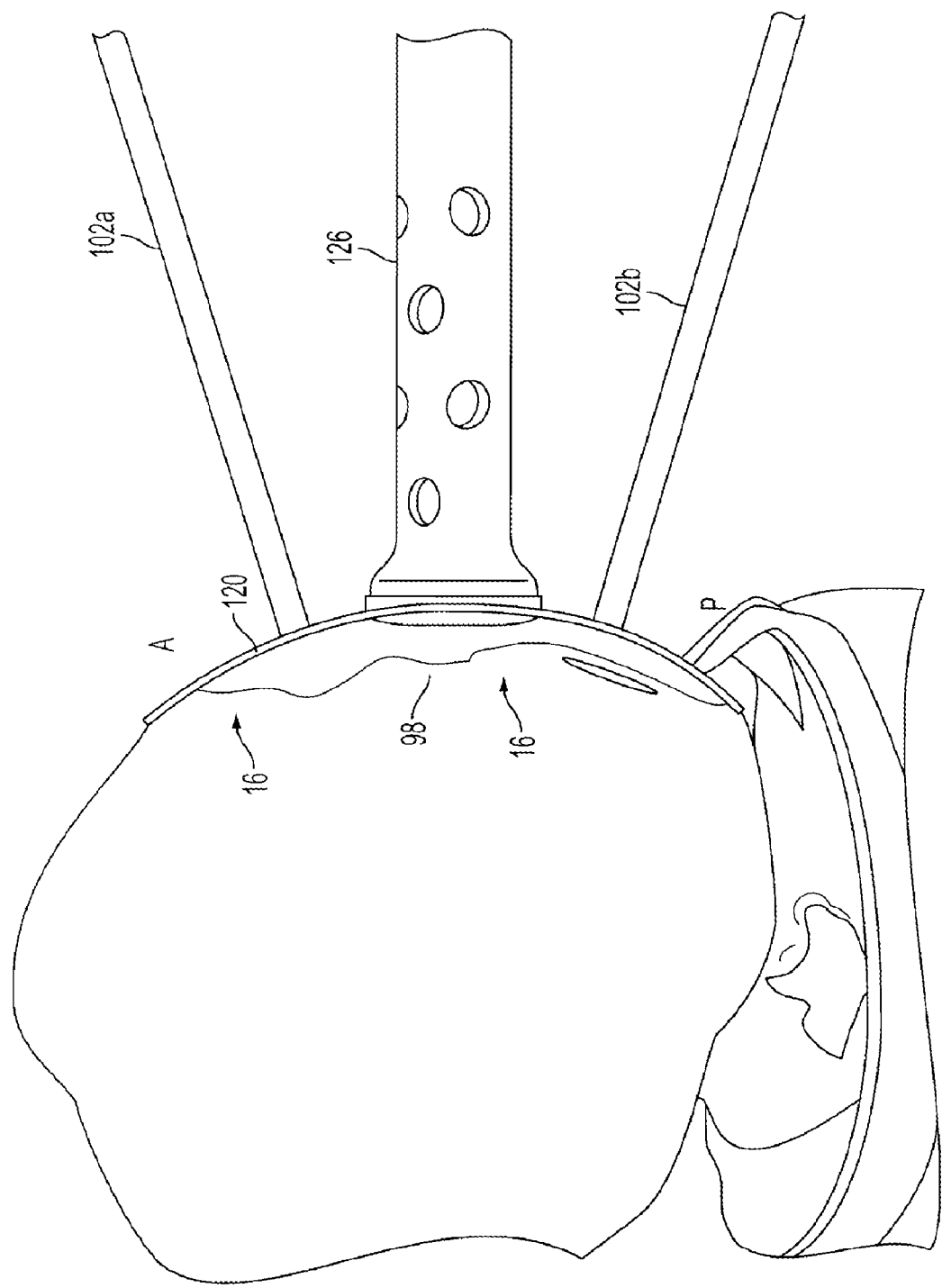
FIGS. 19 and 20 are a side and end plan view of the implant sizing trial of FIG. 18 disposed about the articular surface.
Figure 20:
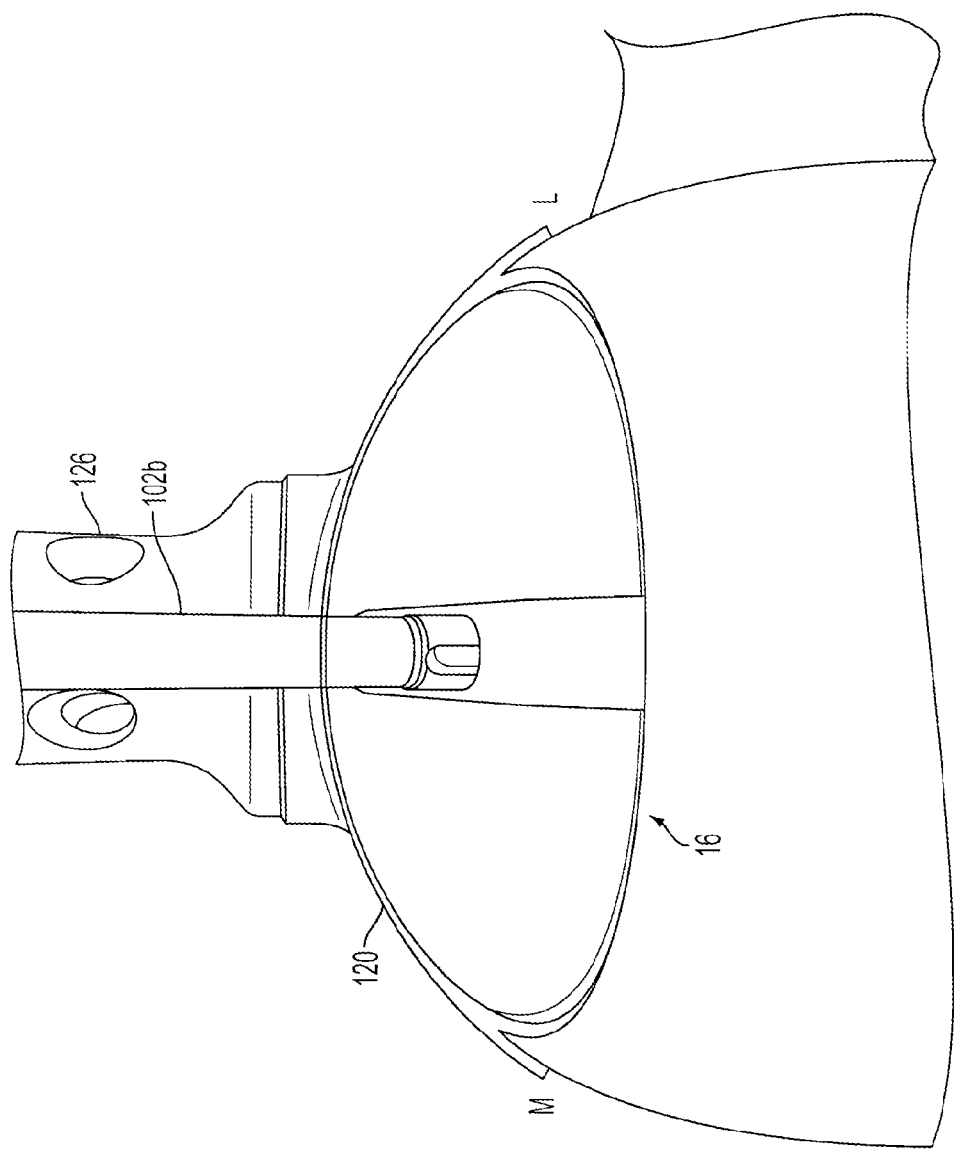

Turning now to FIG. 18, an implant sizing trial 120 may be selected based on the measurements taken of the articular surface 16. The implant sizing trial 120 may comprise a shape/contour generally corresponding to the shape/contour of the implant to be delivered. The implant sizing trial 120 may comprise a threaded opening 122 configured to be concentrically disposed about the working axis 32. The threaded opening 122 may also be configured to be threadably engaged with a cannulated shaft/handle 126. The implant sizing trial 120 may also include superior and inferior slots 128a, 128b configured to allow the implant sizing trial 120 to be advanced over the superior and inferior pins 102a, 102b as it is inserted into the excision sites 98 in the articular surface 16. Once the implant sizing trial 120 is inserted into the excision sites 98 in the articular surface 16, the fitment of the implant sizing trial 120 along the AP and ML planes may be confirmed visually as generally shown in FIGS. 19 and 20.

Figure 21:
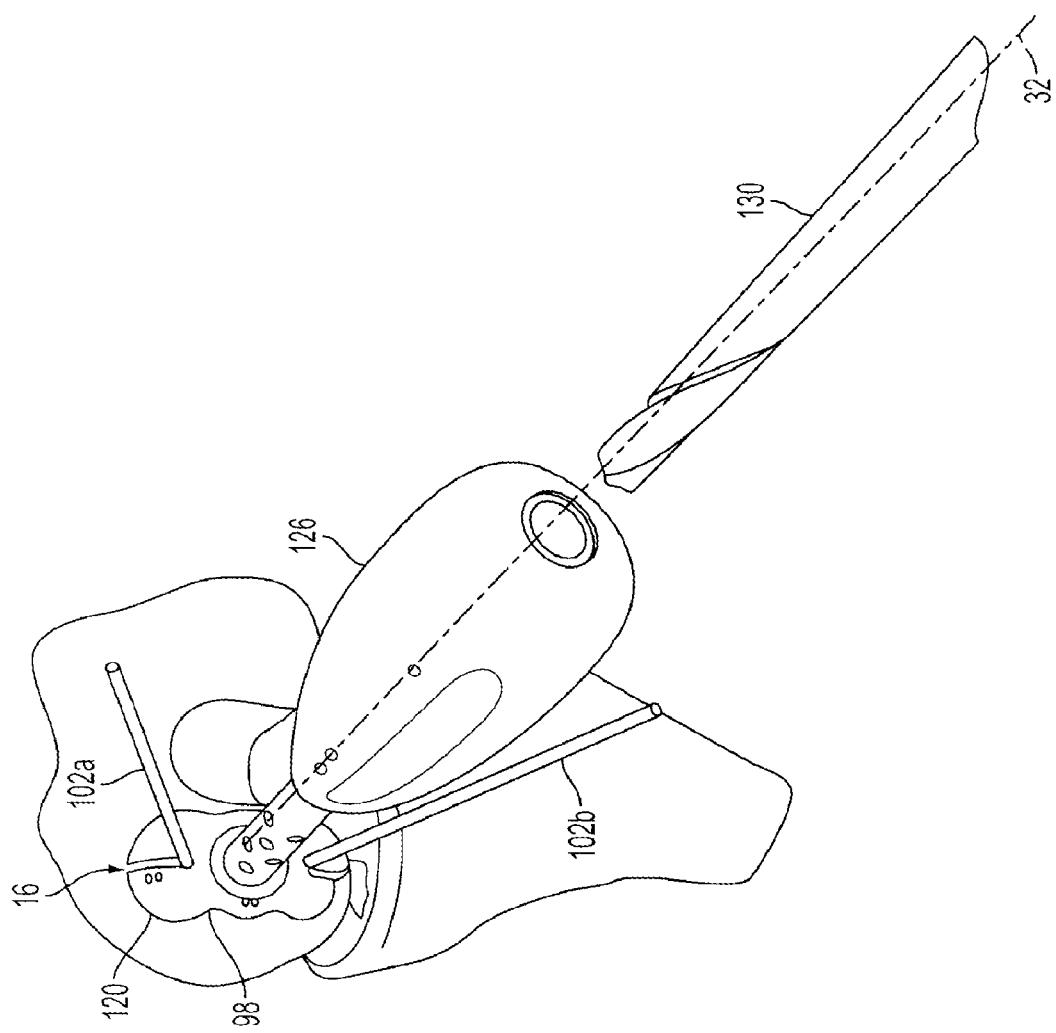
FIG. 21 is a perspective view of a pilot drill and the implant sizing trial of FIG. 18.
Figure 22:
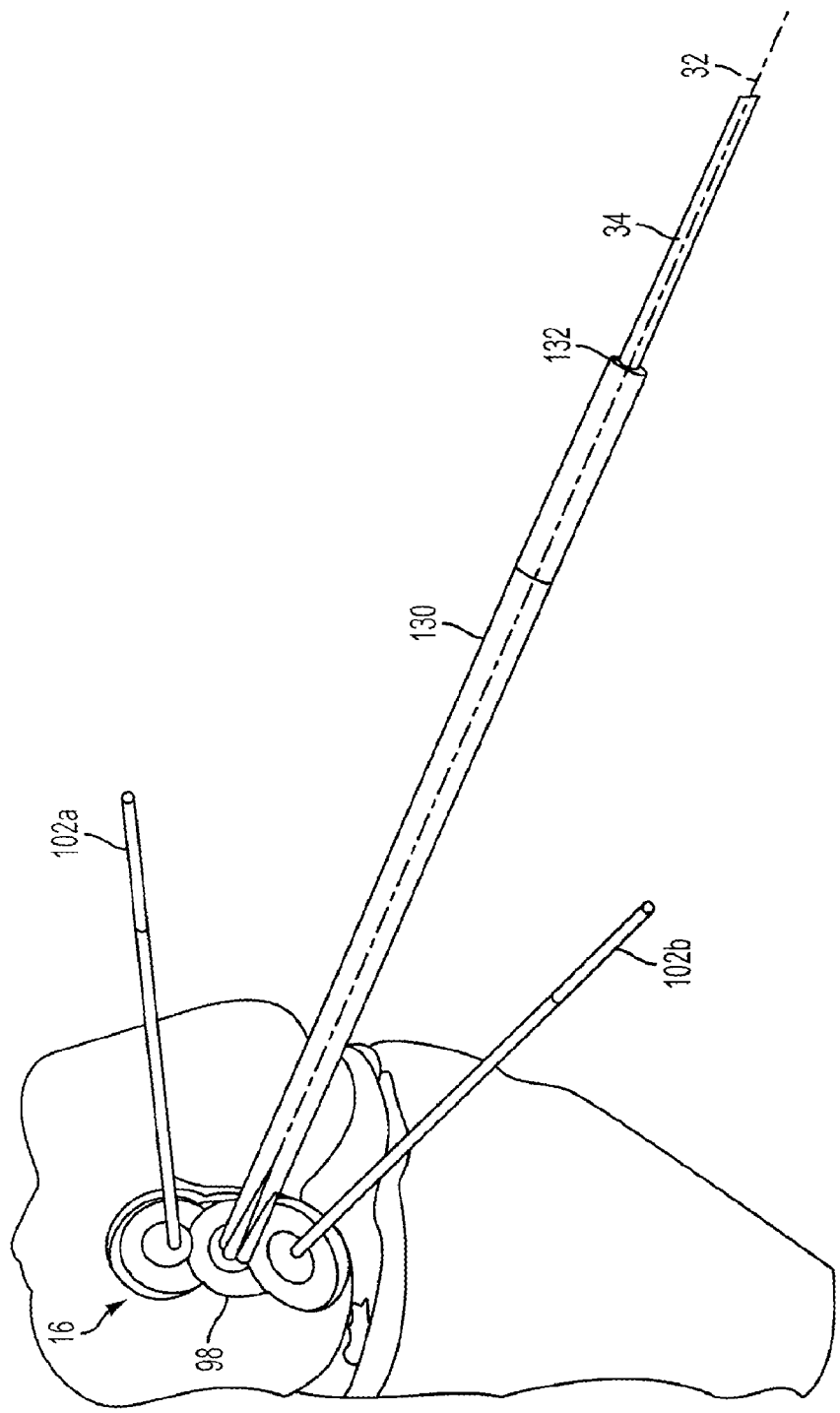
FIG. 22 is a side plan view of the pilot drill of FIG. 21 disposed about the articular surface.

With the implant sizing trial 120 inserted within the excision sites 98 and the fitment confirmed, a cannulated pilot drill 130, FIG. 21, may be advanced through the handle 126 and the implant sizing trial 120 into the bone along the reference axis 32. The pilot drill 130 may also include a depth control device such as, but not limited to, a marking (e.g., a laser marking or the like). With the cannulated pilot drill 130 secured in the bone, the implant sizing trial 120 and handle 126 may be removed and the guide pin 34 may be advanced through the cannulated passageway of the pilot drill 130 into the bone along the reference axis 32 as shown in FIG. 22. Again, the depth of the guide pin 34 may be controlled by way of a marking 132 (e.g., a laser marking or the like) along the shaft of the guide pin 34. For example, the depth of the guide pin 34 may be set once the laser marking 132 is flush with the end of the pilot drill 130.

Figure 23:
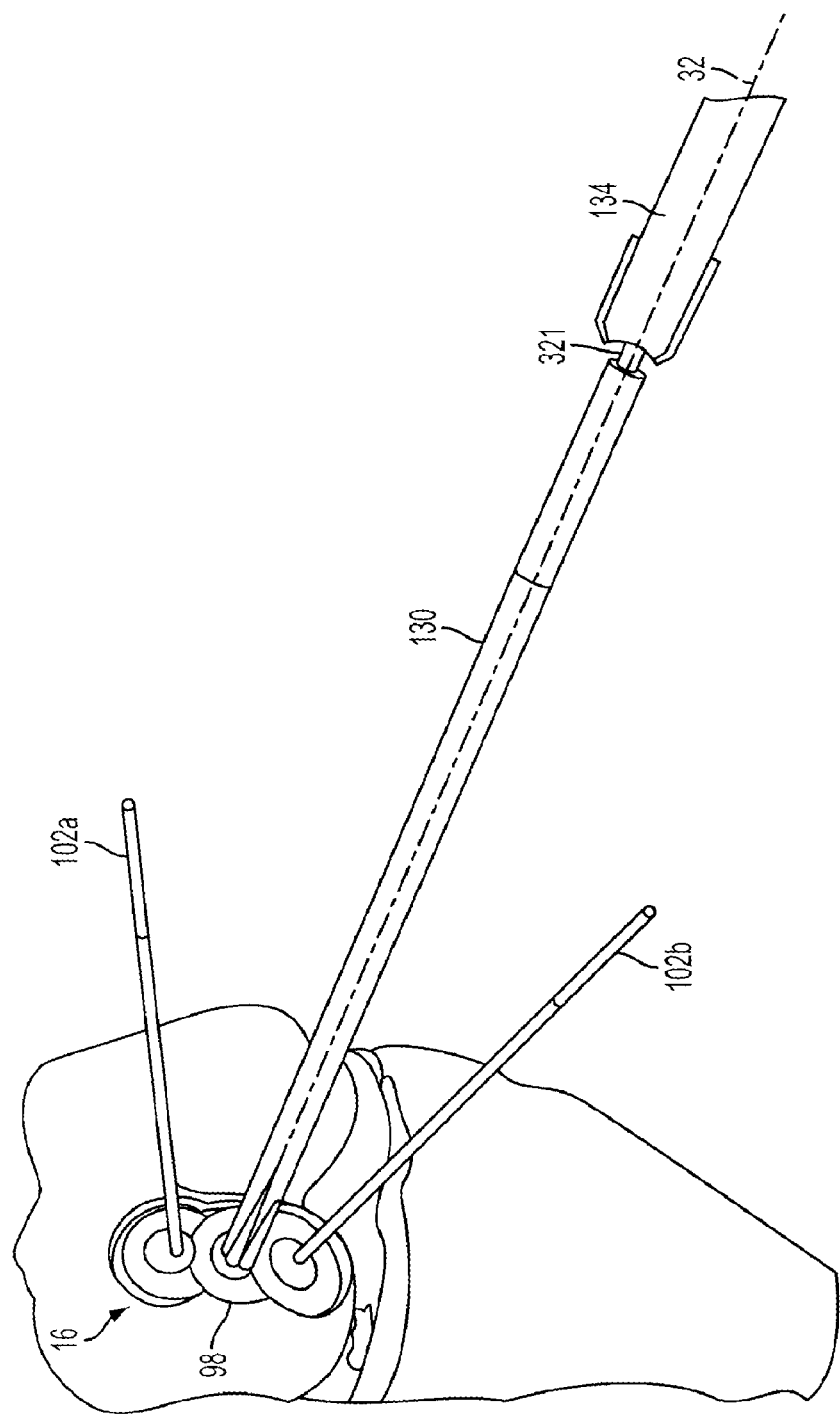
FIG. 23 is a perspective view of a step drill.

Turning now to FIG. 23, a cannulated step drill 134 may be advanced over the pilot drill 130 and the guide pin 34 into the articular surface 16 about the reference axis 32. The use of the pilot drill 130 and the cannulated step drill 134 may be configured to incrementally provide a larger opening in the bone about the reference axis 32 in the articular surface 16 to reduce the potential of chipping the bone about the reference axis 32. The cannulated step drill 134 may also include a depth stop for controlling the depth of the step drill 134 into the bone, for example, as generally described above with respect to FIG. 17a.

Figure 24:
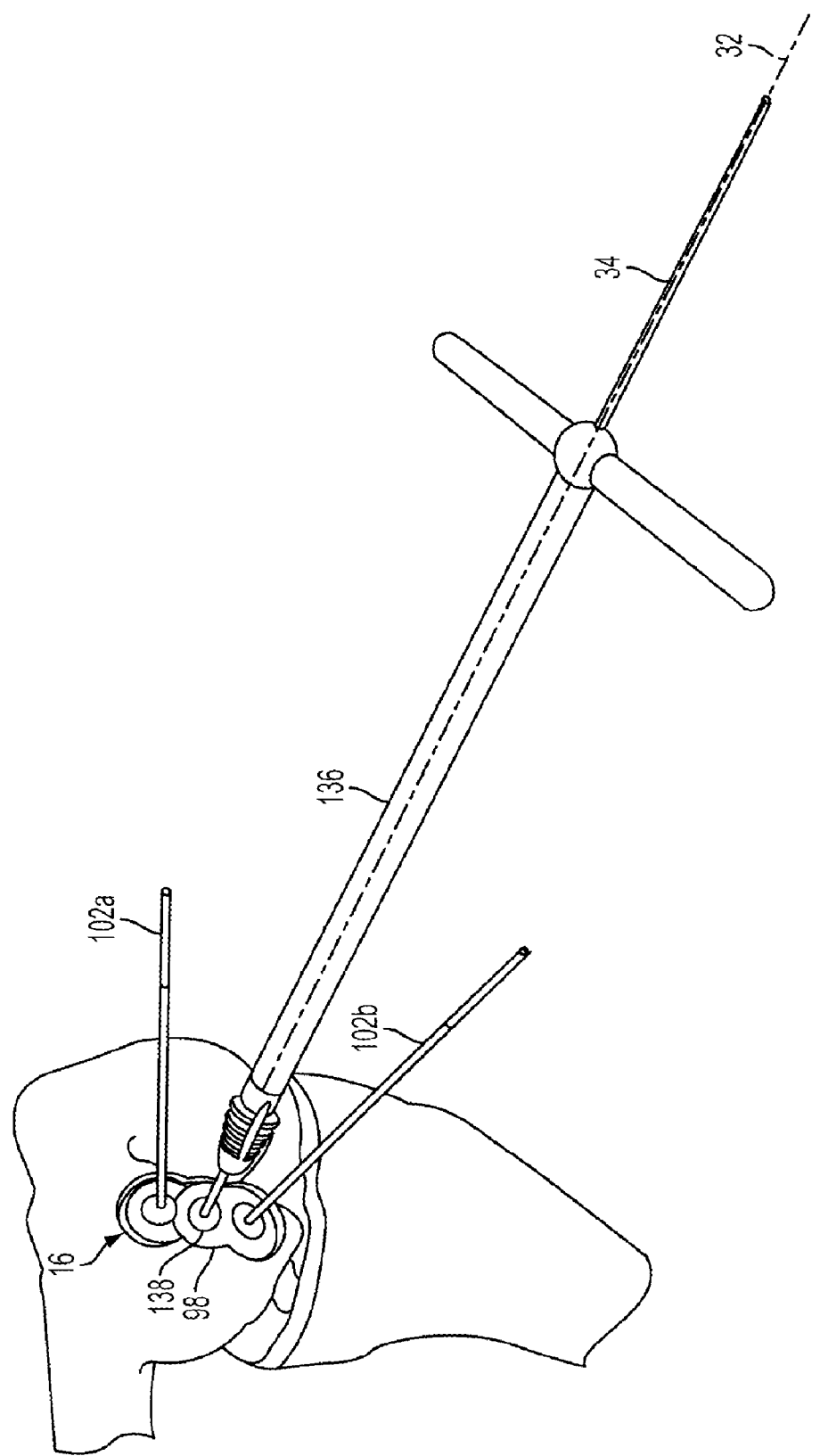
FIG. 24 is a perspective view of a tap.

Once the depth of the step drill 134 is set, the step drill 134 and the pilot drill 130 may be removed and a cannulated tap 136 may be advanced over the guide pin 34 as generally shown in FIG. 24. The depth that the tap 136 is advanced into the bone may be controlled based on a marking (e.g., a laser marking) on the guide pin 32. The tap 136 may be configured to provide a threaded opening 138 in the bone about the reference axis 32 to threadably receive the implant post as will be described below.

Figure 25:
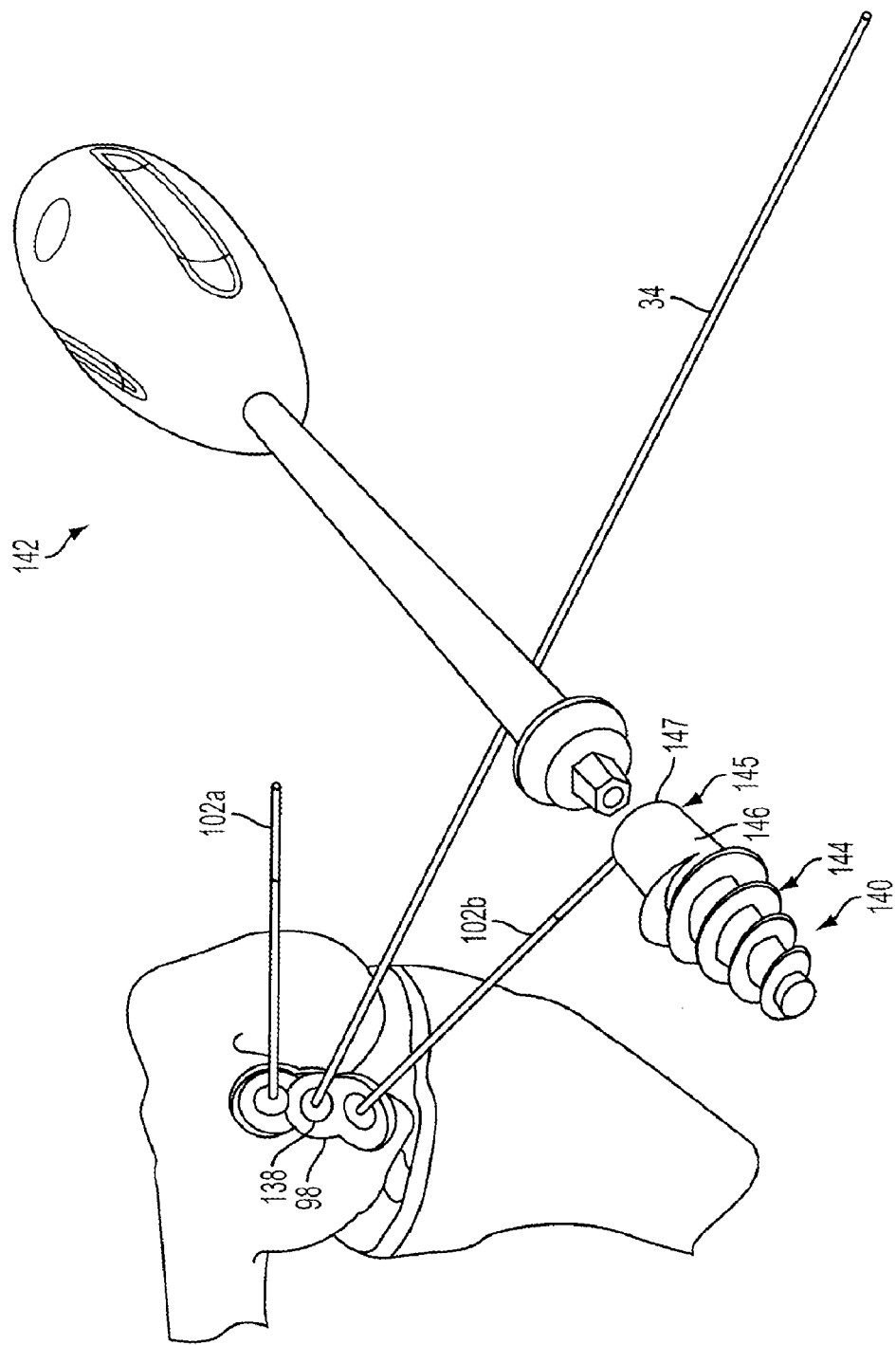
FIG. 25 is a perspective view of a tapered post and a driver.

With the opening about the reference axis 32 tapped, the tap 136 may be removed and the tapered post 140, FIG. 25, may be advanced over the guide pin 34 at least partially into the threaded opening 138, for example, using a hex driver 142. The tapered post 140 may include a tapered and threaded first end 144 and a second end 145 having a tapered exterior surface 146, for example, as described in U.S. Pat. Nos. 6,520,964, 6,610,067 and 6,679,917, all of which are fully incorporated herein by reference. The second end 145 may also include a hex-shaped internal cavity 147 configured to engage with a corresponding hex-shaped driver 148 of the hex driver 142. Both the tapered post 140 and the hex driver 142 may be cannulated such that they may be advanced over the guide pin 34.

Figure 26:
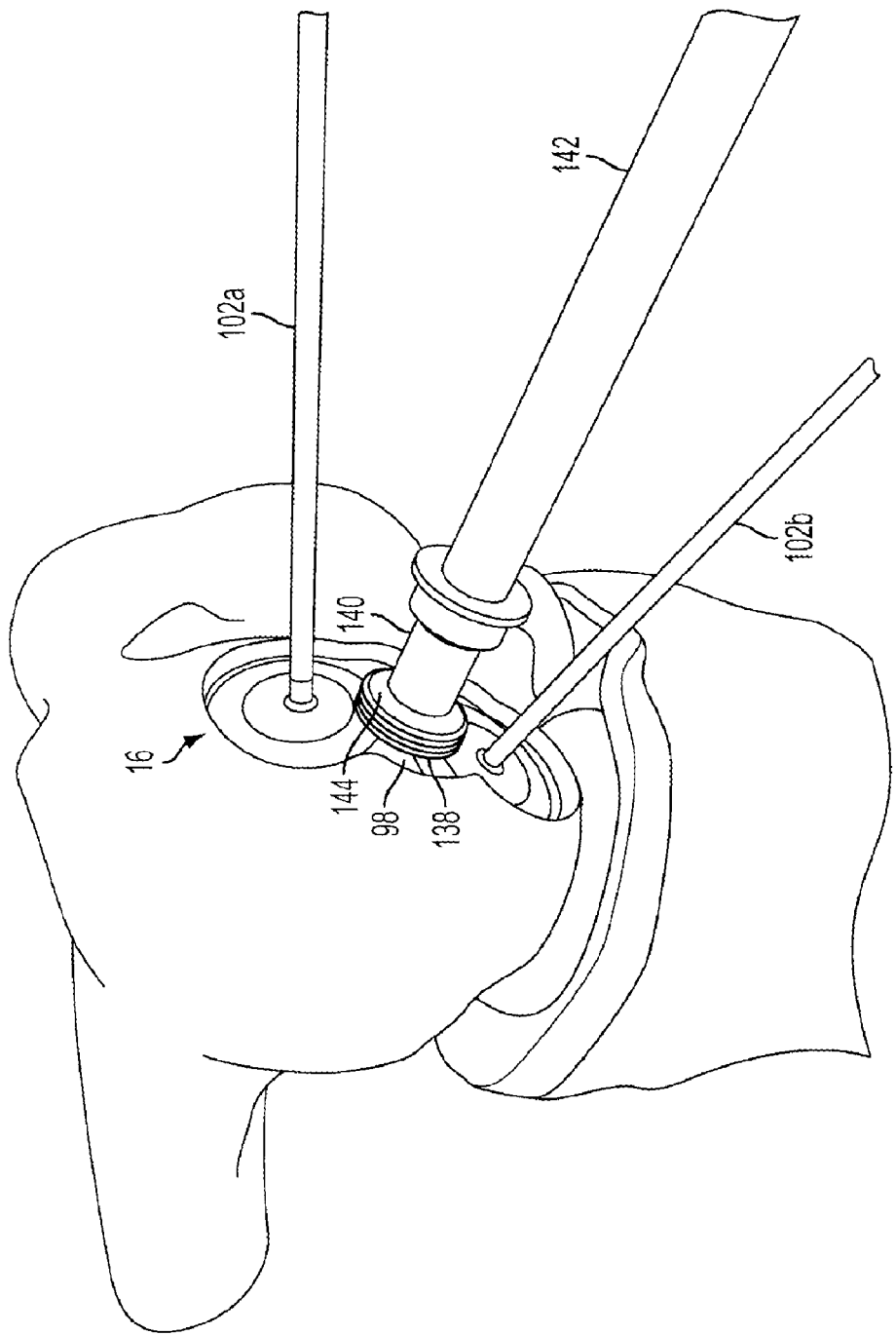
FIG. 26 depicts the tapered post of FIG. 25 disposed about the articular surface.
Figure 27:
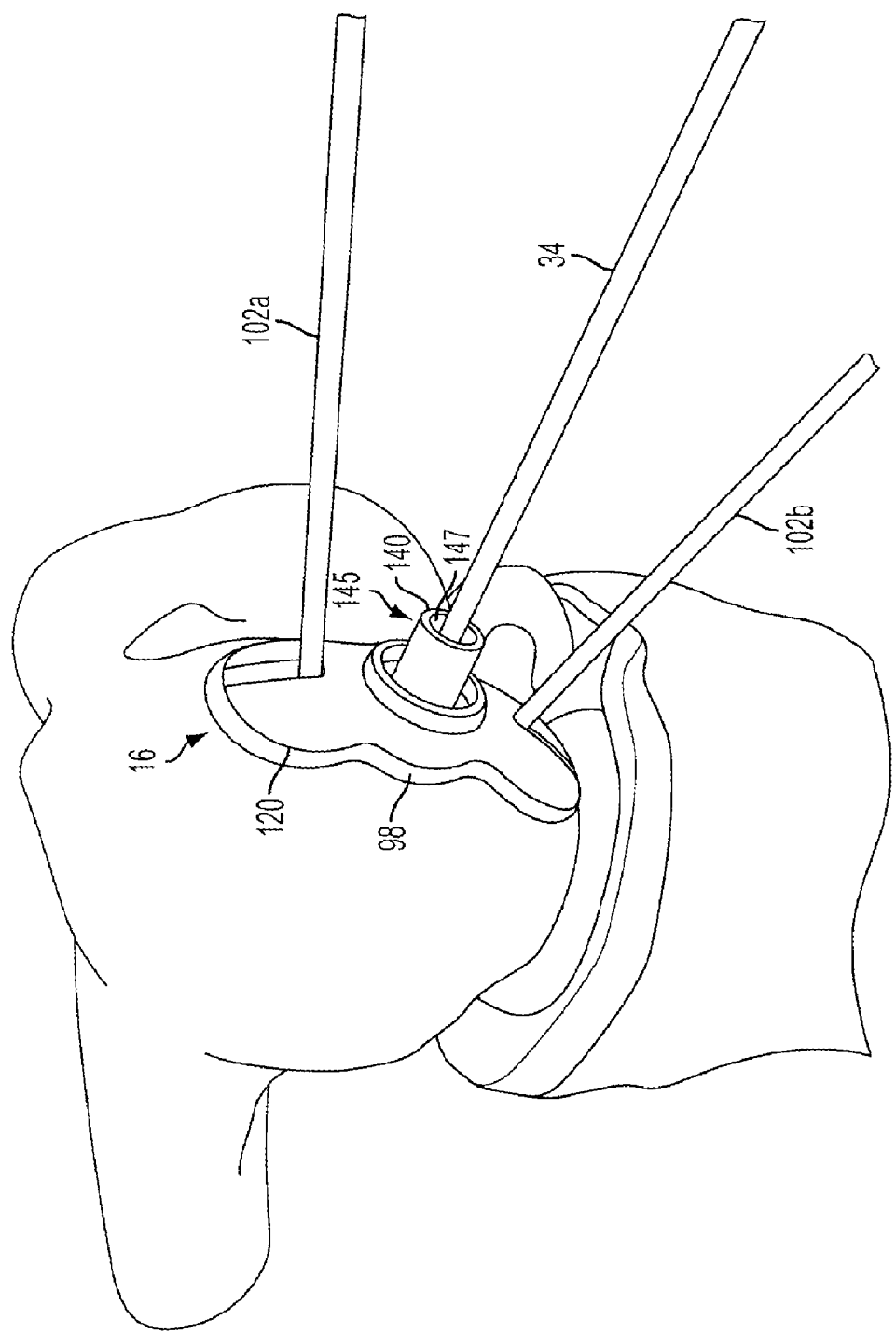
FIG. 27 depicts the tapered post of FIG. 25 and the implant sizing trial of FIG. 18 disposed about the articular surface.
Figure 28:
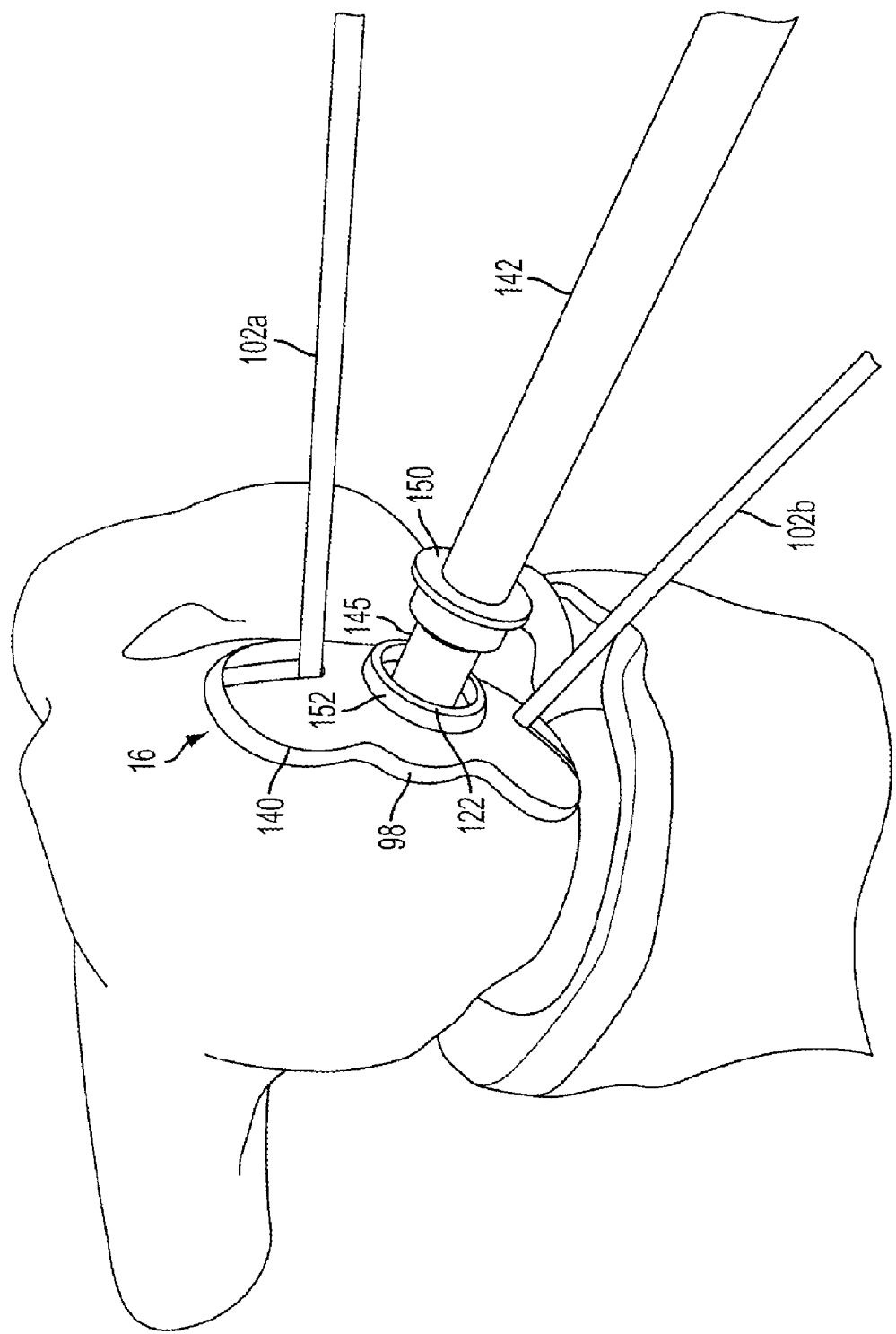
FIGS. 28-29 depict the tapered post of FIG. 25 being fully advanced within the articular surface.
Figure 29:
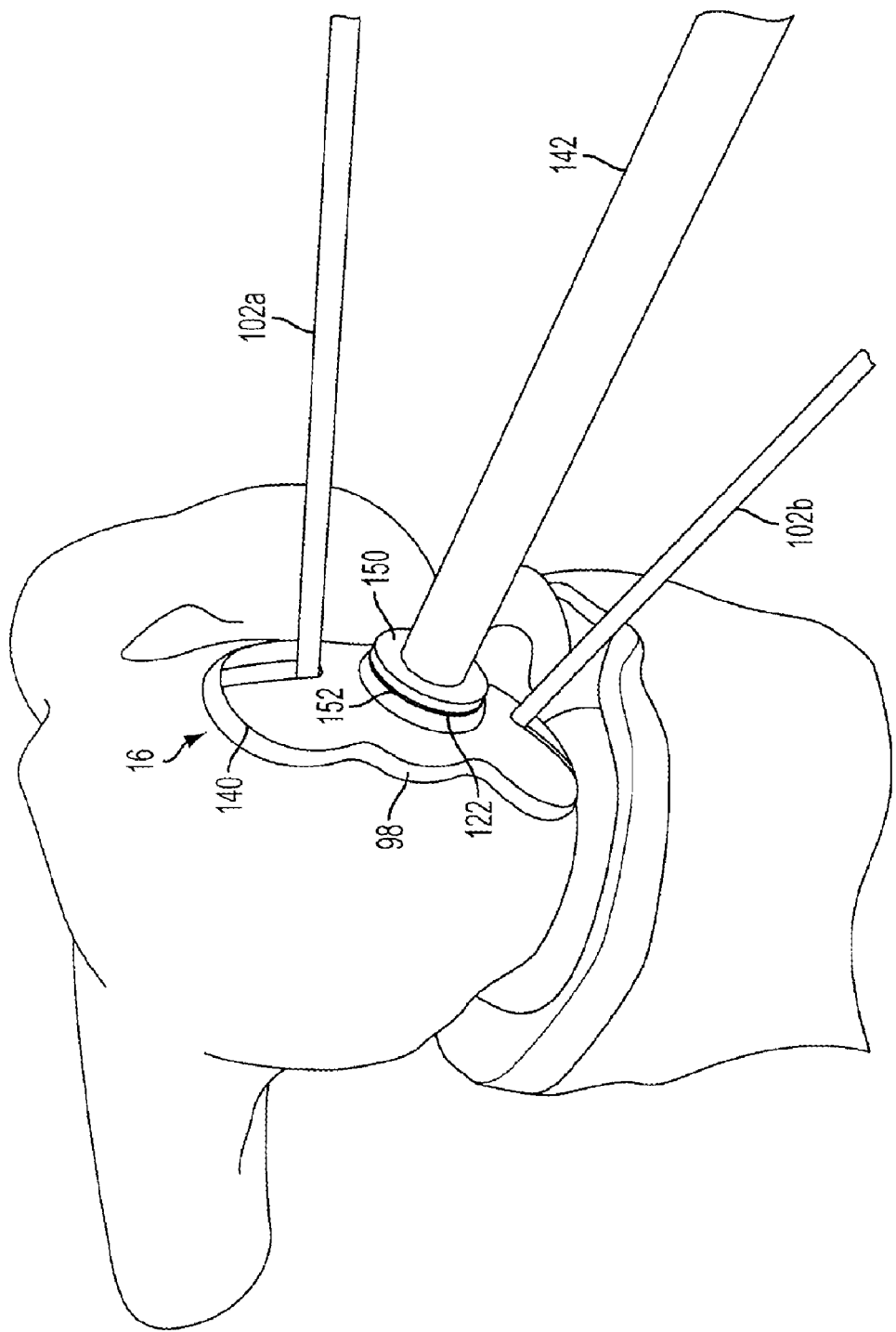

Referring now to FIG. 26, the tapered post 140 may be advanced along the guide pin 34 and partially inserted into the threaded opening 138 (for example, approximately half way) using the hex driver 142. According to one embodiment, the tapered post 140 may be inserted in the threaded opening 138 such at least most of the threaded end 144 is within the threaded opening 138. Once the tapered post 140 is partially received in the threaded opening 138, the hex driver 142 may be removed Turning now to FIG. 27, the implant sizing trial 120 may be placed into the excision sites 98. As can be seen, the second end 145 of the tapered post 140 may at least partially extend through the threaded opening 122 of the implant sizing trial 120. Using the hex driver 142, the implant sizing trial 120 may be fully advanced into the threaded opening 138 as generally shown in FIG. 28. The hex driver 142 may include a flared end 150 which may engage a shoulder 152 disposed about the opening 122 in the implant sizing trial 120 as shown in FIG. 29. The engagement of the flared end 150 and the shoulder 152 may control the final depth of the tapered post 140 into the threaded opening 138 in the bone.

Figure 30:
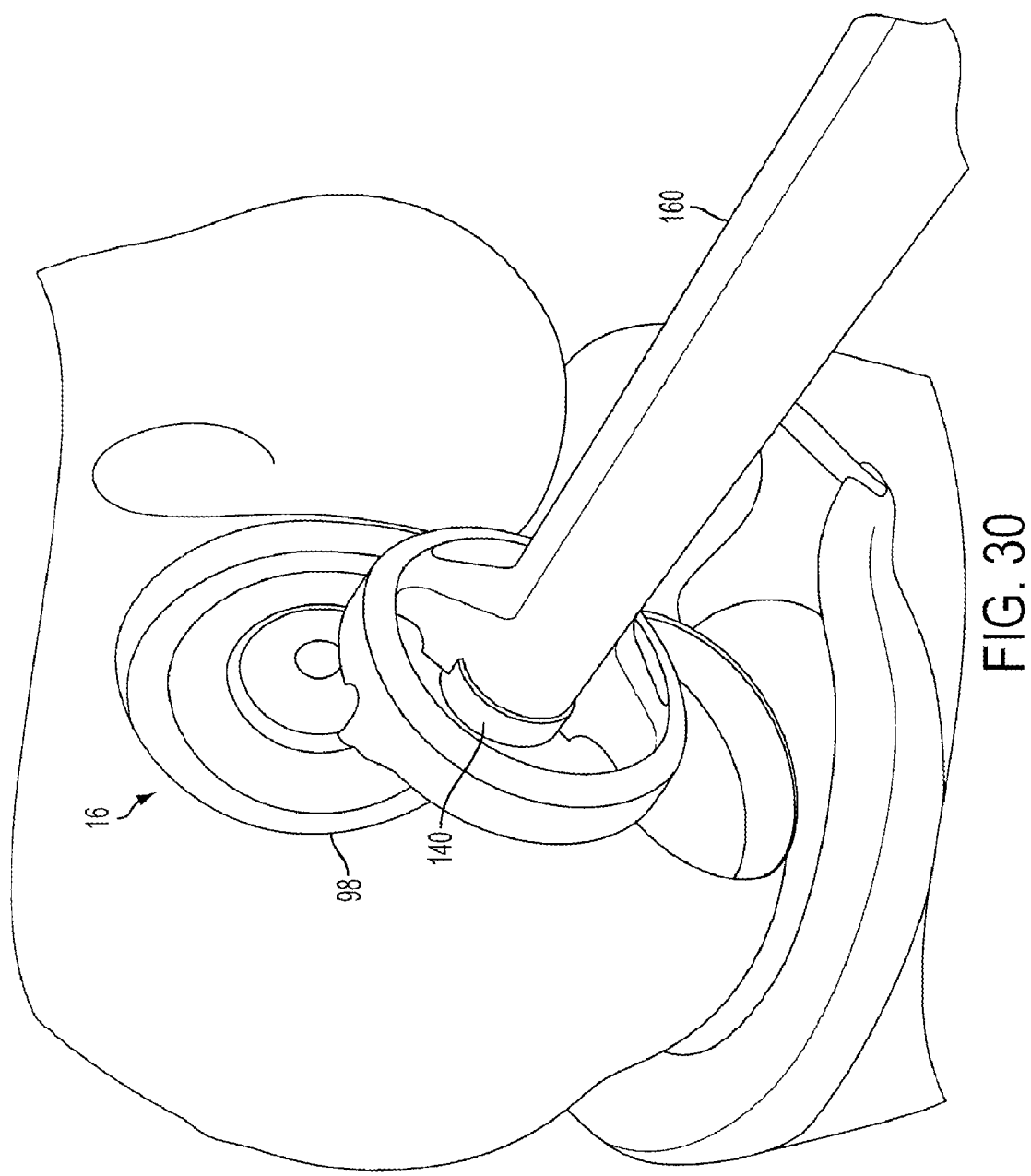
FIG. 30 depicts a reamer disposed about the tapered post of FIG. 25.

Once the tapered post 140 is fully advanced into the threaded opening 138, the hex driver 142, implant sizing trial 120 and superior and inferior pins 102a, 102b may be removed. Optionally, a cannulated reamer 160, FIG. 30, may be advanced over the guide pin 34 to remove any excess material about the reference axis 32. The depth of the reaming may be controlled when the shoulder 162 of the reamer 160 contacts the end of the tapered post 140 in a manner similar to that of FIG. 11 described above. The reaming may be provided to extra material left about the reference axis 32 during the reaming discussed with respect to FIGS. 10 and 11. This extra material may have been left to prevent accidental chipping during the subsequent operations.

Figure 31:
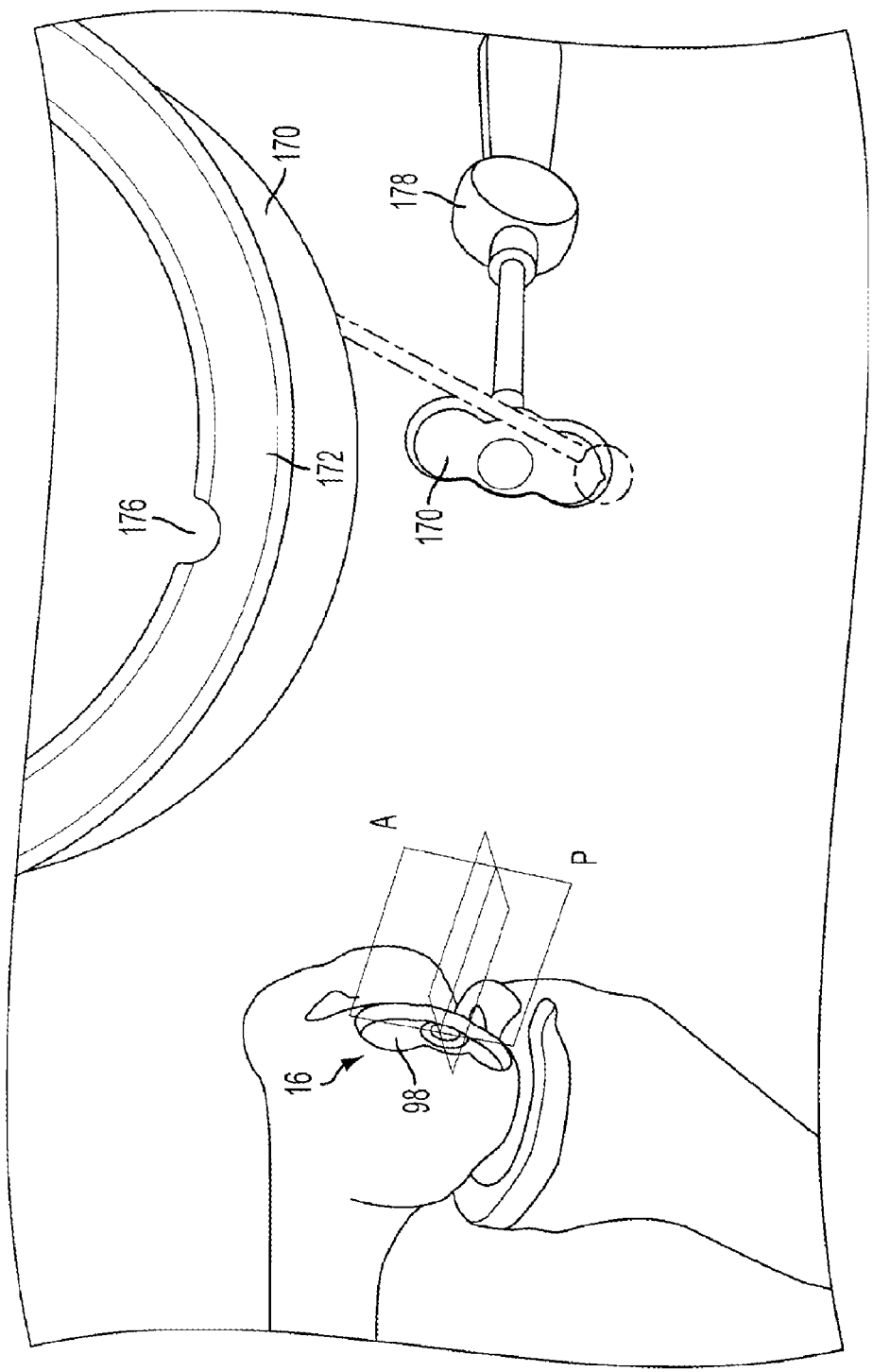
FIG. 31 is the bone-facing surface of an implant.

After the final reaming, the reamer 160 and the guide pin 32 may be removed leaving behind only the tapered post 140 in the bone. Next, the implant 170, FIG. 31, may be selected base on the measurements taken of the patient's articular surface 16. As discussed previously, the implant 170 may have a load bearing surface including a contour based on the measurements taken of the patient's articular surface 16 such that the load bearing surface generally corresponds to the patient's original articular surface 16. According to one embodiment, the implant 170 may include an implant as described in U.S. patent application Ser. No. 10/373,463 filed Feb. 24, 2003, U.S. Pat. No. 6,679,917 issued Jan. 20, 2004, U.S. Pat. No. 6,610,067 issued Aug. 26, 2003, U.S. Pat. No. 6,520,964 issued Feb. 18, 2003, and U.S. Provisional Application Ser. No. 60/201,049 filed May 1, 2000, all of which are fully incorporated hereby incorporated by reference.

The bone facing surface 172 of the implant 170 may include indicia 176 representing either posterior and/or anterior sides of the implant 170. This indicia 176 may be used by the surgeon to properly align the implant 170 along the AP and ML planes within the excision site 98. The implant 170 may be inserted into the excision site 98 using a grasping device 178 such as, but not limited to, a suction cup coupled to a handle.

Figure 32:
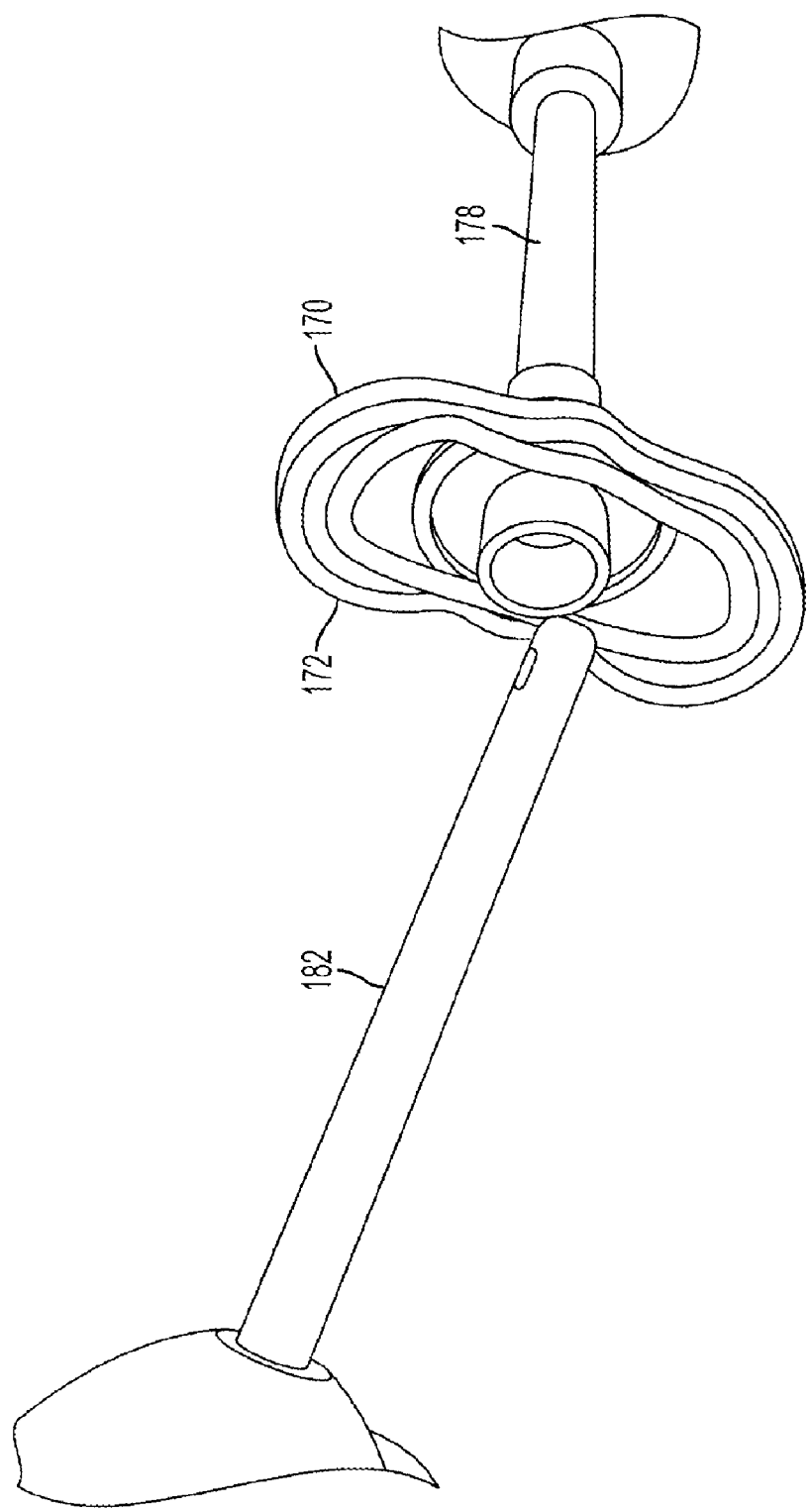
FIG. 32 is the bone-facing surface of an implant of FIG. 31 with an adhesive.
Figure 33:
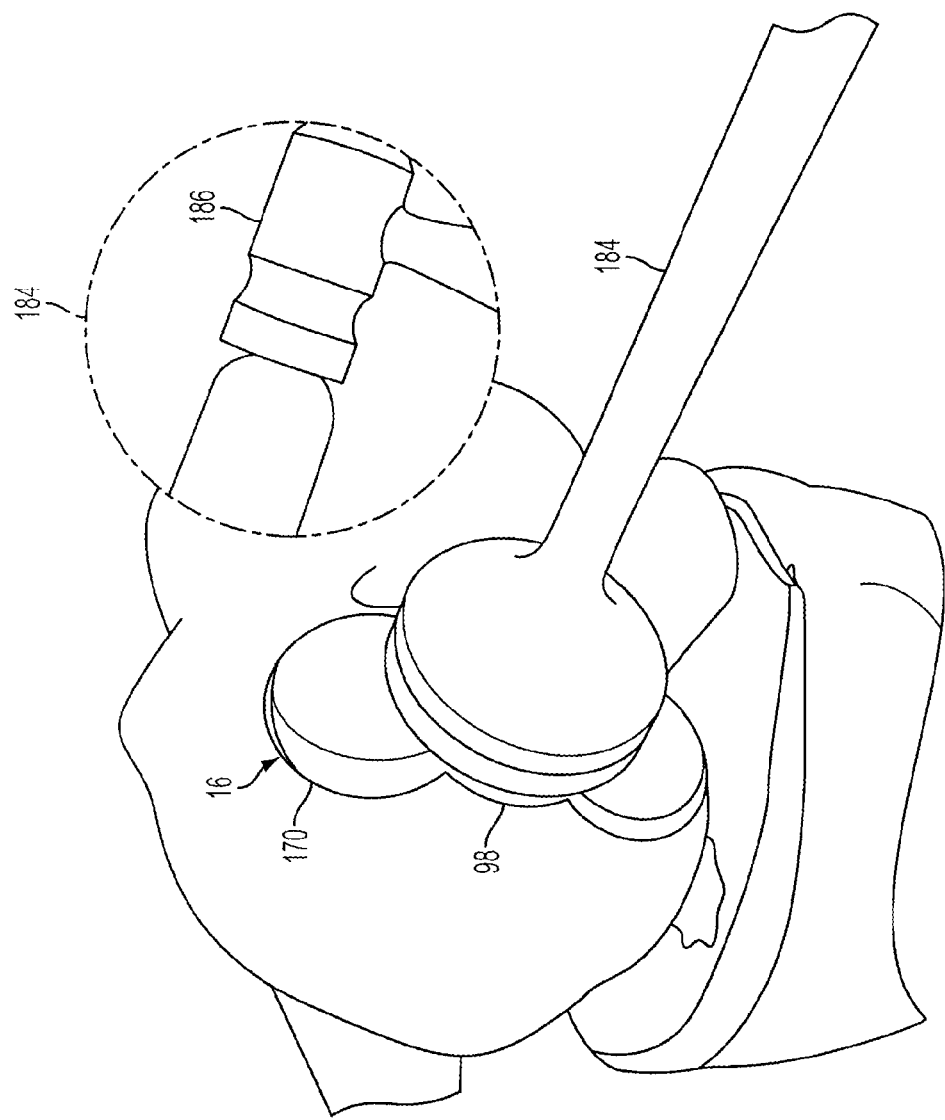
FIG. 33 depicts the implant of FIG. 31 mating with the tapered post of FIG. 25.

Turning now to FIG. 32, an adhesive 180 (such as, but not limited to, bone cement or the like) may be applied to the bone facing surface 172 by way of a dispenser 182, for example a dispenser as described in U.S. patent application Ser. No. 12/031,534 entitled Bone Cement Delivery Device filed on Feb. 14, 2008 which is fully incorporated herein by reference. The implant 170 may include a female opening configured to frictionally engage with the tapered second end of the tapered post 140. For example, the implant 170 may be mated in the excision site 98 and to the tapered post 140 using an impactor 184 and hammer 186 as shown in FIG. 33.

Figure 34:
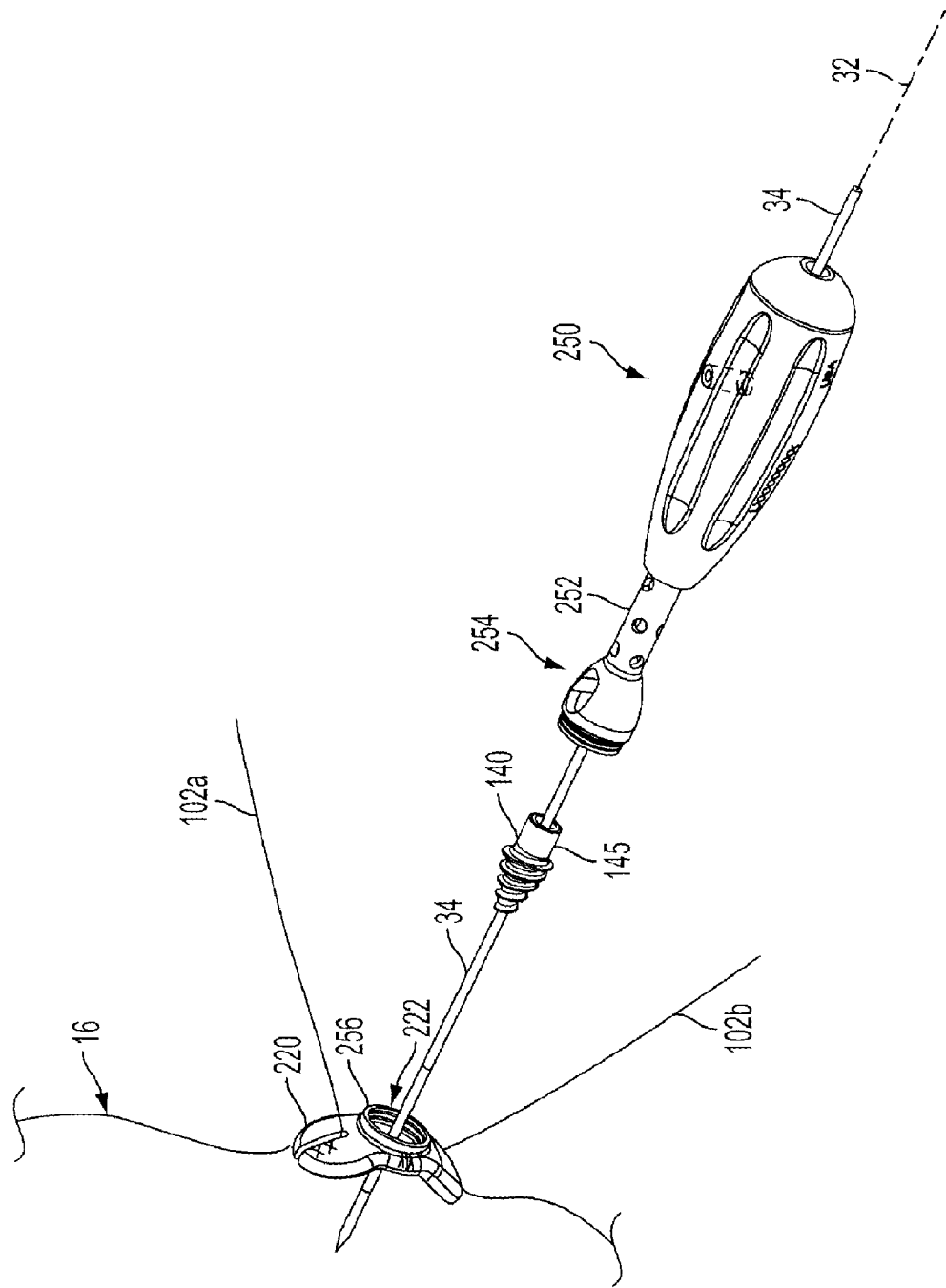
FIG. 34 is a perspective view of a guide handle assembly.

According to another embodiment, the tapered post 140 may be advanced into the bone as follows. After forming a threaded opening 138 (for example, but not limited to, as described above with respect to FIG. 24), an implant sizing trial 220 may be advanced along the guide pin 34 into the excision site 98 as generally shown in FIG. 34. The implant sizing trial 220 may be similar to the implant sizing trial 120 described above, however, the implant sizing trial 220 according to this embodiment may include a threaded opening 222 having a diameter large enough to allow the tapered post 140 to be advanced along the guide pin 34 (and therefore the reference axis 32) through the threaded opening 222 and into the bone. The implant sizing trial 220 may be advanced along the guide pin 34 using a guide handle assembly 250. The guide handle assembly 250 may include a cannulated shaft 252 to receive the guide pin 34 and may also include a flared end 254 configured to receive the tapered second end 145 of the tapered post 140.

For example, turning to FIG. 35, the guide handle assembly 250 and the tapered post 140 are shown together with the implant sizing trial 220. As can be seen, the flared end 254 of the guide handle assembly 250 may be configured to engage with a shoulder 156 of the implant sizing trial 220 proximate the threaded opening 222. Referring now to FIG. 35a, a close up of the flared end 254 of the guide handle assembly 250 and the tapered post 140 is shown. The flared end 254 may define an internal cavity 260 configured to at least partially receive the tapered post 140. In particular, the internal cavity 260 may include a tapered portion 262 configured to frictional engage with the tapered second end 145 of the tapered post 140. Additionally, as can be seen, the flared end 254 of the guide handle assembly 250 may include a shoulder 264 configured to engage against the shoulder 256 of the implant sizing trial 220. At this point, the tapered post 140 may or may not be partially received within the threaded opening 138. The final depth of the tapered post 140 may also not be set.

Turning now to FIG. 36, the tapered post 140 may be partially advanced into the threaded opening 138 using a hex driver 270. For example, the hex driver 270 may be advanced along the guide pin 34 and the reference axis 32 through the cannulated passageway of the guide handle assembly 250. The hex driver 270, FIG. 36a, may include a male hex adapter 272 configured to engage with a corresponding female hex adapter 147 of the tapered post 140.

With the shoulder 264 of the guide handle assembly 250 abutting against the shoulder 256 of the implant sizing trial 220, the tapered post 140 may be advanced along the guide pin 34 and the reference axis 32 as shown in FIG. 37 using the hex driver 270. According to one embodiment, the tapered post 140 is advanced most of the way into the bone and the depth may be set based on a marking 276 (for example a laser marking or the like) on the shaft 278 of the hex driver 270. This marking 276 may be used to set the tapered post 140 close to the final depth in the bone, for example by aligning the marking 276 with the distal end of the guide handle assembly 250. Alternatively, it may be possible to set the final depth of the tapered post 140 based on this marking 276 and the guide handle assembly 250. As may be seen in FIG. 37a, flared end 254 of the guide handle assembly 250 may include a threaded region 277 that may engage with the threaded opening 222 of the implant sizing trial 220. Additionally, the tapered second end 154 of the tapered post 140 may be at least partially removed from the tapered portion 262 of the flared end 254 of the guide handle assembly 250 once the marking 276 is aligned with the guide handle assembly 250.

Figure 38:
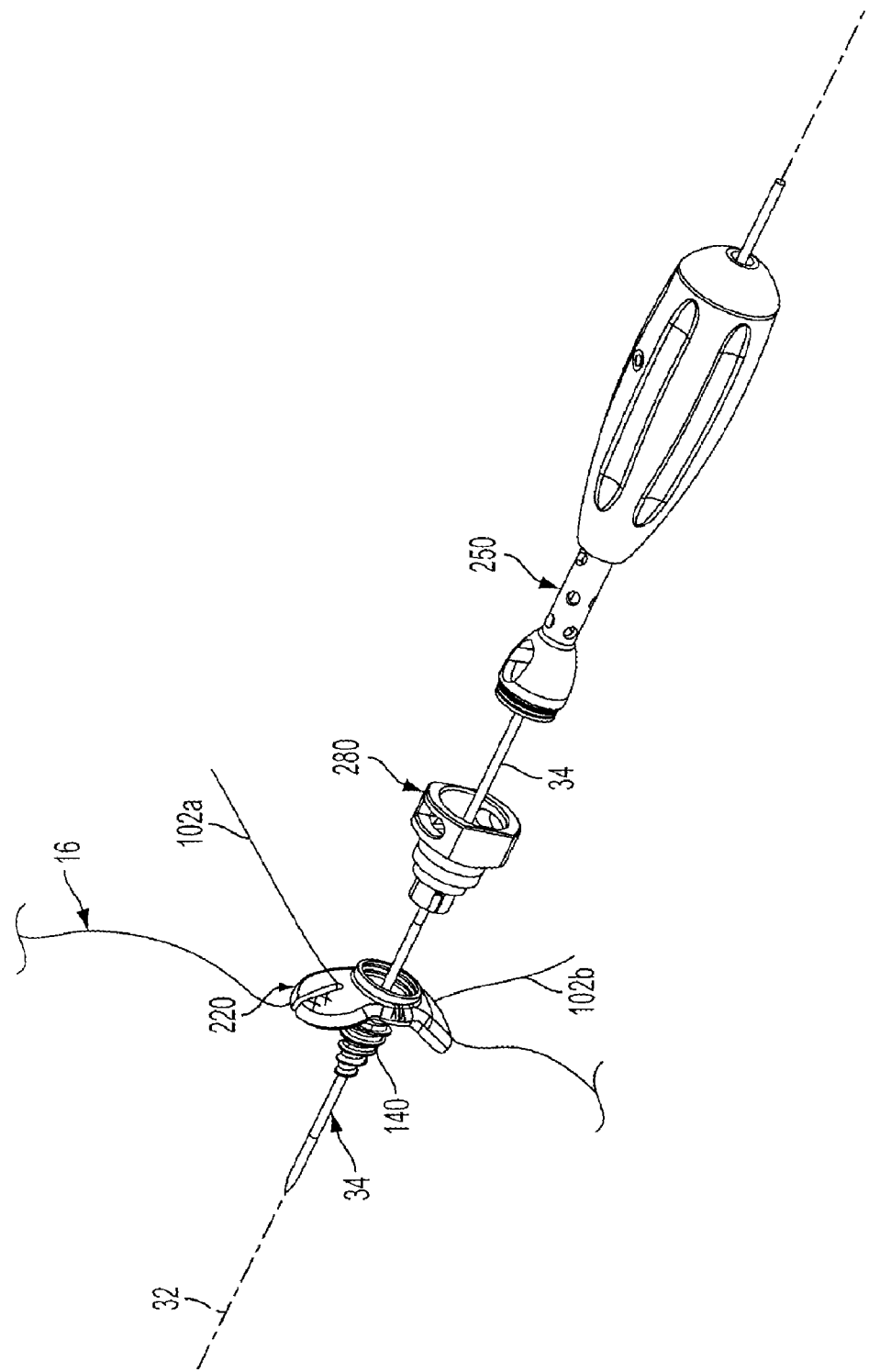
FIG. 38 is a perspective view of a trial, placement gauge, and guide handle.
Figure 39:
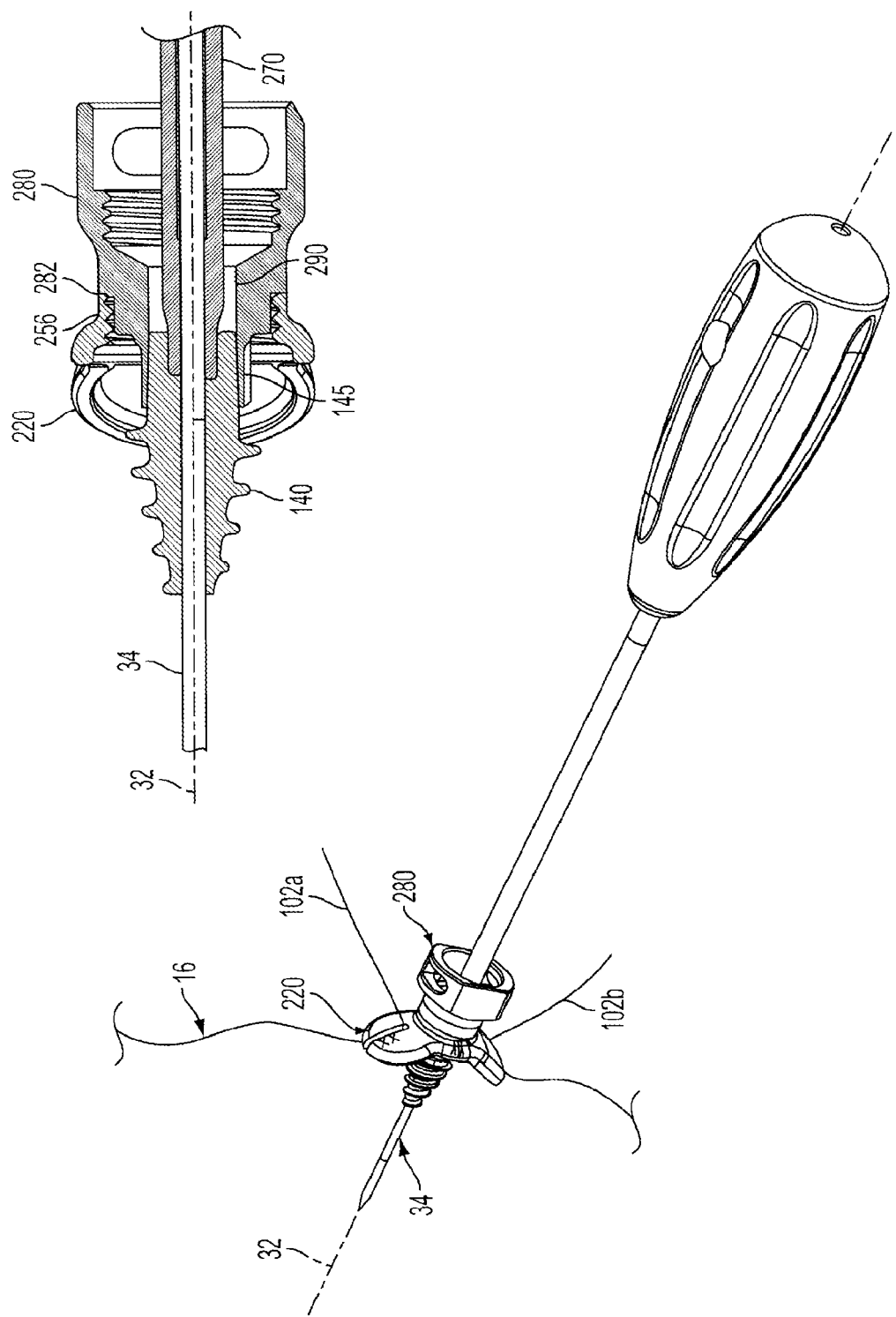
FIG. 39 is a side plan view of the trial, placement gauge, and guide handle of FIG. 38 disposed about the articular surface.

Turning now FIG. 38, the hex driver 270 and the guide handle assembly 250 may be removed and a placement gauge 280 may be advanced along the guide pin 34 towards the implant sizing trial 220. The placement gauge 280 may be used to set the final depth of the tapered post within the bone. The placement gauge 280 may be advanced along the guide pin 34 using the guide handle assembly 250. As shown in FIG. 39, the placement gauge 280 may include a tapered female cavity 290 configured to engage with the tapered second end 145 of the tapered post 140 in a manner substantially the same as the implant will ultimately engage with the tapered post 140.

With the tapered female cavity 290 of the placement gauge 280 frictionally engaged with the tapered post 140, the placement gauge 280 and the tapered post 140 may be advanced along the guide pin 34 using the hex driver 270 until a shoulder 282 of the placement gauge 280 abuts against the shoulder 256 of the implant sizing trial 220. The final depth of the implant 140 may be set based on the implant sizing trial 140 (and in particular, the depth of the shoulder/boss 256) and the depth of the tapered post 140 within the tapered cavity 290 of the placement gauge 280.

Once the tapered post 140 is set in the bone, the hex driver 270, placement gauge 280, and the implant sizing trial 220 maybe removed. Once removed, the guide pin 34 may be removed and (if still in place), the pins 102a, 102b may also be removed. The implant may then be coupled to the tapered post 140 as generally described above.

The following patents or patent applications filed by the applicant or assignee of the present invention are hereby incorporated by reference in their entireties:

U.S. Pat. No. 6,520,964 entitled System and method for joint resurface repair;
    U.S. Pat. No. 6,610,067 entitled System and method for joint resurface repair;
    U.S. Pat. No. 7,029,479 entitled System and method for joint resurface repair;
    U.S. Pat. No. 6,679,917 entitled System and method for joint resurface repair;
    U.S. Pat. No. 7,163,541 entitled Tibial resurfacing system;
    U.S. patent application Ser. No. 10/373,463 entitled System and method for joint resurface repair;
    U.S. patent application Ser. No. 11/359,891 entitled Articular surface implant;
    U.S. patent application Ser. No. 10/618,887 entitled System and method for joint resurface repair;
    U.S. patent application Ser. No. 11/379,151 entitled System and method for joint resurface repair;
    U.S. patent application Ser. No. 10/760,965 entitled System and method for joint resurface repair;
    U.S. patent application Ser. No. 12/027,121 entitled System and method for joint resurface repair;
    U.S. patent application Ser. No. 10/789,545 entitled Articular Surface Implant;
    U.S. patent application Ser. No. 11/461,240 entitled System and method for articular surface repair;
    U.S. patent application Ser. No. 11/169,326 entitled System for articular surface replacement;

U.S. patent application Ser. No. 11/209,170 entitled System and method for retrograde procedure;

U.S. patent application Ser. No. 11/359,892 entitled Articular surface implant and delivery system;

U.S. patent application Ser. No. 11/326,133 entitled System and method for retrograde procedure;

U.S. patent application Ser. No. 11/551,912 entitled Retrograde excision system and apparatus;

U.S. patent application Ser. No. 12/001,473 entitled Retrograde resection apparatus and method;

U.S. patent application Ser. No. 11/779,044 entitled System and method for tissues resection; and U.S. patent application Ser. No. 12/031,534 entitled Bone cement delivery device.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure.

What is claimed is:

1. A method for preparing an implant site in bone, comprising:
   establishing a first working axis extending from said bone;
   establishing a second working axis extending from said bone, said second working axis is displaced from said first working axis;
   creating a first socket in said bone by reaming about said first working axis;
   creating a second socket in said bone, adjacent said first socket, by reaming about said second working axis;
   advancing a cannulated drill guide to contact said bone, said cannulated drill guide comprising a cannulated handle and a first arcuate tip section removably coupled to a distal end of said cannulated handle, said first arcuate tip section comprising first and second bone contacting points and a bore aligned with a lumen of said cannulated handle, wherein said first working axis is defined extending from said bone through said bore and said lumen;
   installing a first guide pin into said bone through said lumen and said bore and along said first working axis;
   advancing a cannulated bone centering shaft over said first guide pin, said bone centering shaft comprising a cannulated tap portion and a cannulated shaft, a shoulder portion between said tap portion and said shaft, and at least one visual marker on said cannulated shaft;
   driving said tap portion into said bone to a predetermined depth;
   advancing a cannulated contact probe over said centering shaft, said contact probe comprising an outrigger extending radially from a cannulated shaft, said outrigger comprising a contact point, and a handle comprising visual measuring indicia configured to align with said visual marker, wherein said visual measuring indicia and said visual marker configured to visually display a depth of said contact point when said contact point is advanced to contact said bone;
   determining a plurality of depth measurements in at least one plane and determining a curvature based on at least one said depth measurement; and
   advancing a first reamer over said centering shaft and rotating said reamer about said centering shaft to create said first socket in said bone.

2. The method of claim 1, wherein said first and second working axes are established, in part, by advancing first and second guide pins into said bone, said guide pins extending from said bone.

3. The method of claim 1, wherein said first and second working axes are established by placing a guide block onto the surface of the bone such that at least two opposing points of the guide blocks contact said bone, said guide block having first and second bores therein defining the location of said first and second working axes with respect to said bone.

4. The method of claim 1, further comprising:
   establishing a third working axis extending from said bone, said third working axis is displaced from said first and second working axes; and
   creating a third socket in said bone, adjacent said first and second sockets, by reaming about said third working axis.

5. The method of claim 1, further comprising:
   advancing a centering shaft into and extending from said bone along said first working axis;
   measuring a plurality of points from a fixed position along said centering shaft to said bone, said plurality of point indicative of a curvature of said bone in at least one plane; and
   selecting, based on said plurality of points, an implant having a bone-facing surface and a load-bearing surface that substantially matches said curvature of said bone.

6. The method of claim 5, further comprising:
   selecting a guide block having a curvature based on said plurality of points;
   advancing said guide block to said bone about said first working axis, said guide block comprising at least two opposing points configured to contact said bone at different locations and first and second bores therein defining the location of said first and second working axes with respect to said bone.

7. The method of claim 5, further comprising:
   advancing a sizing trial implant into, at least in part, said first and second sockets, said sizing trial implant having a curvature of at least one surface thereof based on said plurality of points; and
   confirming that said sizing trial implant fits within said first and second sockets.

8. The method of claim 5, further comprising:
   applying bone adhesive to said implant; and
   installing said implant, at least in part, into said first and second sockets in the bone.

9. The method of claim 1, further comprising:
   removably coupling a guide block onto said distal end of said cannulated handle, said guide block comprising a body portion having a curvature based on at least one said depth measurement, first and second bone contacting points, a first bore aligned with a lumen of said cannulated handle, and a second bore spaced apart from said first bore, said second bore defining said second working axis;
   advancing said guide block and cannulated handle over said first guide pin; and installing a second guide pin into said bone through said second bore and along said second working axis.

10. The method of claim 9, further comprising:
removably coupling a cannulated bushing into said second bore prior to installing said second guide pin.

11. The method of claim 9, further comprising:
advancing a second reamer over said second guide pin and rotating said reamer about said second guide pin to create said second socket in said bone.

12. The method of claim 9, further comprising:
advancing a cannulated tap over said first guide pin and into said bone to tap area of bone surrounding said first guide pin;
advancing a tapered post over said first guide pin into the tapped area of bone to secure said tapered post into said bone.

13. The method of claim 12, further comprising:
selecting an implant comprising a load-bearing surface that substantially matches said curvature of said bone and having a curvature based on at least one said depth measurement, said implant is dimensioned to fit within, at least, said first and second sockets, said implant also comprising a bone-facing surface comprising a recess configured to mate with the taper of said tapered post;
installing said implant into said first and second sockets by mating said recess with said tapered post.

14. The method of claim 13, further comprising:
applying adhesive to said bone-facing surface prior to said installing said implant.

15. A method for preparing an implant site in bone, comprising:
establishing a first working axis extending from said bone;
establishing a second working axis extending from said bone, said second working axis is displaced from said first working axis;
creating a first socket in said bone by reaming about said first working axis;
creating a second socket in said bone, adjacent said first socket, by reaming about said second working axis,
removably coupling a guide block onto said distal end of said cannulated handle, said guide block comprising a body portion having a curvature based on at least one said depth measurement, first and second bone contacting points, a first bore aligned with a lumen of said cannulated handle, and a second bore spaced apart from said first bore, said second bore defining said second working axis;
advancing said guide block and cannulated handle over said first guide pin;
installing a second guide pin into said bone through said second bore and along said second working axis;
advancing a cannulated drill guide to contact said bone, said cannulated drill guide comprising a cannulated handle and a first arcuate tip section removably coupled to a distal end of said cannulated handle, said first arcuate tip section comprising first and second bone contacting points and a bore aligned with a lumen of said cannulated handle, wherein said first working axis is defined extending from said bone through said bore and said lumen; and
installing a first guide pin into said bone through said lumen and said bore and along said first working axis.

16. The method of claim 15, wherein said first and second working axes are established, in part, by advancing first and second guide pins into said bone, said guide pins extending from said bone.

17. The method of claim 15, wherein said first and second working axes are established by placing a guide block onto the surface of the bone such that at least two opposing points of the guide blocks contact said bone, said guide block having first and second bores therein defining the location of said first and second working axes with respect to said bone.

18. The method of claim 15, further comprising:
establishing a third working axis extending from said bone, said third working axis is displaced from said first and second working axes; and
creating a third socket in said bone, adjacent said first and second sockets, by reaming about said third working axis.

19. The method of claim 15, further comprising:
advancing a centering shaft into and extending from said bone along said first working axis;
measuring a plurality of points from a fixed position along said centering shaft to said bone, said plurality of point indicative of a curvature of said bone in at least one plane; and
selecting, based on said plurality of points, an implant having a bone-facing surface and a load-bearing surface that substantially matches said curvature of said bone.

20. The method of claim 19, further comprising:
selecting a guide block having a curvature based on said plurality of points;
advancing said guide block to said bone about said first working axis, said guide block comprising at least two opposing points configured to contact said bone at different locations and first and second bores therein defining the location of said first and second working axes with respect to said bone.

21. The method of claim 19, further comprising:
advancing a sizing trial implant into, at least in part, said first and second sockets, said sizing trial implant having a curvature of at least one surface thereof based on said plurality of points; and
confirming that said sizing trial implant fits within said first and second sockets.

22. The method of claim 19, further comprising:
applying bone adhesive to said implant; and
installing said implant, at least in part, into said first and second sockets in the bone.

23. The method of claim 15, further comprising:
advancing a cannulated bone centering shaft over said first guide pin, said bone centering shaft comprising a cannulated tap portion and a cannulated shaft, a shoulder portion between said tap portion and said shaft, and at least one visual marker on said cannulated shaft;
driving said tap portion into said bone to a predetermined depth;
advancing a cannulated contact probe over said centering shaft, said contact probe comprising an outrigger extending radially from a cannulated shaft, said outrigger comprising a contact point, and a handle comprising visual measuring indicia configured to align with said visual marker, wherein said visual measuring indicia and said visual marker configured to visually display a depth of said contact point when said contact point is advanced to contact said bone;
determining a plurality of depth measurements in at least one plane and determining a curvature based on at least one said depth measurement; and
advancing a first reamer over said centering shaft and rotating said reamer about said centering shaft to create said first socket in said bone.

24. The method of claim 15, further comprising:
removably coupling a cannulated bushing into said second bore prior to installing said second guide pin.

25. The method of claim 15, further comprising:
advancing a second reamer over said second guide pin and rotating said reamer about said second guide pin to create said second socket in said bone.

26. The method of claim 15, further comprising:
advancing a cannulated tap over said first guide pin and into said bone to tap area of bone surrounding said first guide pin;
advancing a tapered post over said first guide pin into the tapped area of bone to secure said tapered post into said bone.

27. The method of claim 26, further comprising:
selecting an implant comprising a load-bearing surface that substantially matches said curvature of said bone and having a curvature based on at least one said depth measurement, said implant is dimensioned to fit within, at least, said first and second sockets, said implant also comprising a bone-facing surface comprising a recess configured to mate with the taper of said tapered post;
installing said implant into said first and second sockets by mating said recess with said tapered post.

28. The method of claim 26, further comprising:
applying adhesive to said bone-facing surface prior to said installing said implant.

\* \* \* \* \*